(12) United States Patent
Nakasuji et al.

(10) Patent No.: US 8,803,103 B2
(45) Date of Patent: *Aug. 12, 2014

(54) INSPECTION SYSTEM BY CHARGED PARTICLE BEAM AND METHOD OF MANUFACTURING DEVICES USING THE SYSTEM

(71) Applicants: Ebara Corporation, Tokyo (JP); Kabushiki Kaisha Toshiba, Kawasaki (JP)

(72) Inventors: Mamoru Nakasuji, Kanagawa (JP); Nobuharu Noji, Kanagawa (JP); Tohru Satake, Kanagawa (JP); Masahiro Hatakeyama, Kanagawa (JP); Toshifumi Kimba, Kanagawa (JP); Hirosi Sobukawa, Kanagawa (JP); Shoji Yoshikawa, Tokyo (JP); Takeshi Murakami, Tokyo (JP); Kenji Watanabe, Kanagawa (JP); Tsutomu Karimata, Kanagawa (JP); Shin Oowada, Kanagawa (JP); Mutsumi Saito, Kanagawa (JP); Yuichiro Yamazaki, Tokyo (JP); Takamitsu Nagai, Kanagawa (JP); Ichirota Nagahama, Kanagawa (JP)

(73) Assignees: Ebara Corporation, Tokyo (JP); Kabushiki Kaisha Toshiba, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/732,897

(22) Filed: Jan. 2, 2013

(65) Prior Publication Data

US 2014/0034831 A1 Feb. 6, 2014

Related U.S. Application Data

(60) Division of application No. 13/243,429, filed on Sep. 23, 2011, now Pat. No. 8,368,031, which is a division of application No. 12/216,233, filed on Jul. 1, 2008, now Pat. No. 8,053,726, which is a continuation of application No. 11/806,573, filed on Jun. 1, 2007, now Pat. No. 7,411,191, which is a division of application No. 09/891,511, filed on Jun. 27, 2001, now Pat. No. 7,241,993.

(30) Foreign Application Priority Data

| Jun. 27, 2000 | (JP) | 2000-193104 |
| Jul. 28, 2000 | (JP) | 2000-229101 |
| Nov. 2, 2000 | (JP) | 2000-335934 |
| Jan. 19, 2001 | (JP) | 2001-011218 |
| Feb. 8, 2001 | (JP) | 2001-031901 |
| Feb. 8, 2001 | (JP) | 2001-031906 |
| Feb. 9, 2001 | (JP) | 2001-033599 |
| Feb. 13, 2001 | (JP) | 2001-035069 |
| May 28, 2001 | (JP) | 2001-158662 |
| May 30, 2001 | (JP) | 2001-162041 |
| Jun. 22, 2001 | (JP) | 2001-189304 |

(51) Int. Cl.
*G21K 5/04* (2006.01)
*H01J 37/26* (2006.01)
*H01J 29/70* (2006.01)
*H01J 37/141* (2006.01)

(52) U.S. Cl.
CPC .............. *H01J 37/266* (2013.01); *H01J 29/70* (2013.01); *H01J 37/141* (2013.01)
USPC ........ 250/397; 250/396 R; 250/398; 250/305; 250/306; 250/307; 250/310; 250/311; 250/492.1; 250/492.3

(58) Field of Classification Search
CPC ......... H01J 37/10; H01J 37/141; H01J 37/26; H01J 37/266; H01J 3/26; H01J 23/09; H01J 23/10; H01J 29/74; H01J 29/76; H01J 29/70
USPC ............. 250/396 R, 397, 398, 305, 306, 307, 250/309, 310, 311, 492.1, 492.2, 492.22, 250/492.23, 492.3
See application file for complete search history.

(56) References Cited

U.S. PATENT DOCUMENTS

| | | | |
|---|---|---|---|
| 4,137,476 A | 1/1979 | Ishii et al. |
| 4,405,435 A | 9/1983 | Tateishi et al. |
| 4,584,479 A | 4/1986 | Lamattina et al. |
| 4,607,167 A | 8/1986 | Petric |
| 4,658,136 A | 4/1987 | Ohtaka et al. |
| 4,680,467 A | 7/1987 | Bryson, III et al. |
| 4,726,689 A | 2/1988 | Pollock |
| 4,803,358 A | 2/1989 | Kato et al. |
| 4,911,103 A | 3/1990 | Davis et al. |
| 4,912,052 A | 3/1990 | Miyoshi et al. |
| 4,926,054 A | 5/1990 | Frosien |
| 4,944,645 A | 7/1990 | Suzuki |
| 5,186,718 A | 2/1993 | Tepman et al. |
| 5,233,191 A | 8/1993 | Noguchi et al. |
| 5,359,197 A | 10/1994 | Komatsu et al. |
| 5,362,968 A | 11/1994 | Miyoshi et al. |
| 5,376,883 A | 12/1994 | Kaito |
| 5,378,283 A | 1/1995 | Ushikawa |
| 5,424,541 A | 6/1995 | Todokoro et al. |
| 5,432,345 A | 7/1995 | Kelly |
| 5,502,306 A | 3/1996 | Meisburger et al. |
| 5,536,128 A | 7/1996 | Shimoyashiro et al. |
| 5,578,821 A | 11/1996 | Meisberger et al. |
| 5,616,920 A | 4/1997 | Plies |
| 5,665,968 A | 9/1997 | Meisburger et al. |
| 5,747,819 A | 5/1998 | Nakasuji et al. |
| 5,751,538 A | 5/1998 | Nakasuji |
| 5,763,893 A | 6/1998 | Nakasuji |
| 5,770,863 A | 6/1998 | Nakasuji |
| 5,892,224 A | 4/1999 | Nakasuji |
| 5,944,049 A | 8/1999 | Beyer et al. |
| 5,973,323 A | 10/1999 | Adler et al. |
| 5,981,947 A | 11/1999 | Nakasuji et al. |
| 5,986,263 A | 11/1999 | Hiroi et al. |
| 5,994,704 A | 11/1999 | Nakasuji |
| 6,000,905 A | 12/1999 | Toro-Lira |
| 6,011,262 A | 1/2000 | Hamashima et al. |
| 6,023,068 A | 2/2000 | Takahashi |
| 6,087,667 A | 7/2000 | Nakasuji et al. |
| 6,125,522 A | 10/2000 | Nakasuji |
| 6,315,512 B1 | 11/2001 | Tabrizi et al. |
| 6,329,826 B1 | 12/2001 | Shinada et al. |
| 6,344,750 B1 | 2/2002 | Lo et al. |
| 6,365,897 B1 | 4/2002 | Hamashima et al. |
| 6,479,819 B1 | 11/2002 | Hamashima et al. |
| 6,518,582 B1 | 2/2003 | Kohama |
| 6,593,578 B1 | 7/2003 | Duval et al. |
| 6,614,026 B1 | 9/2003 | Adamec |
| 6,627,884 B2 | 9/2003 | McCord et al. |
| 6,670,602 B1 | 12/2003 | Kohama et al. |
| 6,765,217 B1 | 7/2004 | Nishimura et al. |
| 6,828,571 B1 | 12/2004 | McCord et al. |
| 7,241,993 B2 * | 7/2007 | Nakasuji et al. ............ 250/310 |
| 7,417,236 B2 * | 8/2008 | Nakasuji et al. ......... 250/440.11 |
| 7,429,740 B2 | 9/2008 | Salvesen et al. |
| 2003/0030008 A1 | 2/2003 | Sobukawa et al. |
| 2003/0164934 A1* | 9/2003 | Nishi et al. ....................... 355/72 |
| 2006/0043982 A1* | 3/2006 | Shinada et al. ............... 324/751 |

FOREIGN PATENT DOCUMENTS

| | | | |
|---|---|---|---|
| EP | 200333 A2 | 11/1986 |
| EP | 0200333 A2 | 12/1986 |
| EP | 0312082 A2 | 4/1989 |
| EP | 584790 A1 | 3/1994 |
| EP | 0848247 A1 | 6/1998 |
| EP | 0 952 488 A2 | 10/1999 |
| EP | 1061359 A2 | 12/2000 |
| EP | 1219956 A2 | 7/2002 |
| GB | 2171119 A | 8/1986 |
| JP | 52-115161 A | 9/1977 |
| JP | 52-117567 A | 10/1977 |
| JP | 57-072326 A | 5/1982 |
| JP | 57-119442 A | 7/1982 |
| JP | 57-125871 A | 8/1982 |
| JP | 57-147857 A | 9/1982 |
| JP | 58-018833 A | 2/1983 |
| JP | 60-000741 A | 1/1985 |
| JP | 60-000741 U | 1/1985 |
| JP | 62-093934 A | 4/1987 |
| JP | 62-100936 A | 5/1987 |
| JP | 62-195838 A | 8/1987 |
| JP | 63-006737 A | 1/1988 |
| JP | 03-022339 A | 1/1991 |
| JP | 03-053439 A | 3/1991 |
| JP | 03-102814 U | 4/1991 |
| JP | 03-266350 A | 11/1991 |
| JP | 03-276548 A | 12/1991 |
| JP | 04-266350 A | 9/1992 |
| JP | 04-331390 A | 11/1992 |
| JP | 05-063261 A | 3/1993 |
| JP | 05-109381 A | 4/1993 |
| JP | 05109381 A | 4/1993 |
| JP | 05-251316 A | 9/1993 |
| JP | 06-338280 A | 12/1994 |
| JP | 07-065766 A | 3/1995 |
| JP | 07-249393 A | 9/1995 |
| JP | 08-138611 A | 5/1996 |
| JP | 08-222176 A | 8/1996 |
| JP | 09-73872 A | 3/1997 |
| JP | 9-180665 A | 7/1997 |
| JP | 09-311112 A | 12/1997 |
| JP | 09-320505 A | 12/1997 |
| JP | 10-012684 A | 1/1998 |
| JP | 10-062503 A | 3/1998 |
| JP | 10-125271 A | 5/1998 |
| JP | 10-177952 A | 6/1998 |
| JP | 11-108059 A | 4/1999 |
| JP | 11-132975 A | 5/1999 |
| JP | 11-223662 A | 8/1999 |
| JP | 11-233062 A | 8/1999 |
| JP | 2000-3692 A | 1/2000 |
| JP | 2000-047371 A | 2/2000 |
| JP | 2000-067798 A | 3/2000 |
| JP | 2000-090868 A | 3/2000 |
| JP | 2000-100369 A | 4/2000 |
| JP | 2000-133565 A | 5/2000 |
| JP | 2000-149853 A | 5/2000 |
| JP | 2000-161948 A | 6/2000 |
| JP | 2000-315712 A | 11/2000 |
| JP | 2000-323538 A | 11/2000 |
| WO | 98/32153 A2 | 7/1998 |
| WO | 98/54632 A2 | 12/1998 |
| WO | 00/72355 A1 | 11/2000 |

OTHER PUBLICATIONS

Extended European Search Report dated Mar. 14, 2013, issued in corresponding European Patent Application No. 13000328.8.
Lischke, B. et al "Multi-Beam Concepts for Nanometer Devices," Japanese Journal of Applied Physics, vol. 28 No. 10, Oct. 1989, pp. 2058-2064.
Meisburger, W.D. et al "Requirements and Performance of an Electron-Beam Column Designed for X-ray Mask Inspection," Journal of Vacuum Science and Technology, vol. 9 No. 6, 1991, pp. 3010-3014.
Sandland, P. et al "An Electron-Beam Inspection System for X-ray Mask Production," Journal of Vacuum Science and Technology, vol. 9 No. 6, 1991, pp. 3005-3009.
European Search Report dated Mar. 19, 2007, issued in corresponding European patent Application No. 01 94 5627.
H. Hayashi et al., LSI Testing Symposium 1998. Minutes of the Meeting , p. 160(1998) (Partiail translation).
Nakasuji et al., "High-Emittance and Low-Brightness Electron Gun for Reducing-Image Projection System: Computer Simulation"; Jpn. J. Appl. Phys. vol. 36 (1997) pp. 2404-2408.
Nakasuji et al., "Low Voltage and High speed operating electrostatic wafer chuck using sputtered tantalum oxide membrance"; J. Vac. Sci. Technol. A125(5), Sep./Oct. 1994, American Vacuum Society, pp. 2834-2839.
Table 5-1 Work Function in Metals, p. 116.

European Search Report dated Dec. 6, 2011, issued in corresponding European Patent Application No. 11004165.4.

* cited by examiner

*Primary Examiner* — Nicole Ippolito
(74) *Attorney, Agent, or Firm* — Westerman, Hattori, Daniels & Adrian, LLP

(57) ABSTRACT

An inspection apparatus by an electron beam comprises: an electron-optical device 70 having an electron-optical system for irradiating the object with a primary electron beam from an electron beam source, and a detector for detecting the secondary electron image projected by the electron-optical system; a stage system 50 for holding and moving the object relative to the electron-optical system; a mini-environment chamber 20 for supplying a clean gas to the object to prevent dust from contacting to the object; a working chamber 31 for accommodating the stage device, the working chamber being controllable so as to have a vacuum atmosphere; at least two loading chambers 41, 42 disposed between the mini-environment chamber and the working chamber, adapted to be independently controllable so as to have a vacuum atmosphere; and a loader 60 for transferring the object to the stage system through the loading chambers.

7 Claims, 50 Drawing Sheets

(a)

Fig. 42
IMAGES TO BE INSPECTED
AT DIFFERENT LOCATIONS
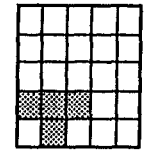
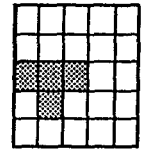
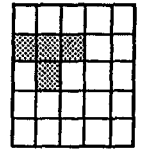
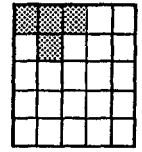
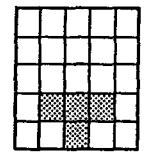
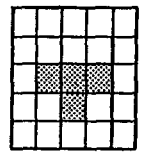
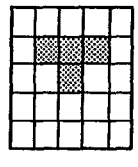
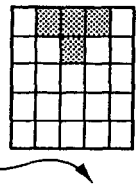
1030a
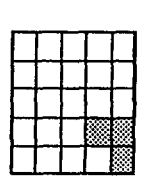
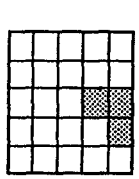
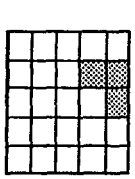
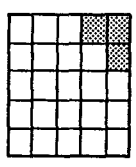
1032
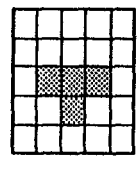
REFERENCE IMAGE 1036

INSPECTION SYSTEM BY CHARGED PARTICLE BEAM AND METHOD OF MANUFACTURING DEVICES USING THE SYSTEM

CROSS-REFERENCE TO RELATED APPLICATIONS

This application is a divisional application of U.S. application Ser. No. 13/243,429, filed Sep. 23, 2011, which is a divisional application of U.S. application Ser. No. 12/216,233, filed Jul. 1, 2008, now U.S. Pat. No. 8,053,726, which is a Continuation of U.S. application Ser. No. 11/806,573, filed Jun. 1, 2007, now U.S. Pat. No. 7,411,191, which is a divisional of U.S. application Ser. No. 09/891,511, filed Jun. 27, 2001, now U.S. Pat. No. 7,241,993, issued Jul. 10, 2007. Application Ser. No. 09/891,511 claims priority for Application Nos. 2000-193104; 2000-229101; 2000-335934; 2001-011218; 2001-031901; 2001-031906; 2001-033599; 2001-035069; 2001-158662; 2001-162041; 2001-189304, filed on Jun. 27, 2000; Jul. 28, 2000; Nov. 2, 2000; Jan. 19, 2001; Feb. 8, 2001; Feb. 8, 2001; Feb. 9, 2001; Feb. 13, 2001; May 28, 2001; May 30, 2001; and Jun. 22, 2001, respectively, all of which were filed in Japan.

BACKGROUND OF THE INVENTION

1. Field of the Invention

The present invention relates to an electron beam based inspection apparatus for inspecting defects in patterns formed on the surface of an object to be inspected, and more particularly, to an inspection apparatus useful, for example, in inspecting defects on a wafer in a semiconductor manufacturing process, which includes irradiating an object to be inspected with an electron beam, detecting secondary electrons which vary in accordance with the properties of the surface thereof to form image data, and inspecting patterns formed on the surface of the object to be inspected based on the image data at a high throughput, and a method of manufacturing devices at a high yield rate using the inspection apparatus. More specifically, the invention relates to a projection type electron beam inspection apparatus which adopts a area beam and a method of manufacturing devices using the inspection apparatus.

2. Field of the Invention

In semiconductor processes, design rules are reaching 100 nm and the method of production form is evolving from mass production, with a few models, such as a DRAM, into small-lot production with a variety of models such as a SOC (Silicon on chip). This has resulted in an increase in the number of processes, and an improvement in yield for each process is essential; which makes it more important to inspect for defects occurring in each process. The present invention relates to an apparatus to be used in the inspection of a wafer after particular steps in the semiconductor fabrication process, and in particular to an inspection method and apparatus using an electron beam and also to a device manufacturing method using the same.

3. Description of the Related Art and Problems to be Solved by the Invention

4. Description of the Prior Art

In conjunction with a high level of integration of semiconductor devices and a micro-fabrication of patterns thereof, an inspection apparatus with higher resolution and throughput is desired. In order to inspect a wafer substrate with 100 nm design rules for any defects, a resolution equal to or finer than 100 nm is required, and the increased number of processes resulting from large-scale integration of devices calls for an increase in the number of inspections, which consequently requires higher throughput. In addition, as multilayer fabrication of devices has advanced, the apparatus is further required to have a function for detecting contact failures in vias for interconnecting wiring between layers (i.e., electrical defects). In the current trend, an inspection apparatus using optical methods has been typically used, but it is expected that an inspection apparatus using an electron beam may soon enter the mainstream, substituting for inspection apparatus using optical methods, given the requirements of higher resolution and detection of contact failures. The electron beam method, however, has a weak point in that it is inferior to the optical method in throughput.

Accordingly, it is desirable to have an apparatus having higher resolution and throughput and being capable of detecting the electrical defects. It has been known that the resolution of the optical method is limited to {fraction (½)} of the wavelength of the light to be used, and it is about 0.2 .mu.m in a typical case of visible light being put to practical use.

On the other hand, in the method using an electron beam, typically a scanning electron microscopy method (SEM method) has been put to use, wherein the resolution thereof is 0.1 .mu.m and the inspection time is 8 hours per wafer (20 cm wafer). The electron beam method has the distinctive feature that it is able to inspect for any electrical defects (breaking of wires in the wirings, bad continuity, bad continuity of via). However, the inspection speed (sometimes also referred to as inspection rate) thereof is very low, and so the development of an inspection apparatus with higher inspection speed has been eagerly anticipated.

Generally, since an inspection apparatus is expensive and the throughput thereof is rather lower as compared to other processing apparatuses, the inspection apparatus has been used after an important process, for example, after the process of etching, film deposition, CMP (Chemical-mechanical polishing) flattening or the like.

The scanning method (SEM) using an electron beam will now be described. In the inspection apparatus of SEM method, the electron beam is contracted to be finer (the diameter of this beam corresponds to the resolution thereof) and this fined beam is used to scan a sample so as to irradiate it linearly. On the other hand, moving a stage in the direction normal to the scanning direction allows an observation region to be irradiated by the electron beam as a plane area. The scanning width of the electron beam is typically some 100 .mu.m. Secondary electrons emanating from the sample by the irradiation of said contracted and fined electron beam (referred to as a primary electron beam) are detected by a detector, either a scintillator plus photo-multiplier (i.e., photoelectron multiplier tube) or a detector of semiconductor type (i.e., a PIN diode) or the like. The coordinates for the irradiated locations and an amount of the secondary electrons (signal intensity) are combined and formed into an image, which is stored in some recording medium or displayed on a CRT (a cathode ray tube). The above description illustrates the principles of the SEM (scanning electron microscopy), and defects in a semiconductor wafer (typically made of Si) in the course of processes may be detected from the image obtained in this method. The inspection rate (corresponding to the throughput) is varied depending on the amount (the current value), beam diameter, and speed of response of the primary electron beam. A beam diameter of 0.1 .mu.m (which may be considered to be equivalent to the resolution), a current of 100 nA, and a detector speed of 100 MHz are currently the highest values, and in using those values the inspection rate has been about 8 hours for one wafer having a diameter of 20 cm. This inspection rate, which is extremely low compared to the optical method (not greater than {fraction (1/20)}), has been a serious production problem (drawback).

Also, in regard to the prior art of inspection apparatus related to the present invention, an apparatus using a scanning electron microscope (SEM) has been commercially available. This apparatus involves scanning an object to be inspected with a fine electron beam at very narrow intervals of scanning width, detecting secondary electrons emitted from the object to form a SEM image, and comparing such SEM images of different dies at the same locations to extract defects of the object being inspected.

Conventionally, however, there has been no electron beam based defect inspection apparatus which is completed as a general system.

A defect inspection apparatus which applies SEM requires a long time for defect inspection. In addition, increasing the beam current to improve throughput would cause a degradation of the beam due to the space-charge effect and charging on the wafer with insulating material formed on the surface thereof, thereby failing to produce satisfactory SEM images.

Hitherto, no proposal has been made for the overall structure of an inspection apparatus which takes into account the combination of an electron-optical device for irradiating an object to be inspected with an electron beam, with other subsystems associated therewith for positioning the object to be inspected to for irradiating by the electron-optical device in a clean state, and for aligning the object to be inspected. Further, with the trend of increasing diameters of wafers to be subjected to inspection, the subsystems are also required to cope with wafers of such large diameters.

In view of the problems mentioned above, it is an object of the present invention to provide an inspection apparatus which employs an electron beam based electron-optical system, and achieves harmonization of the electron-optical system with other components, which constitute the inspection apparatus, to improve the throughput.

It is another object of the present invention to provide an inspection apparatus which is capable of efficiently and accurately inspecting an object by improving a loader for carrying the object to be inspected between a cassette for storing objects under inspecting and a stage device for aligning the object to be inspected with respect to the electron-optical system, and devices associated with the loader.

It is a further object of the present invention to provide an inspection apparatus which is capable of solving the problem of charging, experienced in the SEM, to accurately inspect an object.

It is a further object of the present invention to provide a method of manufacturing devices at a high yield rate by inspecting an object such as a wafer, using the inspection apparatus as mentioned above.

Also, with increasing integration of semiconductors, there has been a need for a sensitive inspection apparatus to be used in the semiconductor device manufacturing process for defect inspection in the pattern or the likes in semiconductor wafers. In this regard, there have been electron microscopes used as the inspection apparatus for such defect inspections, as disclosed in Japanese Patent Laid-open Publications Nos. Hei 2-142045 and Hei 5-258703.

For example, in the electron microscope as disclosed in Japanese Patent Laid-open Publication No. Hei 2-142045, an electron beam emitted from an electron gun is converged by an objective lens to irradiate a sample to be inspected, and secondary electrons emitted from the sample are detected by a secondary electron detector. In addition, in this electron microscope, a negative voltage is applied to the sample, and further an E.times.B type filter is arranged between the sample and the secondary electron detector, said filter having an electric field and a magnetic field crossed at right angles.

With such a configuration, this electron microscope allows a high resolution to be obtained by decelerating the electrons irradiated onto the sample by way of the negative voltage applied to the sample.

Further, the application of the negative voltage to the sample helps accelerate the secondary electrons emitted from the sample, and the accelerated secondary electrons are further deflected by the E.times.B type filter toward the secondary electron detector, thus to be efficiently detected by the secondary electron detector.

In those conventional apparatuses using the electron microscope as described above, the electron beam from the electron gun is kept accelerated to be highly energized until just before it impinges onto the sample, by a lens system such as an objective lens with a high voltage applied. Then, the negative voltage applied to the sample decelerates electrons impinging upon the sample, thus allowing a high resolution to be achieved.

However, since the high voltage is applied to the objective lens, while the negative voltage is applied to the sample, there has been a risk that an electric discharge may occur between the objective lens and the sample.

Further, in the electron microscope in the prior art, even in the case where no negative voltage is applied to the sample, if there is a great potential difference between the objective lens and the sample, then it is again feared that the electric discharge may occur between the objective lens and the sample.

Still further, if the voltage applied to the objective lens is set lower in order to deal with a possible electric discharge to the sample, the electrons aren't sufficiently energized, resulting in a poor resolution.

An explanation will be further given for a case where the sample to be inspected is a semiconductor wafer having a via, that is a wiring pattern extending in the approximately vertical direction to the upper-layer and lower-layer wiring planes for providing an electrical connection between the upper layer wiring and the lower layer wiring.

When the semiconductor wafer with the via is inspected for defects by using a conventional electron microscope, a high voltage, for example, a voltage of 10 kV is applied to the objective lens as in the above description. Further, in this case, it is assumed that the semiconductor wafer is grounded. Accordingly, an electric field is generated between the semiconductor wafer and the objective lens.

These conditions could make the electric field more intense in the vicinity of the via on the surface of the semiconductor wafer, thus forming a high electric field. Then, when the electron beam is irradiated onto the via, a large number of secondary electrons is emitted from the via, which is further accelerated by the high electric field in the vicinity of the via. Those accelerated secondary electrons have a sufficient energy (>3 eV) to ionize a residual gas generated by the irradiation of the electron beam onto the semiconductor wafer. Accordingly, the secondary electrons ionize the residual gas so as to generate ionized charged particles.

Then, said ionized charged particles, i.e., the positive ions, are accelerated by the high electric field in the vicinity of the via toward the via to impinge against the via, so that more secondary electrons are emitted from the via. Through a series of these positive feedback, eventually an electric discharge occurs between the objective lens and the semiconductor wafer and damages the pattern or the like on the semiconductor wafer, which has been problematic in the prior art.

Thus, an object of the present invention is to provide an electron gun apparatus which can prevent an electric discharge to a sample being inspected and a method for manufacturing a device by using said electron gun apparatus.

Also, as stated above, an inspection for defects in a mask pattern used in manufacturing a semiconductor device or in a pattern formed on a semiconductor wafer has been performed by the steps of detecting secondary electrons emitted from a sample upon irradiation of a primary electron beam against a surface of the sample, obtaining a pattern image of the sample, and comparing said image with a reference image. Typically, such defect inspection apparatus has been equipped with an E.times.B separator for separating the primary electrons and the secondary electrons.

FIG. 52 shows schematically a typical configuration of a projective electron beam inspection apparatus having an E.times.B separator. An electron beam emitted from an electron gun 721 is formed to be rectangular in shape with a forming aperture (not shown) and reduced in size by the electrostatic lenses 722, thus to be a formed beam of 1.25 mm square at the center of an E.times.B separator 723. The formed beam is deflected by the E.times.B separator 723 so as to be normal to a sample W, and reduced to be {fraction (⅕)} in size with an electrostatic lens 722, which is then irradiated against the sample W. A beam of the secondary electrons emitted from the sample W has a certain intensity corresponding to the pattern data on the sample W, which is expanded by the electrostatic lenses 724, 741, and then enters into a detector 761. The detector 761 generates an image signal corresponding to the intensity of the received secondary electrons, which is compared with a reference image, thereby detecting any defects in the sample.

The E.times.B separator 723 has a configuration in which an electric field and a magnetic field cross at right angles within a plane orthogonal to the normal of the surface of the sample W (the upward direction on paper), so that it advances the electrons straight forward when the relationship of the electric field, the magnetic field, and the energy and speed of the electrons meets certain criteria, while it deflects the electrons in any case other than the said case. In the inspection apparatus of FIG. 44, the conditions are set so that the secondary electrons are advanced straight ahead.

FIG. 53 shows more precisely the movements of the secondary electrons emitted from the rectangular area on the surface of the sample W, which has been exposed to the primary electron beam. The secondary electrons emitted from the sample surface are magnified with the electrostatic lens 724, and imaged onto a central area 723a of the E.times.B separator 723. Since the electric field and the magnetic field of the E.times.B separator 723 have been set such that the secondary electrons are allowed to be advanced straight ahead, the secondary electrons are thus advanced straight ahead to be magnified with the electrostatic lenses 741-1, 741-2 and 741-3, and then imaged on a target 761a within the detector 761. Then, the electron in the image is multiplied by MCP (Multi Channel Plate, not shown) and is formed into an image by a scintillator, CCD (Charge Coupled Device), or the like (not shown). Reference numerals 732 and 733 respectively designate aperture diaphragms arranged in a secondary optical system.

FIG. 54 shows a schematic configuration of a conventional E.times.B separator and the distribution of an electric field generated by said separator. A pair of parallel plate electrodes 723-1 and 723-2 is used to generate an electric field, and a pair of magnetic poles 723-3 and 723-4 is used to generate a magnetic field orthogonal to said electric field. In this configuration, since the magnetic poles 723-3 and 723-4 are made of metals having the ground potential, the electric field is forced to bend toward the ground sides. Accordingly, the distribution of the electric field is as shown in FIG. 54, and the parallel pattern of the electric field may only be obtained in the small central region.

In the case where an E.times.B separator having such a configuration as described above has been applied to a defect inspection apparatus such as a projective electron beam inspection apparatus, there has been a problem of efficiency in inspection in that the irradiated region of the electron beam cannot be enlarged, in order to perform a precise inspection.

Thus, an another object of the present invention is to provide an E.times.B separator which allows a region including both the electric field and the magnetic field having uniform intensities and cross at right angles to each other, to be expanded in a plane parallel to a sample, and which also allows the outer diameter of the whole body to be reduced. Further, another object of the present invention is to reduce the aberration for the detected image obtained, by means of said E.times.B separator applied to a defect inspection apparatus, thus to conduct the precise defect inspection efficiently.

Also, as stated above, there is a conventional apparatus which, in an inspection of a pattern on a semiconductor wafer or a photo mask with an electron beam, reveals a defect in the following way: primarily it scans the surface of a sample such as the semiconductor wafer or the photo mask, or it scans the sample, by sending the electron beam thereto; secondarily it detects secondary charged particles generated from the surface of said sample to generate image data based on the detected result; and lastly it compares the data per cell or die.

However, the above defect inspection apparatus in the prior art has been problematic in that the irradiation of the electron beam causes the surface of the sample to be charged, and carriers from this charging cause a distortion in the image data, which makes it difficult to detect any defects accurately. When alternatively the electron beam current is reduced to make the distortion by the carriers small enough to resolve the problem of said distortion in the image data, the S/N ratio for the secondary electron signal is adversely affected, so that the possibility of invalid error detection is increased, which has been another problem. Further, it has also been a problem in the prior art that multiple scanning and averaging processes for improving the S/N ratio causes a decrease in throughput.

Therefore, another object of the present invention is to provide an apparatus which prevents any distortion from being caused by charging, or which minimizes such distortions if any, and thereby allows a highly accurate defect inspection to be performed, and also to provide a method for manufacturing a device by using said apparatus.

Also, there has been known an apparatus for inspecting a substrate for any defects in an image formed on the substrate in such a manner that the apparatus irradiates a charged particle beam against a surface of the substrate to scan said surface by said charged particle beam, detects secondary electrons emanated from the surface of the substrate, generates image data from the detected result, and then compares the data for each die to one another to detect those defects.

However, this type of imaging apparatus according to the prior art, including the above-described apparatus that has been disclosed in the publication, has been problematic in that the potential distribution on the surface of the substrate or the object to be inspected is not necessarily uniform and the contrast of the image is insufficient, which may cause distortion.

Therefore, a further object of the present invention is to provide an imaging apparatus having an improved performance in defect detection without any loss of throughput.

Another object of the present invention is to provide an imaging apparatus having an improved performance in defect detection by improving the contrast in an image obtained by the detection of secondary electrons from the object to be inspected.

Still another object of the present invention is to provide an imaging apparatus having improved performance in defect detection by making uniform the potential distribution on the surface of an object to be inspected and thereby improving the contrast, thus reducing distortion, in an image obtained by the detection of secondary electrons from said surface of the object to be inspected.

Yet another object of the present invention is to provide a device manufacturing method in which a sample in the course of processes is evaluated by using such an imaging apparatus as described above.

There has also been one such prior art defect inspection apparatus used conventionally in a semiconductor manufacturing process or the like, which inspects a sample such as a wafer or the like for any defects by detecting secondary electrons emanated by irradiating a primary electron beam onto the sample.

Japanese patent Application Public Disclosure No. 11-132975, for example, discloses a defect inspection apparatus which comprises: an electron beam irradiating section for irradiating an electron beam against a sample; a projecting optical section for image-forming a one-dimensional and/or a two-dimensional image of secondary or reflected electrons, said secondary electrons being emanated in response to shape, material, and variation in potential on the surface of the sample; an electron beam detecting section for outputting a detection signal based on a formed image; an image display section for receiving said detection signal and displaying an electron image of the surface of the sample based thereon; and an electron beam deflecting section for changing the angle of incidence of the electron beam irradiated from the electron beam irradiating section onto the sample and the angle of intake of the secondary or reflected electrons into the projecting optical section. According to this inspection apparatus, the primary electron beam is irradiated onto a surface in a specified rectangular region of the sample wafer of the real device.

However, if the electron beam is irradiated on the surface in a relatively large area of the sample wafer of the real device, due to the sample surface being made of an insulating material such as silicon dioxide or silicon nitride, the electron beam irradiation against the sample surface and associated emanation of secondary electrons from the sample surface causes the sample surface to be positively charged, and an electric field produced by this potential has problematically caused a variety of image disorders in the secondary electron beam image.

The present invention has been made in the light of above-mentioned facts, and an object thereof is to provide an defect inspection apparatus and a defect inspection method that enable an inspection of a sample to be performed with higher accuracy by reducing positive charge builed-up in the surface of the sample, thereby overcoming the problem of disorder associated with this charge-up.

Another object of the present invention is to provide a semiconductor manufacturing method that can improve the yield of devices and prevent delivery of any defective products to market by using an inspection apparatus described above to carry out a defect inspection of a sample.

Further, a stage for accurately positioning a sample in a vacuum atmosphere has been used in an apparatus in which a charged particles beam such as an electron beam is irradiated onto the surface of a sample such as a semiconductor wafer so as to expose the surface of the sample to a pattern of a semiconductor circuit or the like, or so as to inspect a pattern formed on the surface of the sample, or in another apparatus in which the charged particles beam is irradiated onto the sample so as to apply an ultra-precise processing thereto.

When said stage is required to be positioned highly accurately, one structure has been conventionally employed, in which the stage is supported in non-contact manner by a hydrostatic bearing. In this case, the vacuum level in a vacuum chamber is maintained by forming a differential exhausting mechanism for exhausting a high pressure gas in an area of the hydrostatic bearing so that the high pressure gas supplied from the hydrostatic bearing may not be directly exhausted into the vacuum chamber.

FIGS. 55A-55B shows one of the examples of such a stage according to the prior art. In the configuration of FIG. 55A, the tip portion of an optical column 71 or a charged particles beam irradiating section 72 of a charged particles beam apparatus for emitting and irradiating a charged particles beam against a sample is attached to a housing 98 which makes up a vacuum chamber C. The interior of the optical column is exhausted to vacuum through a vacuum pipe 710, as in the chamber C through a vacuum pipe 911. Herein, the charged particles beam is irradiated from the tip portion 72 of the optical column 71 against a sample W such as a wafer or the like placed thereunder.

The sample W is detachably held on a sample table 94, and the sample table 94 is mounted on the upper face of a Y directionally movable unit 95 of an XY stage (hereafter referred to as a stage for simplicity). The above Y directionally movable unit 95 is equipped with a plurality of hydrostatic bearings 90 attached on planes (on both of the right and left faces and also on a bottom face in FIG. 55A) facing to guide planes 96a of an X directionally movable unit 96 of the stage 93, and is allowed to move in the Y direction (lateral direction in FIG. 55B) with a micro gap maintained between the guide planes and itself by said hydrostatic bearings 90. Further, a differential exhausting mechanism is provided surrounding the hydrostatic bearing so that a high-pressure gas supplied to the hydrostatic bearing does not leak into the vacuum chamber C. This is shown in FIG. 56. Doubled grooves 918 and 917 are formed surrounding the hydrostatic bearings 90, and are regularly exhausted to vacuum through a vacuum pipe by a vacuum pump (not shown). Owing to such structure, the Y directionally movable unit 95 is allowed to move freely in the Y direction in the vacuum atmosphere as supported in the non-contact manner. Those doubled grooves 918 and 917 are formed in a plane of the movable unit 95 in which the hydrostatic bearing 90 is arranged, so as to circumscribe said hydrostatic bearing. The structure of the hydrostatic bearing may be any of those conventionally known and its detailed explanation can be omitted here.

The X directionally movable unit 96 having said Y directionally movable unit 95 loaded thereon is formed to be concave in shape with the top face opened, as obviously seen from FIG. 55A, and said X directionally movable unit 95 is also provided with completely similar hydrostatic bearings and grooves, and further the unit 96 is supported in a non-contact manner with respect to the stage 97 so as to be movable freely in the X direction.

Combining said Y directionally movable unit 95 with the X directionally movable unit 96 allows the sample W to be moved to a desired position in the horizontal direction relative to the tip portion of the optical column or the charged particles beam irradiating section 72, so that the charged particles beam can be irradiated to a desired location of the sample.

With the stage including a combination of the hydrostatic bearing and the differential exhausting mechanism as described above, the guide plane 96a or 97a facing the hydrostatic bearing 90 makes a reciprocating motion between a high-pressure atmosphere in the electrostatic bearing portion and a vacuum environment within the chamber while the stage moves. During this reciprocating motion, such gas supply cycle is repeated in which while the guide plane is exposed to the high-pressure atmosphere, the gas is adsorbed onto the guide plane, and upon being exposed to the vacuum environment, the adsorbed gas is desorbed into the environment. Because of this gas supply cycle, every time when the stage moves, it has happened that the vacuum level in the chamber C is lowered, which has caused such problems that the exposure, inspection, or processing with the charged particles beam described above could not be carried out stably, and the sample might be contaminated.

Therefore, an another object of the present invention is to provide a charged particles beam apparatus capable of preventing the degradation of the vacuum level and thereby allow a process such as inspection or processing by a charged particles beam to be carried out stably.

Another object of the present invention is to provide a charged particles beam apparatus having a non-contact supporting mechanism by means of a hydrostatic bearing and a vacuum sealing mechanism by means of a differential exhausting so as to produce a pressure difference between the charged particles beam irradiating region and a supporting section of the hydrostatic bearing.

Still another object of the present invention is to provide a charged particles beam apparatus capable of reducing a gas desorbed from the surface of a part facing to the hydrostatic bearing.

Still another object of the present invention is to provide a defect inspection apparatus for inspecting the surface of a sample or an exposure apparatus for delineating a pattern on a surface of a sample, by using such a charged particles beam apparatus as described above.

Yet another object of the present invention is to provide a semiconductor manufacturing method for manufacturing a semiconductor device by using a charged particles beam apparatus such as described above.

Also, in the conventional stage including a combination of the hydrostatic bearing and the differential exhausting mechanism shown in FIGS. 55A-55B, there have been such problems that because of the differential exhausting mechanism having been added, the structure has become more complicated and its reliability as a stage has decreased while its cost has increased over that of a stage having a hydrostatic bearing used in the atmospheric pressure.

Therefore, another object of the present invention is to provide a charged particles beam apparatus having a simple structure capable of being made compact without employing a differential exhausting mechanism for the XY stage.

Another object of the present invention is to provide a charged particles beam apparatus with a differential exhausting mechanism for exhausting a region on a surface of a sample to which a charged particles beam is to be irradiated, as well as for exhausting the inside of a housing containing an XY stage to vacuum.

Still another object of the present invention is to provide a defect inspection apparatus for inspecting the surface of a sample for defects or an exposing apparatus for delineating a pattern on the surface of the sample by using either of the charged particles beam apparatuses described above.

Yet another object of the present invention is to provide a method for manufacturing a semiconductor device by using either of the charged particles beam apparatuses described above.

Also, as stated above, there has been used in the semiconductor manufacturing processes or the like a defect inspection apparatus for inspecting a sample such as a semiconductor wafer for defects by detecting secondary electrons emitted upon an irradiation of a primary electrons against said sample.

In such defect inspection apparatus, there has been employed a technology in which an image recognition technique is put into practical use to accomplish an automated inspection and to achieve higher efficiency in the inspection. In this technology, a computer carries out a matching operation between pattern image data for a region to be inspected in the sample surface obtained by detecting the secondary electrons and reference image data for the sample surface stored in advance, so that it is automatically determined if there are any defects existing in the sample, based on the operation results.

Recently, especially in the semiconductor manufacturing field, patterns are increasingly miniaturized, and consequently requiring detection of finer defects with high precision and efficiency. Under such condition, even the defect inspection apparatus taking advantage of the image recognition technique described above must further improve its recognition accuracy.

However, there has been such a problem associated with the prior art described above, which is that a position mismatch occurs between the image of the secondary electron beam obtained upon irradiating the primary electron beam against the region to be inspected in the sample surface and the reference image prepared in advance, which decreases the accuracy in defect detection. This position mismatch becomes a serious problem especially when the irradiation region of the primary electron beam is offset to the wafer resulting in the inspection pattern partially being out of the detection image of the secondary electron beam, which could not be handled only with the technology for optimizing a matching region within the detection image. This problem could be a fatal drawback especially in the inspecting of patterns of high precision.

Therefore, a still further object of the present invention is to provide a defect inspection apparatus which can prevent a loss of accuracy in the defect detection possibly caused by a position mismatch between the image of an inspection sample and a reference image.

Another object of the present invention is to provide a semiconductor manufacturing method used in semiconductor device manufacturing processes, which attempts to improve the yield of devices and to prevent any faulty products from being delivered to market by using a defect inspection apparatus as described above for performing a defect detection of a sample.

Means to Solve the Problem

The present invention has employed a method referred to as a projecting method using an electron beam as a means for improving the inspection rate which has been essential drawback of the SEM method. The projecting method will now be described below.

In the projecting method, an observation region on a sample is irradiated in block by a primary electron beam (i.e., no scanning but an irradiation covering a certain area), and secondary electrons emanated from the irradiated region are formed into an image in block by a lens system on a detector (a micro-channel plate plus fluorescent screen) as an image of electron beam. That image is used in a two-dimensional CCD (charge coupled device) or a TDI-CCD (a line image sensor) to convert the image data into an electric signal, which is then output onto a CRT or stored in some storage medium. From this image data, defects in the sample wafer (the semiconductor (Si) wafer being processed) may be detected. In the case of the CCD, the moving direction of the stage extends along the shorter axis (it may be along the longer axis), and the movement is made by the step and repeat manner. As for the stage movement in the case of TDI-CCD, the stage is continuously moved in the accumulation direction. Since the TDI-CCD allows the image to be serially obtained, the TDI-CCD may be used when the defect inspections are to be continuously carried out. The resolution is determined depending on the magnification and accuracy of an image-forming optical system (a secondary optical system), and in an embodiment, a resolution of 0.05 .mu.m has been obtained. In this example, with a resolution of 0.1 .mu.m and the electron beam irradiation condition of 1.6 .mu.A for the area of 200 .mu.m.times.50 .mu.m, an inspection time of about one hour per 20 cm wafer has been accomplished, which is 8 times higher than in the SEM method. The specification of the TDI-CCD employed herein has 2048 pixels.times.512 arrays with a line rate of 3.3 .mu.s (at line frequency of 300 kHz). In this example, although an irradiation area is determined so as to conform to the specification of the TDI-CCD employed, the irradiation area may be changed depending on the object to be irradiated.

Problems in this projecting method are; (1) a charge build-up is more likely to occur in the surface of a sample due to an in-block irradiation of electron beam; and (2) an electron current obtained by this method is limited (up to about 1.6 .mu.A), which prohibits any improvement in inspection rate.

Now, in order to dissolve the above mentioned problems of the conventional techniques, according to 1.sup.st aspect of the present invention, there is provided an inspection apparatus for inspecting an object to be inspected by irradiating either of a charged particles or an electromagnetic waves onto said object, said apparatus comprising:

a working chamber for inspecting said object, said chamber capable of being controlled to be vacuum atmosphere;

a beam generating means for generating either of said charged particles or said electromagnetic waves as a beam;

an electronic optical system for guiding and irradiating said beam onto said object to be inspected held in said working chamber, detecting a secondary charged particles emanated from said object to be inspected and introducing said secondary charged particles to an image processing system;

said image processing system for forming an image by said secondary charged particles;

an information processing system for displaying and/or storing the status information of said object to be inspected based on output from said image processing system; and a stage unit for operatively holding said object to be inspected so as to be movable with respect to said beam.

According to 2.sup.nd aspect of the present invention, in the inspection apparatus of 1.sup.st aspect, the inspection apparatus further comprises a carrying mechanism for securely accommodating said object to be inspected and for transferring said object to or from said working chamber.

According to 3.sup.rd aspect of the present invention, in the inspection apparatus of 2.sup.nd aspect, said carrying mechanism comprises;

a mini-environment chamber for supplying a clean gas to said object to be inspected to prevent dust from contacting said object to be inspected;

at least two loading chambers disposed between said mini-environment chamber and said working chamber, and adapted to be independently controllable so as to be a vacuum atmosphere; and a loader having a carrier unit capable of transferring said object to be inspected between said mini-environment chamber and said loading chambers, and another carrier unit capable of transferring said object to be inspected between said one loading chamber and said stage device;

wherein said working chamber and said loading chamber are supported through a vibration isolator.

According to 4.sup.th aspect of the present invention, in the inspection apparatus of 1.sup.st aspect, said inspection apparatus further comprising:

a precharge unit for irradiating a charged particle beam to said object to be inspected placed in said working chamber to reduce variations in charge on said object to be inspected; and a potential applying mechanism for applying a potential to said object to be inspected.

According to 5.sup.th aspect of the present invention, in the inspection apparatus of 3.sup.rd aspect, said loader includes:

a first loading chamber and a second loading chamber capable of independently controlling an atmosphere therein;

a first carrier unit for carrying said object to be inspected between said first loading chamber and the outside of said first loading chamber; and a second carrier unit disposed in said second loading chamber for carrying said object to be inspected between said first loading chamber and said stage device.

According to 6.sup.th aspect of the present invention, in the inspection apparatus of 1.sup.st, 2.sup.nd or 3.sup.rd aspect, the inspection apparatus further comprises:

an alignment controller for observing the surface of said object to be inspected for an alignment of said object to be inspected with respect to said electron-optical system to control the alignment; and a laser interference range finder for detecting coordinates of said object to be inspected on said stage device, said coordinates of said object to be inspected being determined by said alignment controller using patterns formed on said object to be inspected.

According to 7.sup.th aspect of the present invention, in the inspection apparatus of 1.sup.st, 2.sup.nd or 3.sup.rd aspect, the alignment of said object to be inspected includes:

rough alignment performed within said mini-environment space; and alignment in XY-directions and alignment in a rotating direction performed on said stage device.

According to b 8.sup.th aspect of the present invention, in the inspection apparatus of 1.sup.st, 2.sup.nd or 3.sup.rd aspect, said electron optical system includes:

an E.times.B separator for deflecting said secondary charged particle toward said detector by a field where an electric field and a magnetic field cross at right angles; and an electrode for controlling an electric field intensity in a plane of said sample to be inspected, said plane being exposed to said electron beam irradiation, said electrode being arranged between said objective lens and said sample to be inspected and having a shape approximately symmetrical with respect to the optical axis of irradiation of said beam.

According to 9.sup.th aspect of the present invention, in the inspection apparatus of 1.sup.st, 2.sup.nd or 3.sup.rd aspect, said apparatus includes an E.times.B separator, to which said charged particle and said secondary charged particle are entered, said secondary charged particle being advanced in the direction approximately opposite to said charged particle, and in which said charged particle or said secondary charged particle is deflected selectively, said E.times.B separator characterized in that: an electrode for generating an electric field is made up of three or more pairs of non-magnetic conductive electrodes, and is arranged so as to approximately form a cylinder.

According to 10.sup.th aspect of the present invention, in the inspection apparatus of 1.sup.st, 2.sup.nd or 3.sup.rd aspect, said apparatus further comprises a charged particle irradiating section for irradiating charged particles in advance against said inspecting region just before the inspection.

According to 11.sup.th aspect of the present invention, in the inspection apparatus of 1.sup.st, 2.sup.nd or 3.sup.rd aspect, said apparatus further comprising a means for making the distribution uniform or reducing the potential level of electric charge residing on said object.

According to 12.sup.th aspect of the present invention, in the inspection apparatus of 1.sup.st, 2.sup.nd or 3.sup.rd aspect, electrons having energy lower than that of said charged particles are supplied to said sample at least during said detector detecting said secondary charged particle image.

According to 13.sup.th aspect of the present invention, in the inspection apparatus of 1.sup.st, 2.sup.nd or 3.sup.rd aspect, said stage is an XY stage, which is accommodated in a working chamber and supported by a hydrostatic bearing in a non-contact manner with respect to said working chamber;

said working chamber in which said stage is accommodated is exhausted to vacuum; and a differential exhausting mechanism is arranged surrounding a portion in said charged particle beam apparatus, where the charged particle beam is to be irradiated against a surface of said sample, so that a region on said sample to which said charged particle beam is to be irradiated may be exhausted to vacuum.

According to 14.sup.th aspect of the present invention, in the inspection apparatus of 1.sup.st, 2.sup.nd or 3.sup.rd aspect, said apparatus includes an apparatus for irradiating a charged particle beam against a surface of a sample loaded on an XY stage while moving said sample to a desired position in a vacuum atmosphere, said XY stage is provided with a non-contact supporting mechanism by means of a hydrostatic bearing and a vacuum sealing mechanism by means of differential exhausting, and a divider is provided for making the conductance smaller between a charged particle beam irradiating region and a hydrostatic bearing support section, so that there is a pressure difference to be produced between said charged particle beam irradiating region and said hydrostatic bearing support section.

According to 15.sup.th aspect of the present invention, in the inspection apparatus of 1.sup.st, 2.sup.nd or 3.sup.rd aspect, said apparatus includes;

an image obtaining means for obtaining respective images for a plurality of regions to be inspected, said regions being displaced from one another while being partially superimposed one on another on said sample;

a storage means for storing a reference image; and a defect determination means for determining any defects in said sample by comparing said respective images obtained by said image obtaining means for said plurality of regions to be inspected with said reference images stored in said storage means.

According to 16.sup.th aspect of the present invention, there is provided a device manufacturing method, which comprises the step of:

detecting defects on a wafer using an inspection apparatus according to anyone of 1.sup.st to 15.sup.th aspect in the middle of a process or subsequent to the process.

According to 1.sup.st to 16.sup.th aspects of the present invention, the following advantages are provided:

(A) the general configuration can be established for an inspection apparatus in accordance with a charged particle based projection scheme, which can process objects under inspecting at a high throughput;

(B) a clean gas is forced to flow to an object to be inspected within the mini-environment space to prevent dust from attaching to the object to be inspected, and a sensor is provided for observing the cleanliness, thereby making it possible to inspect the object to be inspected while monitoring dust within the space;

(C) when the loading chamber and the working chamber are integrally supported through a vibration isolator, an object to be inspected can be carried to the stage device and inspected thereon without being affected by the external environment; and (D) when the precharge unit is provided, a wafer made of an insulating material will not be affected by charging.

According to 17.sup.th aspect of the present invention, there is provided an inspection apparatus which comprises:

a beam source for irradiating a charged particle against a sample to be inspected;

a retarding-field type objective lens for decelerating said charged particle as well as for accelerating secondary charged particle generated by said electron beam irradiated against said sample to be inspected;

a detector for detecting said secondary charged particle;

an E.times.B deflecting system for deflecting said secondary charged particle toward said detector by a field where an electric field and a magnetic field cross at right angles; and an electrode for controlling the electric field intensity in a plane of said sample to be inspected, said plane being exposed to said charged particle irradiation, said electrode being arranged between said retarding-field type objective lens and said sample to be inspected and having a shape approximately symmetrical with respect to an optical axis of irradiation of said charged particles.

According to 18.sup.th aspect of the present invention, in the electron beam apparatus of 17.sup.th aspect, a voltage applied to said electrode is controlled in order to control said electric field intensity depending on a category of said sample to be inspected.

According to 19.sup.th aspect of the present invention, in the electron beam apparatus of 17.sup.th aspect, said sample to be inspected is a semiconductor wafer, and said voltage applied to said electrode in order to control said electric field intensity is controlled depending on whether or not said semiconductor device has a via.

According to 20.sup.th aspect of the present invention, there is provided a device manufacturing method which uses an electron beam apparatus defined by either of 17.sup.th to 19.sup.th aspect, wherein said method is characterized in that a semiconductor wafer, which has been prepared as said sample to be inspected, is inspected for defects by using said inspecting apparatus in a manufacturing process of the device or subsequent to the process.

According to 17.sup.th to 20.sup.th aspect of the present invention, the following advantages are provided.

Since the electrode having a shape approximately symmetrical with respect to the axis of irradiation of the charged particles has been arranged between the sample to be inspected and the objective lens so as to control the electric field intensity in the charged particle irradiated plane of the sample to be inspected, therefore the electric field between the sample to be inspected and the objective lens can be controlled.

Further, since the electrode having a shape approximately symmetrical with respect to the axis of irradiation of the charged particle has been arranged between the sample to be inspected and the objective lens so as to weaken the electric field intensity in the charged particle irradiated plane of the sample to be inspected, therefore the electric discharge between the sample to be inspected and the objective lens can be eliminated.

Since there has been no modification such as decreasing the voltage applied to the objective lens and therefore the secondary charged particles can go through the objective lens efficiently, thus a detection efficiency can be improved and a signal with good S/N ratio can be obtained.

Further, the voltage can be controlled so as to weaken the electric field intensity in the charged particle irradiated plane of the sample to be inspected, depending on the type of sample to be inspected.

For example, if the sample to be inspected is of a type that is likely to cause an electric discharge between the objective lens and itself, the electric discharge can be prevented by weakening the electric field intensity in the charged particle irradiated plane of the sample to be inspected by changing the voltage applied to the electrode.

Further, the voltage applied to the electrode can be changed depending on whether or not said semiconductor device has a via, that is, the voltage applied in order to weaken the electric field intensity in the charged particle irradiated plane of the semiconductor wafer can be changed.

For example, if the sample to be inspected is of a type that is likely to cause an electric discharge between the objective lens and itself, the electric discharge especially in the via or in the vicinity of the via can be prevented by changing the electric field caused by the electrodes and thereby weakening the electric field intensity in the charged particle irradiated plane of the sample to be inspected.

Further, since an electric discharge is prevented between the via and the objective lens, there would be no damage to the pattern or the like in the semiconductor wafer, which otherwise would be caused by the electric discharge.

Further, since the potential applied to the electrode has been made lower than that applied to the sample to be inspected, therefore the electric field intensity in the charged particle irradiated plane of the sample to be inspected can be weakened, thus preventing the electric discharge to the sample to be inspected.

Yet further, since the potential applied to said electrode is negative and the sample to be inspected has been grounded, the electric field intensity is weakened in the charged particle irradiated plane of the sample to be inspected, to prevent an electric discharge to the sample to be inspected.

According to 21.sup.st aspect of the present invention, there is provided an E.times.B separator, into which a first charged particle beam and a second charged particle beam enter, said second charged particles being advanced in the direction approximately opposite to said first charged particle beam, and in which said first charged particle beam or said second charged particle beam is deflected selectively, said E.times.B separator characterized in that:

an electrode for generating an electric field is made up of three or more pairs of non-magnetic conductive electrodes, and is arranged so as to form cylinder.

According to 22.sup.nd aspect of the present invention, in the E.times.B separator of 21.sup.st aspect, each of a pair of parallel plate magnetic poles for generating a magnetic field is respectively arranged outside of said cylinder composed of said three or more pairs of non-magnetic conductive electrodes, and projections are formed in peripheral portions of the opposite face of each of said pair of parallel plate magnetic poles.

According to 23.sup.rd aspect of the present invention, in the E.times.B separator of 22.sup.nd aspect, in a passage space of lines of magnetic force of the magnetic field generated, a majority of the passage space other than that between said parallel plate magnetic poles is formed to be cylindrical shape coaxial with said cylinder composed of said three or more pairs of non-magnetic conductive electrodes.

According to 24.sup.th aspect of the present invention, in the E.times.B separator of 22.sup.nd or 23.sup.rd aspect, said parallel plate magnetic poles are made of permanent magnets.

According to 25.sup.th aspect of the present invention, in the defect inspection apparatus using the E.times.B separator defined by either of 21.sup.st to 24.sup.th aspect, either one of said first charged particle beam or said second charged particle beam is a primary charged particle beam to be irradiated against a sample to be inspected, and the other is a secondary charged particle beam generated from said sample by the irradiation of said primary charged particle beam.

According to 21.sup.st to 25.sup.th aspect of the present invention, the following advantages are provided.

Both of the electric field and the magnetic field are allowed to emerge uniformly in the larger region around the optical axis, so that even if the area exposed to the irradiation of the charged particle is extended, the aberration for the image passed through the E.times.B separator would fall into a reasonable range of values.

Since the projections have been arranged in the peripheral portions of the magnetic poles generating the magnetic field, and said magnetic poles are also arranged outside of the electrodes for generating the electric field, they allow a uniform magnetic field to be generated, reducing a distortion by the magnetic poles. Further, since the magnetic field has been generated by use of the permanent magnets, the E.times.B separator can be fully installed in vacuum. Still further, the electrodes for generating the electric field and the magnetic circuit for forming the magnetic path have been formed into coaxial cylindrical shapes centered to the optical axis, which makes it possible to reduce in size the E.times.B separator as a whole.

According to 26.sup.th aspect of the present invention, there is provided a projective type electron beam inspection apparatus, which comprises a charged particle irradiating section, a lens system, a deflecting system, an E.times.B filter (Wiener filter), and a secondary charged particle detector, in which charged particles from said charged particle irradiating section is irradiated onto an inspecting region of a sample through said lens system, said deflecting system, and said E.times.B filter, and secondary charged particles emitted from the sample are formed into an image in said secondary charged particle detector by said lens system, said deflecting system, and said E.times.B filter, and an electric signal thereof is inspected as the image, said apparatus characterized in further comprising a charged particle irradiating section for irradiating charged particles in advance against said inspecting region just before the inspection.

According to 27.sup.th aspect of the present invention, in the apparatus of 26.sup.th aspect, said charged particle is selected from the group consisting of electron, positive or negative ion, or plasma.

According to 28.sup.th aspect of the present invention, in the apparatus of 26.sup.th or 27.sup.th aspect, the energy of said charged particles is equal to or less than 100 eV.

According to 29.sup.th aspect of the present invention, in the apparatus of 26.sup.th or 27.sup.th aspect, the energy of said charged particles is not greater than 30 eV.

According to 30.sup.th aspect of the present invention, there is provided a device manufacturing method using an inspection apparatus defined by either of 26.sup.th to 29.sup.th aspect, wherein a pattern inspection is performed in the device manufacturing processes.

According to 26.sup.th to 30.sup.th aspect of the present invention, the following advantages are provided.

Since a pre-treatment by means of a charged particle irradiation is employed just before a measurement, an evaluated image distortion by the charging would not occur or could be negligible, therefore all defects can be accurately detected.

Further, since a high current can be used for scanning a stage by such an amount that has caused a problem in the prior art, a large amount of secondary electrons can be detected and a detection signal having a good S/N ratio can be obtained, thus reliability of the defect detection.

Still further, with a larger S/N ratio, faster scanning of the stage can still produce good image data, thus improving inspection throughput.

According to 31.sup.st aspect of the present invention, there is provided an imaging apparatus which irradiates a charged particle beam emitted from a beam source against an object and detects a secondary charged particle emanated from the object by using a detector so as to collect an image data of said object, to inspect the object for defects and so forth, said apparatus characterized in further comprising a means for making the distribution uniform or reducing the potential level of electric charge residing on said object.

According to 32.sup.nd aspect of the present invention, in the imaging apparatus of 31.sup.st aspect, said means comprises an electrode disposed between said beam source and said object so as to be capable of controlling said electric charge.

According to 33.sup.rd aspect of the present invention, in the imaging apparatus of 31.sup.st aspect, said means is designed so as to operate during the idle time between measurement timings.

According to 34.sup.th aspect of the present invention, in the imaging apparatus of 31.sup.st aspect, said imaging apparatus further comprises:

at least one or more primary optical systems for irradiating a plurality of charged particle beams against said object; and at least one or more secondary optical systems for guiding electrons emanating from said object to at least one or more detectors, wherein each of said plurality of primary charged particle beams is respectively irradiated onto a spot such that the distance between any two spots is greater than the distance resolution of said secondary optical system.

According to 35.sup.th aspect of the present invention, there is provided a device manufacturing method characterized in that a defect in a wafer is detected in the course of processing by using the imaging apparatus disclosed in either of 31.sup.st to 34.sup.th aspects.

According to the invention of 31.sup.st to 35.sup.th aspects, the following effects may be expected to obtain.

(A) Distortion in an image caused by electric charging may be reduced regardless of the properties of the object to be inspected.

(B) Since the idle time between the timings for the conventional measurement is used to offset the electric charging and make it uniform, there would be no affect on throughput.

(C) Since real-time processing becomes possible, time for any post-processing, a memory and the like are no more necessary.

(D) A fast and highly accurate observation of an image and detection of a defect may be accomplished.

According to 36.sup.th aspect of the present invention, there is provided an inspection apparatus for inspecting a sample for defects, comprising: a charged particle irradiation means capable of irradiating primary charged particles against said sample; a projecting means for projecting secondary charged particles emanating from said sample by the irradiation of said primary charged particles so as to form an image; a detection means for detecting an image formed by said projecting means as an electron image of said sample; and a defect evaluation means for determining a defect in said sample based on an electron image detected by said detection means, said apparatus characterized in that electrons having energy lower than that of said irradiated primary charged particle are supplied to said sample at least during said detection means detecting said electron image.

In the 36.sup.th aspect of the present invention, the charged particle irradiation means irradiates primary charged particles against the sample, and the projecting means projects the secondary charged particle emanating from the sample in response to the irradiation of the primary charged particles so as to form the image in the detection means. The sample, which has emitted out the secondary charged particle therefrom, is charged up to a positive potential. The detection means detects the formed image as the electron image of the sample, and the defect evaluation means determines whether any defects exist in the sample based on the detected electron image. In that case, at least during the time period when the detection means is detecting the electron image, electrons having energy lower than that of the irradiated primary charged particles is supplied to the sample. Those electrons of lower energy may neutralize the sample that has been positively charged-up by an emanation of the secondary charged particle gone from the sample. This allows the secondary charged particle to be formed into an image without any substantial effect from the positive potential of the sample, and thereby the detection means can detect the electron image with the reduced image distortion.

As for electrons having energy lower than that of the primary charged particle, preferably, for example, UV photoelectrons may be used. The UV photoelectron is defined as an electron emanated from a substance such as metal or the like by the photoelectric effect upon irradiation of a beam of light including ultra-violet ray (UV) to said substance. Alternatively, any means other than the charged particle irradiation means, for example, an electron gun or the like may be used to generate electrons having the energy lower than that of the primary charged particle.

It is to be noted that those secondary charged particles which have emanated from the sample by the irradiation of the primary charged particles may include some reflected electrons generated by the primary charged particle which have been reflected from the sample surface in addition to the secondary electrons originated from those electrons which were once in the sample but which have emanated from the surface thereof by the impingement of the primary charged particle thereto. It is apparent that the electron image to be formed by the detection means of the present invention also includes a contribution from those back scattered electrons.

According to 37.sup.th aspect of the present invention, there is provided a defect inspection apparatus for inspecting a sample for any defects, comprising: a charged particle irradiation means capable of irradiating a primary charged particle against said sample; a projecting means for projecting a secondary charged particle emanated from said sample by the irradiation of said primary charged particle so as to form an image; a detection means for detecting an image formed by said projecting means as an electron image of said sample; and a defect evaluation means for determining a defect in said sample based on the electron image detected by said detection means, said apparatus characterized in further comprising a UV photoelectron supply means capable of supplying a UV photoelectron to said sample.

In the 37.sup.th aspect of the present invention, so far as the reduction in image disorder can be accomplished effectively according to the present invention by the UV photoelectron supply means (or in the UV photoelectron supply), the low energy electrons can be supplied to the sample with arbitrary timing and for arbitrary duration. For example, the supply of UV photoelectrons may be started before the primary charged particles are irradiated, before the secondary charged particles are formed into an image, or after the secondary charged particles have been formed into an image but before the electron image is detected. Further, as in the first aspect, the UV photoelectron supply may continue at least while the secondary charged particle is being detected, but the supply of UV photoelectrons may be stopped even before or during the electron image detection if the sample has been electrically neutralized sufficiently.

According to 38.sup.th aspect of the present invention, there is provided a defect inspection method for inspecting a sample for any defects, which comprises: an irradiating process for irradiating primary charged particles against said sample; a projecting process for projecting secondary charged particles emanated from said sample by the irradiation of said primary charged particle so as to form an image; a detecting process for detecting said image formed in said projecting process as an electron image of said sample; and a defect evaluating process for determining a defect in said sample based on said electron image detected in said detecting process, wherein electrons having energy lower than that of said primary charged particles are supplied to said sample at least during said electron image being detected in said detecting process.

According to 39.sup.th aspect of the present invention, there is provided a defect inspection method for inspecting a sample for any defects, which comprises: an irradiating process for irradiating primary charged particles against said sample; a projecting process for projecting secondary charged particles emanated from said sample by the irradiation of said primary charged particles so as to form an image; a detecting process for detecting said image formed in said projecting process as an electron image of said sample; and a defect evaluating process for determining a defect in said sample based on said electron image detected in said detecting process, said method further comprising: a UV photoelectron supplying process for supplying said sample with UV photoelectrons.

According to 40.sup.th aspect of the present invention, there is provided a semiconductor manufacturing method which includes a process for inspecting for any defects a sample to be required in manufacturing a semiconductor device by using a defect inspection apparatus of 36.sup.th or 37.sup.th aspect.

According to the invention of 36.sup.th to 40.sup.th aspects, the following advantages can be expected.

Since electrons having energy lower than that of the primary charged particles are supplied to the sample to be inspected, positive charge-up of the surface of the sample possibly caused by the secondary charged particle emanation may be reduced, and thereby an image distortion of the secondary charged particle resulting from the charging may be also resolved, and the sample may be inspected for defects with high accuracy.

Further, when the defect inspection is conducted by using such a defect inspection apparatus as described above, the yield of the product can be improved and the delivery of defective products can also be prevented.

According to 41.sup.st aspect of the present invention, there is provided an apparatus for irradiating a charged particle beam against the surface of a sample loaded on an XY stage while moving said sample to a desired position in vacuum atmosphere, said apparatus characterized in that:

said XY stage is provided with a non-contact supporting mechanism by means of a hydrostatic bearing and a vacuum sealing mechanism by means of differential exhausting, and a divider is provided for reducing the conductance between the charged particle beam irradiating region and a hydrostatic bearing support section, so that there is a pressure difference produced between said charged particle beam irradiating region and said hydrostatic bearing support section.

According to 42.sup.nd aspect of the present invention, in the charged particle beam apparatus of 41.sup.st aspect, said divider has a differential exhausting structure integrated therein.

According to 43.sup.rd aspect of the present invention, in the charged particle beam apparatus of 41.sup.st or 42.sup.nd aspect, said divider has a cold trap function.

According to 44.sup.th aspect of the present invention, in the charged particle beam apparatus of either 41.sup.st to 43.sup.rd aspect, said dividers are arranged in two locations including a proximity of the charged particle beam irradiating location and a proximity of the hydrostatic bearing.

According to 45.sup.th aspect of the present invention, in the charged particle beam apparatus either of 41.sup.st to 44.sup.th aspects, the gas supplied to the hydrostatic bearing of said stage is either nitrogen or an inert gas.

According to 46.sup.th aspect of the present invention, in the charged particle beam apparatus either of 41.sup.st to 45.sup.th aspects, a surface treatment is applied to at least the part of the surface facing the hydrostatic bearing in said XY stage so as to reduce the amount of gas to be desorbed.

According to 47.sup.th aspect of the present invention, there is provided a wafer defect inspection apparatus for inspecting a surface of a wafer for defects by using the apparatus disclosed in either of 41.sup.st to 46.sup.th aspects.

According to 48.sup.th aspect of the present invention, there is provided an exposing apparatus for delineating a circuit pattern of a semiconductor device on a surface of a semiconductor wafer or a reticle by using the apparatus disclosed in any of 41.sup.st to 46.sup.th aspects.

According to 49.sup.th aspect of the present invention, there is provided a semiconductor manufacturing method for manufacturing a semiconductor by using the apparatus disclosed in any of 41.sup.st to 48.sup.th aspects.

According to 41.sup.st to 49.sup.th aspect of the present invention, the following effects may be expected to obtain.

(a) The stage device can enhance accurate positioning within vacuum atmosphere, and further, the pressure in the space surrounding the charged particle beam irradiating location is hardly increased. That is, it allows the charged particle beam processing to be applied to the sample with high accuracy.

(b) It is almost impossible for gas desorbed or leaked from the hydrostatic bearing to go though the divider and reach the space for the charged particle beam irradiating system. Thereby, the vacuum level in the space surrounding the charged particle beam irradiating location can be further stabilized.

(c) It is harder for the discharged gas to go through to the space for the charged particle beam irradiating system, and it is easier to maintain the stability of the vacuum level in the space surrounding the charged particles beam irradiating location.

(d) The interior of the vacuum chamber is partitioned into three chambers, i.e., a charged particle beam irradiation chamber, a hydrostatic bearing chamber and an intermediate chamber which communicate with each other via a small conductance. Further, the vacuum exhausting system is constructed to control the pressures in the respective chambers sequentially, so that the pressure in the charged particle beam irradiation chamber is the lowest, the intermediate chamber medium, and the hydrostatic bearing chamber the highest. The pressure fluctuation in the intermediate chamber can be reduced by the divider, and the pressure fluctuation in the charged particle beam irradiation chamber can be further reduced by another step of divider, so that the pressure fluctuation therein can be reduced substantially to a non-problematic level.

(e) The pressure increase upon movement of the stage can be controlled so that it is kept low.

(f) The pressure increase upon movement of the stage can be further controlled to be kept even lower.

(g) Since a defect inspection apparatus with highly accurate stage positioning performance and with a stable vacuum level in the charged particle beam irradiating region can be accomplished, an inspection apparatus with high inspection performance and without any fear of contamination of the sample can be provided.

(h) Since a defect inspection apparatus with highly accurate stage positioning performance and with a stable vacuum level in the charged particle beam irradiating region can be accomplished, an exposing apparatus with high exposing accuracy and without any fear of contamination of the sample can be provided.

(i) Manufacturing the semiconductor by using the apparatus with highly accurate stage positioning performance and with a stable vacuum level in the charged particle beam irradiating region can form a miniaturized micro semiconductor circuit.

According to 50.sup.th aspect of the present invention, there is provided an inspection apparatus or inspection method for inspecting a sample for any defect, which comprises;

an image obtaining means for obtaining respective images for a plurality of regions to be inspected, said regions being displaced from one another while being partially superimposed one on another on said sample;

a storage means for storing a reference image; and a defect determination means for determining any defects in said sample by comparing said respective images obtained by said image obtaining means for said plurality of regions to be inspected with said reference image stored in said storage means.

According to 51.sup.st aspect of the present invention, in the inspection apparatus or inspection method of 50.sup.th aspect, said apparatus further comprises a charged particle irradiation means for irradiating a primary charged particle beam against each of said plurality of regions to be inspected so that a secondary charged particle beam is emitted from said sample, wherein said image obtaining means obtains images of said plurality of regions to be inspected in order by detecting said secondary charged particle beam emitted from said plurality of regions to be inspected.

According to 52.sup.nd aspect of the present invention, in the inspection apparatus or inspection method of 51.sup.st aspect, said charged particle irradiation means comprises a particle source for emitting primary charged particles and a deflecting means for deflecting said primary charged particles, wherein said deflecting means deflects said primary charged particles emitted from said particle source so as to be irradiated against said plurality of regions to be inspected in order.

According to 53.sup.rd aspect of the present invention, in the inspection apparatus or inspection method either of 50.sup.th to 52.sup.nd aspects, said apparatus comprises a primary optical system for irradiating a primary charged particle beam against a sample and a secondary optical system for guiding secondary charged particles to a detector.

According to 54.sup.th aspect of the present invention, there is provided a semiconductor manufacturing method, which includes a process for inspecting a finished or an under processing of wafer for any defect by using an inspection apparatus either of 50.sup.th to 53.sup.rd aspects.

According to 50.sup.th to 54 the aspect of the present invention, the following advantages are provided.

Since the defect in the sample can be detected by first obtaining respective images of a plurality of regions to be inspected, which are displaced from one another while being partially superimposed one on another on the sample, and comparing those images of the regions to be inspected with the reference image, any deterioration in the accuracy in the defect detection can be prevented.

Further, according to the device manufacturing method of the invention, since the defect detection is performed by using such a defect inspection apparatus as described above, the yield of the products can be improved and the delivery of any faulty products can be prevented.

According to 55.sup.th aspect of the present invention, there is provided an apparatus for irradiating a charged particle beam against a sample loaded on an XY stage, said apparatus characterized in that: said XY stage is accommodated in a housing and supported by a hydrostatic bearing in a non-contact manner with respect to said housing; said housing in which said stage is accommodated is exhausted to vacuum; and a differential exhausting mechanism is arranged surrounding a portion in said charged particle beam apparatus, where the charged particle beam is to be irradiated against a surface of said sample, so that a region on said sample to which said charged particle beam is to be irradiated may be exhausted to vacuum.

According to this invention, a high-pressure gas supplied for the hydrostatic bearing and leaking into the vacuum chamber is primarily evacuated by a vacuum exhausting pipe connected to the vacuum chamber. Further, arranging the differential exhausting mechanism, which functions to exhaust the region to which the charged particle beam is to be irradiated, so as to surround the portion on which the charged particle beam is to be irradiated, allows the pressure in the irradiation region of the charged particles beam to be decreased to a significantly lower level than that in the vacuum chamber, thus achieving a stable vacuum level where the processing of the sample by the charged particle beam can be performed without any problems. That is to say, a stage with a structure similar to that of a stage of hydrostatic bearing type commonly used in the atmospheric pressure (a stage supported by the hydrostatic bearing having no differential exhausting mechanism) may be used to stably process the sample on the stage by the charged particle beam.

According to 56.sup.th aspect of the present invention, in the charged particles beam apparatus of 55.sup.th aspect, a gas to be supplied to said hydrostatic bearing of said XY stage is nitrogen or an inert gas, and said nitrogen or inert gas is pressurized after having been exhausted from said housing containing said stage so as to be supplied again to said hydrostatic bearing.

According to this invention, since the residual gas components in the vacuum housing are inert, there should be no fear that the surface of the sample or any surfaces of the structures within the vacuum chamber defined by the housing would be contaminated by water contents or oil and fat contents, and in addition, even if inert gas molecules are adsorbed onto the sample surface, once being exposed to the differential exhausting mechanism or the high vacuum section of the irradiation region of the charged particles beam, said inert gas molecules would be released immediately from the sample surface, so that the effect on the vacuum level in the irradiation region of the charged particle beam can be minimized and the processing applied by the charged particle beam to the sample can be stabilized.

According to 57.sup.th aspect of the present invention, there is provided a wafer defect inspection apparatus for inspecting a surface of a semiconductor wafer for defects by using the apparatus of 55.sup.th or 56.sup.th aspect.

This allows the provision of an inspection apparatus which accomplishes positioning performance of the stage with high precision and also provides a stable vacuum level in the irradiation region of the charged particles beam at low cost.

According to 58.sup.th aspect of the present invention, there is provided an exposing apparatus for delineating a circuit pattern of a semiconductor device on the surface of a semiconductor wafer or a reticle by using the apparatus of 55.sup.th or 56.sup.th aspect.

This allows the provision of an exposing apparatus which accomplishes positioning performance of the stage with high precision and also provides a stable vacuum level in the irradiation region of the charged particles beam at low cost.

According to 59.sup.th aspect of the present invention, there is provided a semiconductor manufacturing method for manufacturing a semiconductor by using the apparatus of either of 55.sup.th to 58.sup.th aspects.

This allows a micro semiconductor circuit to be formed by way of manufacturing a semiconductor with the apparatus which accomplishes positioning performance of the stage with high precision and also provides a stable vacuum level in the irradiation region of the charged particles beam.

According to the inventions of 55.sup.th to 59.sup.th aspects, the following effects may be expected to obtain.

(A) Processing by the charged particle beam can be stably applied to a sample on a stage by the use of the stage having a structure similar to that of a stage of hydrostatic bearing type which is typically used at atmospheric pressure (a stage supported by the hydrostatic bearing having no differential exhausting mechanism).

(B) The effect on the vacuum level in the charged particle beam irradiation region can be minimized, and thereby the processing by the charged particle beam to the sample can be stabilized.

(C) Such an inspection apparatus can be provided at low cost that accomplishes positioning performance of the stage with high precision and provides a stable vacuum level in the irradiation region of the charged particle beam.

(D) Such an exposing apparatus can be provided in low cost that accomplishes positioning performance of the stage with high precision and provides a stable vacuum level in the irradiation region of the charged particle beam.

(E) A micro semiconductor circuit can be formed by manufacturing the semiconductor using an apparatus which accomplishes positioning performance of the stage with high precision and provides a stable vacuum level in the irradiation region of the charged particle beam.

According to 60.sup.th aspect of the present invention, there is provided an inspection method for inspecting an object to be inspected by irradiating either of charged particles or electromagnetic waves onto said object to be inspected by using an apparatus which comprises:

a working chamber for inspecting said object to be inspected, said chamber capable of being controlled to be vacuum atmosphere;

a beam source for emitting either of said charged particle or said electromagnetic waves as a beam;

an electronic optical system for guiding and irradiating said beam onto said object to be inspected held in said working chamber, detecting a secondary charged particles emanated from said object to be inspected and introducing said secondary charged particles to an image processing system;

said image processing system for forming an image by said secondary charged particle;

an information processing system for displaying and/or storing status information of said object to be inspected based on an output from said image processing system; and a stage unit for operatively holding said object to be inspected so as to be movable with respect to said beam, wherein said method comprises the steps of:

positioning said beam accurately onto said object to be inspected by measuring the position of said object to be inspected;

deflecting said beam onto a desired position of said measured object to be inspected;

irradiating said desired position on a surface of said object to be inspected by said beam;

detecting a secondary charged particle emanating from said object to be inspected;

forming an image by said secondary charged particles; and displaying and/or storing status information of said object to be inspected based on output from said image processing system.

BRIEF DESCRIPTION OF THE DRAWINGS

FIGS. 5A and 5B are enlarged views of a wafer rack, wherein FIG. 5A is a side view, and FIG. 5B is a cross-sectional view taken along a line E-E in FIG. 5A;

FIGS. 28A-28C are a diagram for explaining specifically a method for inspecting a wafer for any defect in the defect inspection apparatus according to either of the embodiments shown in FIGS. 24 to 26, wherein FIG. 28A shows a pattern defect detection, FIG. 28B shows a line width measurement, and FIG. 28C shows a potential contrast measurement, respectively;

FIGS. 30A and 30B are diagrams for explaining an electron beam calibration mechanism, wherein FIG. 30A is a side view, and FIG. 30B is a plan view;

FIGS. 32A-32B are a sectional view of a vacuum chamber and an XY stage of a charged particles beam apparatus of an embodiment according to the present invention, wherein FIG. 32A is a front elevational view and FIG. 32B is a side elevational view;

FIG. 42 shows some examples of a plurality of images to be inspected which are obtained by the defect inspection apparatus of FIG. 41, and an example of a reference image;

FIGS. 55A-55B are sectional views of a vacuum chamber and an XY stage in a charged particles beam apparatus according to the prior art, wherein FIG. 55A is a front elevational view and FIG. 55B is a side elevational view.

BEST MODE FOR IMPLEMENTING THE INVENTION

In the following, preferred embodiments of the present invention will be described with reference to the accompanying drawings in connection with a semiconductor inspection apparatus for inspecting, as an object to be inspected, a substrate, i.e., a wafer which has patterns formed on the surface thereof.

Figure 1:
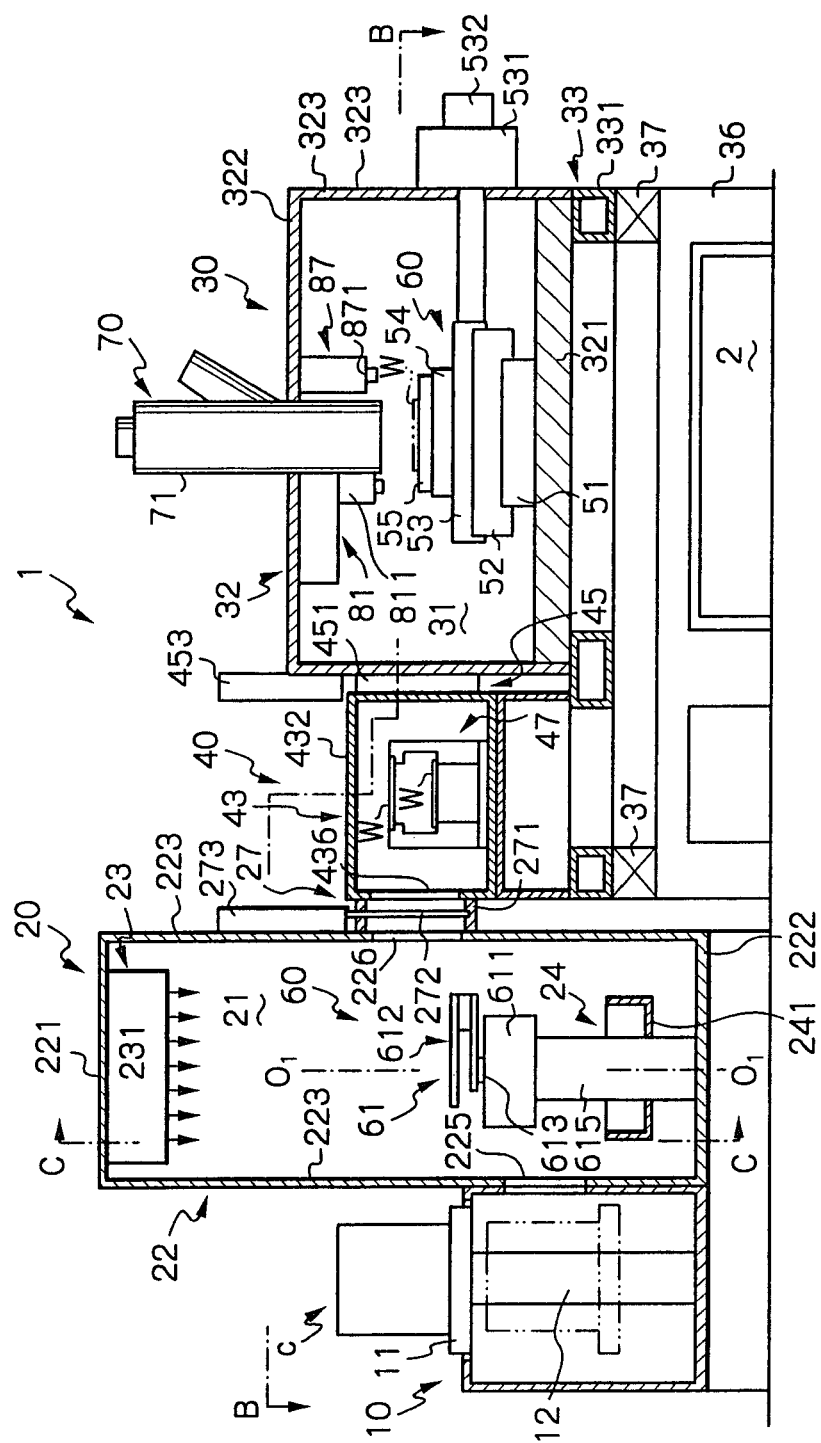
FIG. 1 is an elevation illustrating main components of an inspection apparatus according to the present invention, viewed along a line A-A in FIG. 2.
Figure 2A:
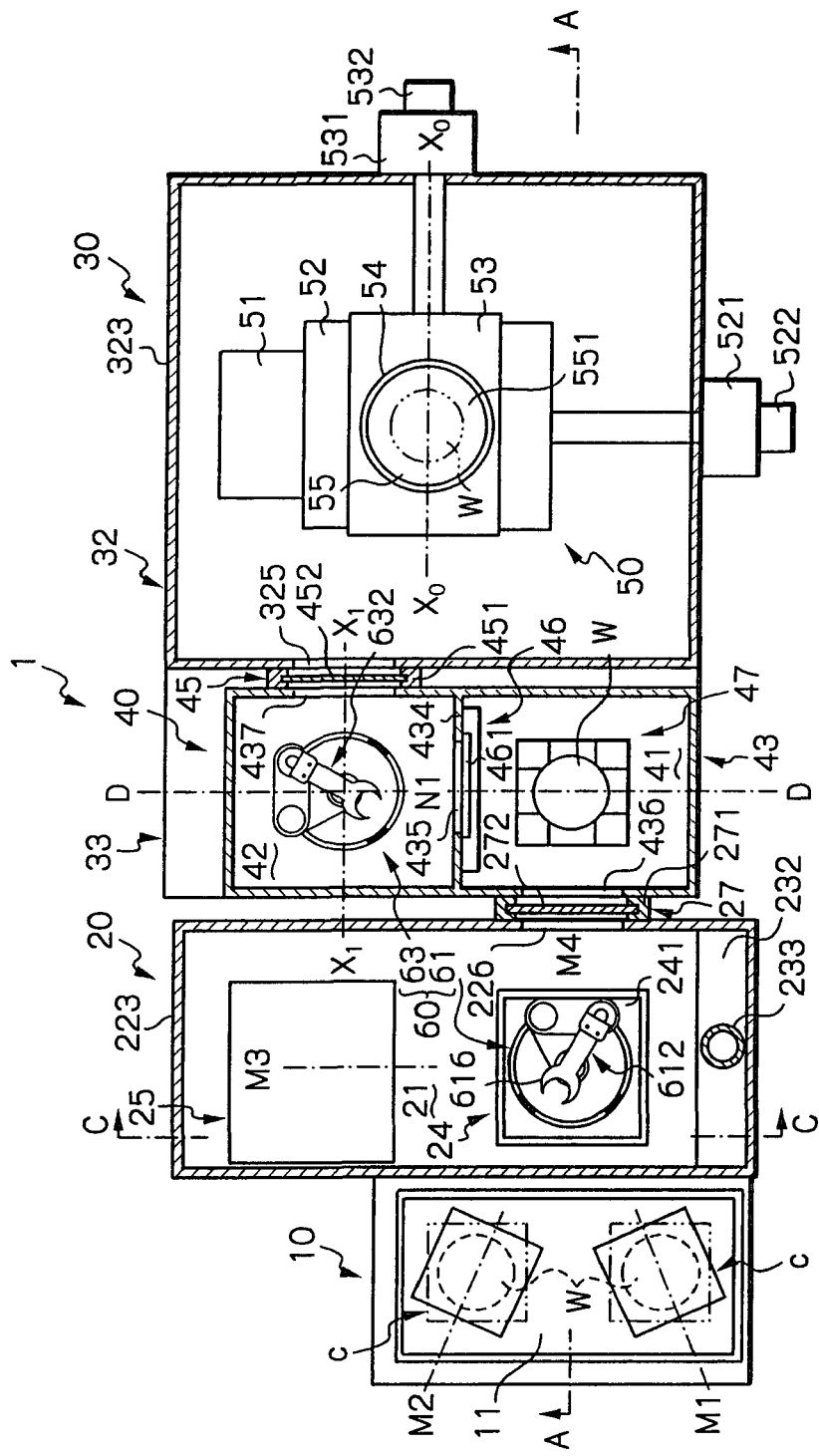
FIG. 2A is a plan view of the main components of the inspection apparatus illustrated in FIG. 1, viewed along a line B-B in FIG. 1.

FIGS. 1 and 2A illustrate main components of a semiconductor inspection apparatus 1 according to an embodiment in elevation and plan view, respectively.

The semiconductor inspection apparatus 1 of this embodiment comprises a cassette holder 10 for holding cassettes which store a plurality of wafers; a mini-environment chamber 20; a main housing 30 which defines a working chamber; a loader housing 40 disposed between the mini-environment chamber 20 and the main housing 30 to define two loading chambers; a loader 60 for loading a wafer from the cassette holder 10 onto a stage device 50 disposed in the main housing 30; and an electron-optical device 70 installed in the vacuum main housing 30. These components are arranged in a positional relationship as illustrated in FIGS. 1 and 2A. The semiconductor inspection apparatus 1 further comprises a precharge unit 81 disposed in the vacuum main housing 30; a potential applying mechanism 83 (see in FIG. 29) for applying potential to a wafer; an electron beam calibration mechanism 85 (see in FIG. 30); and an optical microscope 871 which forms part of an alignment controller 87 for aligning the wafer on the stage device 50.

Cassette Holder

The cassette holder 10 is configured to hold a plurality (two in this embodiment) of cassettes c (for example, closed cassettes such as SMIF, FOUP manufactured by Assist Co.) in which a plurality (for example, 25) of wafers are stacked in parallel in the vertical direction. The cassette holder 10 can be arbitrarily selected for installation adapted to a particular loading mechanism. Specifically, when a cassette, carried to the cassette holder 10, is automatically loaded into the cassette holder 10 by a robot or the like, the cassette holder 10 having a structure adapted to the automatic loading can be installed. When a cassette is manually loaded into the cassette holder 10, the cassette holder 10 having an open cassette structure can be installed. In this embodiment, the cassette holder 10 is of a type adapted to the automatic cassette loading, and comprises, for example, an up/down table 11, and an elevating mechanism 12 for moving the up/down table 11 up and down. The cassette c can be automatically set onto the up/down table 11 in a state indicated by chain lines in FIG. 2A. After the setting, the cassette c is automatically rotated to a state indicated by solid lines in FIG. 2A so that it is directed to the axis of pivotal movement of a first carrier unit within the mini-environment chamber 20. In addition, the up/down table 11 is moved down to a state indicated by chain lines in FIG. 1. In this way, the cassette holder 10 for use in automatic loading, or the cassette holder 10 for use in manual loading may be configured in known structures, so that detailed description on their structures and functions are omitted.

Figure 2B:
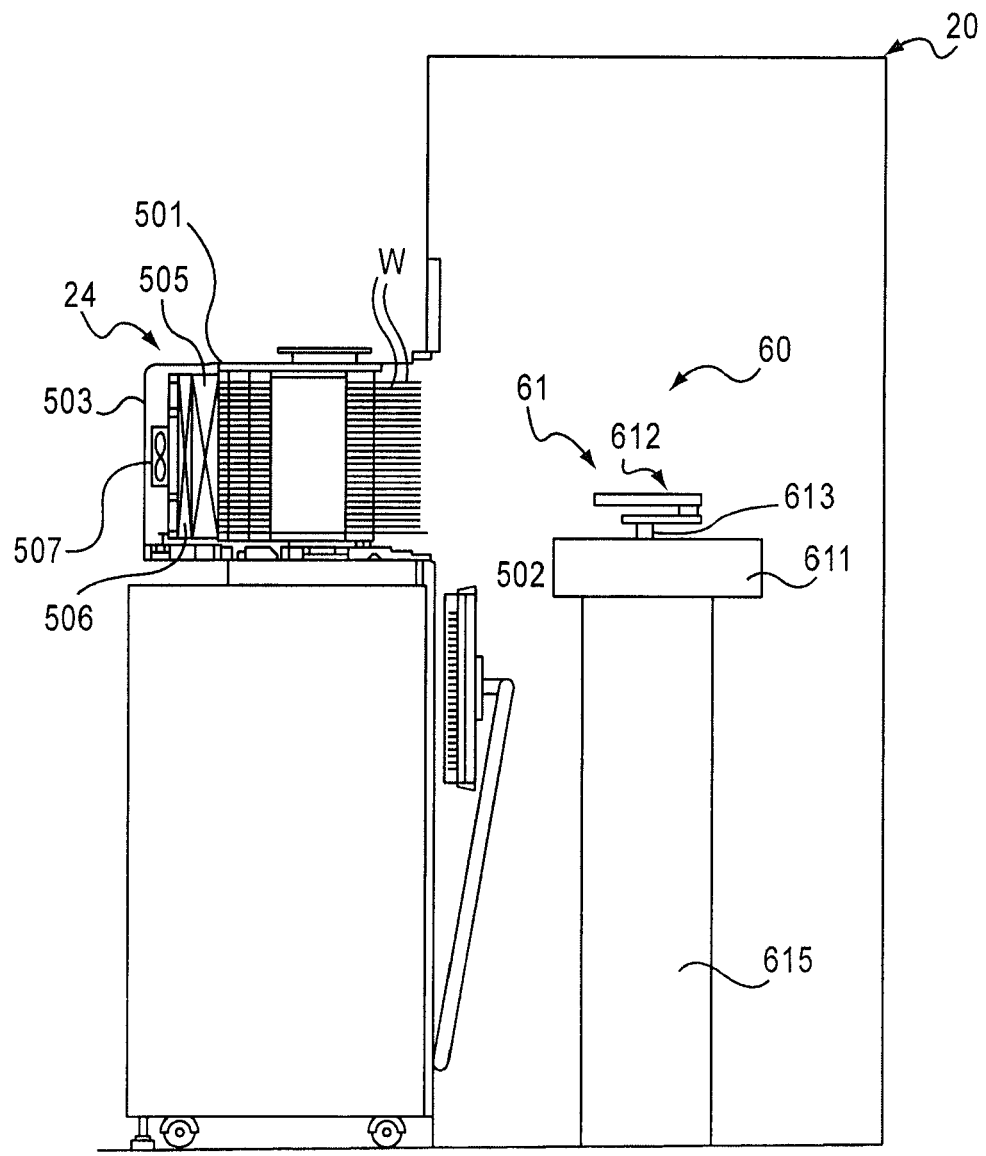
FIG. 2B is a schematic sectional view of a substrate carrier unit according to another embodiment of the invention.

In another embodiment, as shown in FIG. 2B, a plurality of 300 mm substrates is accommodated so that each is contained in a slot-like pocket fixedly mounted in an inner side of a box main body 501 so as to be transferred and stored. This substrate carrier box 24 is composed of a box main body 501 of cylinder with angular section, a door 502 for carrying the substrate in and out, which is coupled with an automatic opening/closing unit of the door for carrying the substrate in and out so as to be capable of mechanically opening and closing an opening in a side face of the box main body 501, a lid body 503 disposed in an opposite side of said opening, for covering another opening through which filters and a fan motor are to be attached or detached, a slot-like pocket (not shown) for holding a substrate W, a ULPA filter 505, a chemical filter 506, and a fan motor 507. In this embodiment, the substrate is carried in or out by a first carrier unit 612 of robot type in a loader 60.

It should be noted that substrates, i.e., wafers accommodated in the cassette c are wafers subjected to inspecting which is generally performed after a process for processing the wafers or in the middle of the process within a semiconductor manufacturing processes. Specifically, accommodated in the cassette are substrates or wafers which have undergone a deposition process, CMP, ion implantation and so on; wafers with circuit patterns on the surface thereof; or wafers which have not been formed with circuit patterns. Since a large number of wafers accommodated in the cassette c are spaced from each other in the vertical direction and arranged in parallel, the first carrier unit has an arm which is vertically movable such that a wafer at an arbitrary position can be held by the first carrier unit, as described later in detail.

Mini-Environment Chamber

Figure 3:
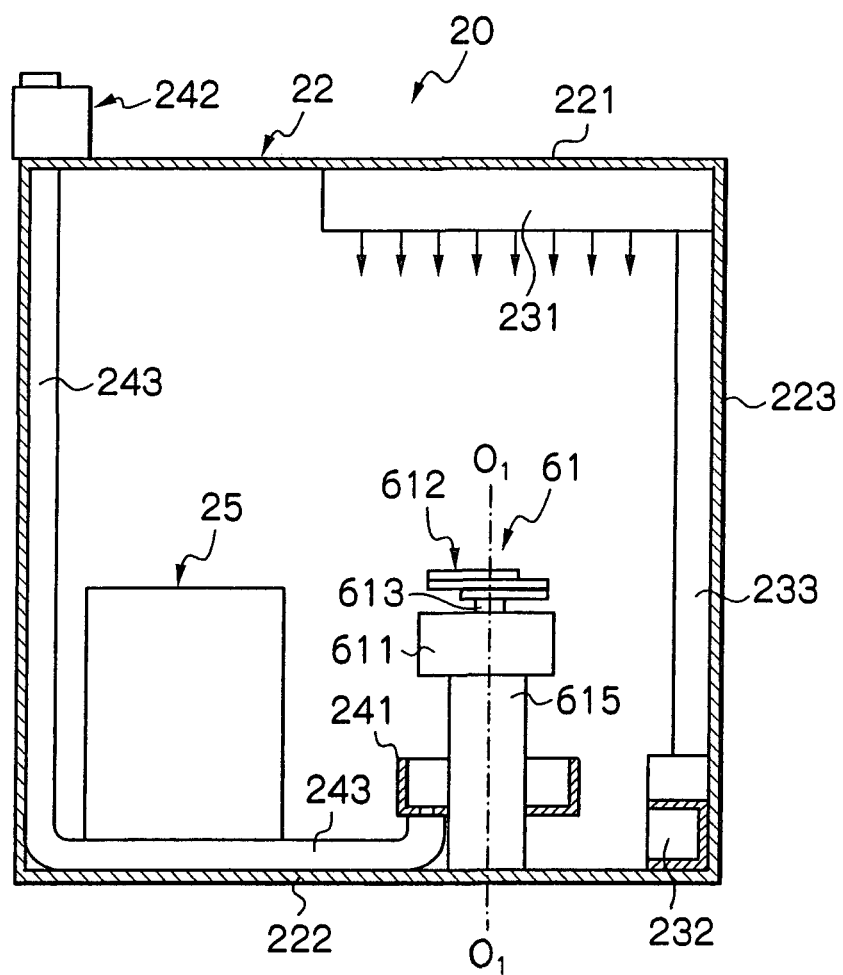
FIG. 3 is a cross-sectional view illustrating a mini-environment chamber in FIG. 1, viewed along a line C-C in FIG. 1.

In FIGS. 1 through 3, the mini-environment chamber 20 comprises a housing 22 which defines a mini-environment space 21 with a controlled atmosphere; a gas circulator 23 for circulating a gas such as clean air within the mini-environment space 21 for the atmosphere control; a discharger 24 for recovering a portion of air supplied into the mini-environment space 21 for discharging; and a pre-aligner 25 for roughly aligning a substrate, i.e., a wafer to be inspected, which is placed in the mini-environment space 21.

The housing 22 has a top wall 221, a bottom wall 222, and peripheral wall(s) 223 which surrounds four sides of the housing 22 to provide a structure for isolating the mini-environment space 21 from the outside. For controlling the atmosphere in the mini-environment space 21, the gas circulator 23 comprises a gas supply unit 231 attached to the top wall 221 within the mini-environment space 21 as illustrated in FIG. 3 for cleaning a gas (air in this embodiment) and delivering the cleaned gas downward through one or more gas nozzles (not shown) in laminar flow; a recovery duct 232 disposed on the bottom wall 222 within the mini-environment space for recovering air which has flowed to the bottom; and a conduit 233 for connecting the recovery duct 232 to the gas supply unit 231 for returning recovered air to the gas supply unit 231. In this embodiment, the gas supply unit 231 constantly replaces about 20% of air to be supplied, with the air taken from the outside of the housing 22 for cleaning. However, the percentage of gas taken from the outside may be arbitrarily selected. The gas supply unit 231 comprises an HEPA or ULPA filter of a known structure for creating cleaned air. The laminar downflow of cleaned air is mainly supplied such that the air passes a carrying surface of the first carrier unit 61, later described, disposed within the mini-environment space 21 to prevent dust particles, which could be produced by the carrier unit, from attaching to the wafer. Therefore, the downflow nozzles need not be positioned near the top wall as illustrated, but are only required to be above the carrying surface of the carrier unit 61. In addition, the air need not be supplied over the entire mini-environment space 21. It should be noted that an ion wind may be used as cleaned air to ensure the cleanliness as the case may be. Also, a sensor may be provided within the mini-environment space 21 for observing the cleanliness such that the apparatus is shut down when the cleanliness is below a predetermined level. An access port 225 is formed in a portion of the peripheral wall 223 of the housing 22 that is adjacent to the cassette holder 10. A shutter device of a known structure may be provided near the access port 225 to shut the access port 225 from the mini-environment chamber 20. The laminar downflow near the wafer may be, for example, at a rate of 0.3 to 0.4 msec. The gas supply unit 231 may be disposed outside the mini-environment space 21 instead of within the mini-environment space 21.

The discharger 24 comprises a suction duct 241 disposed at a position below the wafer carrying surface of the carrier unit 61 and below the carrier unit 61; a blower 242 disposed outside the housing 22; and a conduit 243 for connecting the suction duct 241 to the blower 242. The discharger 24 sucks a gas flowing down around the carrier unit and including dust, which could be produced by the carrier unit, through the suction duct 241, and discharges the gas outside the housing 22 through the conduits 243, 244 and the blower 242. In this event, the gas may be discharged into an exhaust pipe (not shown) which is laid to the vicinity of the housing 22.

The aligner 25 disposed within the mini-environment space 21 optically or mechanically detects an orientation flat (which refers to a flat portion formed along the outer periphery of a circular wafer) formed on the wafer, or one or more V-shaped notches formed on the outer peripheral edge of the wafer to previously align the orientation of the wafer in a rotating direction about the axis of the wafer at an accuracy of approximately .+-. one degree. The pre-aligner forms part of a mechanism for determining the coordinates of an object to be inspected, which is a feature of the claimed invention, and is responsible for rough alignment of an object to be inspected. Since the pre-aligner itself may be of a known structure, description on its structure and operation is omitted.

Though not shown, a recovery duct for the discharger 24 may also be provided below the pre-aligner such that air including dust, discharged from the pre-aligner, is discharged to the outside.

Main Housing

In FIGS. 1 and 2, the main housing 30, which defines the working chamber 31, comprises a housing body 32 that is supported by a housing supporting device 33 carried on a vibration isolator 37 disposed on a base frame 36. The housing supporting device 33 comprises a frame structure 331 assembled into a rectangular form. The housing body 32 comprises a bottom wall 321 securely carried on the frame structure 331; a top wall 322; and a peripheral wall 323 which is connected to the bottom wall 321 and the top wall 322 and surrounds four sides of the housing body 32, and isolates the working chamber 31 from the outside. In this embodiment, the bottom wall 321 is made of a relatively thick steel plate to prevent distortion due to the weight of equipment carried thereon such as the stage device 50. Alternatively, another structure may be employed. In this embodiment, the housing body 32 and the housing supporting device 33 are assembled into a rigid construction, and the vibration isolator 37 blocks vibrations from the floor, on which the base frame 36 is installed, from being transmitted to the rigid structure. A portion of the peripheral wall 323 of the housing body 32 that adjoins the loader housing 40, later described, is formed with an access port 325 for introducing and removing a wafer.

The vibration isolator 37 may be either of an active type which has an air spring, a magnetic bearing and so on, or a passive type likewise having these components. Since any known structure may be employed for the vibration isolator 37, description on the structure and functions of the vibration isolator itself is omitted. The working chamber 31 is held in a vacuum atmosphere by a vacuum system (not shown) of a known structure. A controller 2 for controlling the operation of the overall apparatus is disposed below the base frame 36.

Loader Housing

Figure 4:
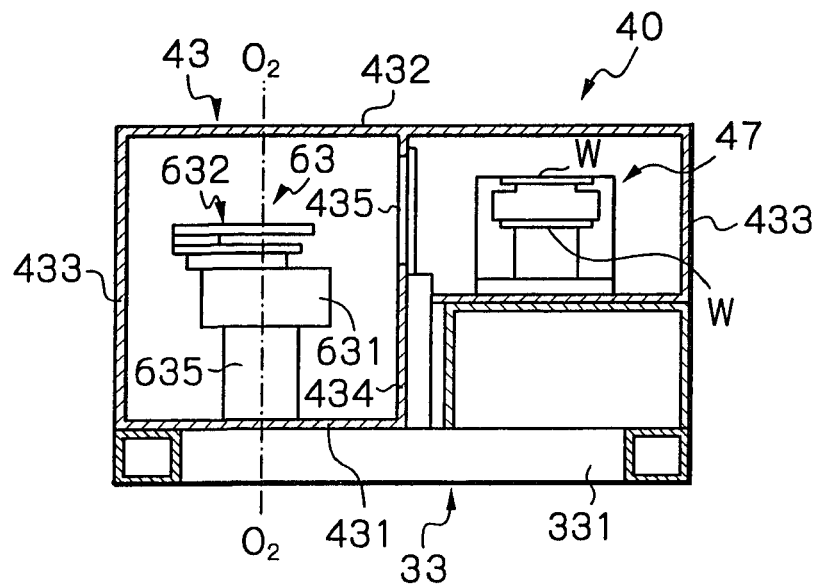
FIG. 4 is a cross-sectional view illustrating a loader housing in FIG. 1, viewed along a line D-D in FIG. 2.

In FIGS. 1, 2 and 4, the loader housing 40 comprises a housing body 43 which defines a first loading chamber 41 and a second loading chamber 42. The housing body 43 comprises a bottom wall 431; a top wall 432; a peripheral wall 433 which surrounds four sides of the housing body 43; and a partition wall 434 for partitioning the first loading chamber 41 and the second loading chamber 42 such that both the loading chambers can be isolated from the outside. The partition wall 434 is formed with an opening, i.e., an access port 435 for passing a wafer between both the loading chambers. Also, a portion of the peripheral wall 433 that adjoins the mini-environment device 20 and the main housing 30 is formed with access ports 436, 437. The housing body 43 of the loader housing 40 is carried on and supported by the frame structure 331 of the housing supporting device 33. This prevents vibrations from the floor from being transmitted to the loader housing 40 as well. The access port 436 of the loader housing 40 is in alignment with the access port 226 of the housing 22 of the mini-environment device 20, and a shutter device 27 is provided for selectively blocking communication between the mini-environment space 21 and the first loading chamber 41. The shutter device 27 has a sealing material 271 which surrounds the peripheries of the access ports 226, 436 and is fixed to the side wall 433 in close contact therewith; a door 272 for blocking air from flowing through the access ports in cooperation with the sealing material 271; and a driver 273 for moving the door 272. Likewise, the access port 437 of the loader housing 40 is in alignment with the access port 325 of the housing body 32, and a shutter 45 is provided for selectively blocking communication between the second loading chamber 42 and the working chamber 31 in a hermetic manner. The shutter 45 comprises a sealing material 451 which surrounds the peripheries of the access ports 437, 325 and is fixed to side walls 433, 323 in close contact therewith; a door 452 for blocking air from flowing through the access ports in cooperation with the sealing material 451; and a driver 453 for moving the door 452. Further, the opening 435 formed through the partition wall 434 is provided with a shutter 46 for closing the opening with the door 461 to selectively blocking communication between the first and second loading chambers in a hermetic manner. These shutter devices 27, 45, 46 are configured to provide air-tight sealing for the respective chambers when they are in a closed state. Since these shutter devices may be implemented by known ones, detailed description of their structures and operations is omitted. It should be noted that the method of supporting the housing 22 of the mini-environment device 20 is different from the method of supporting the loader housing 40. Therefore, for preventing vibrations from being transmitted from the floor through the mini-environment device 20 to the loader housing 40 and the main housing 30, a vibration-proof cushion material may be disposed between the housing 22 and the loader housing 40 to provide air-tight sealing for the peripheries of the access ports.

Figure 5:
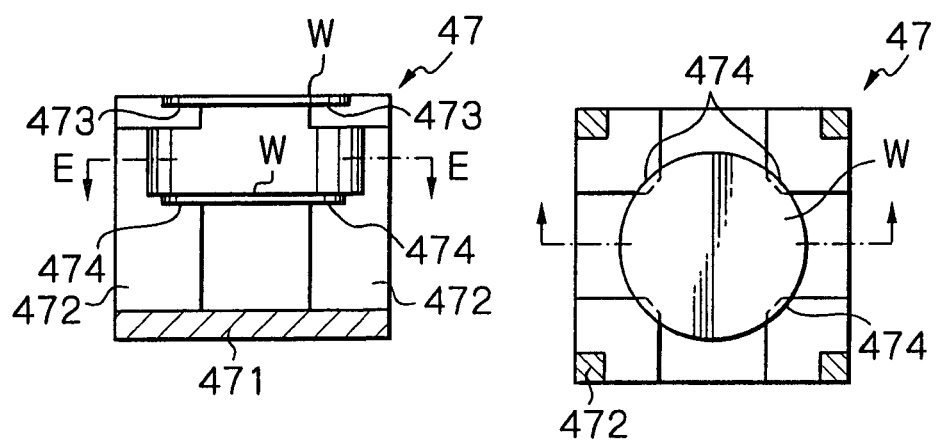

Within the first loading chamber 41, a wafer rack 47 is disposed for supporting a plurality (two in this embodiment) of wafers spaced in the vertical direction and maintained in a horizontal state. As illustrated in FIG. 5, the wafer rack 47 comprises posts 472 fixed at four corners of a rectangular base plate 471, spaced from one another, in an upright state. Each of the posts 472 is formed with supporting portions 473, 474 in two stages, such that peripheral edges of wafers W are carried on and held by these supporting portions. Then, leading ends of arms of the first and second carrier units 61, 63, later described, are brought closer to wafers from adjacent posts and grasp the wafers.

The atmosphere of the loading chambers 41, 42 can be controlled so as to be maintained in a high vacuum state (at a vacuum degree of $10^{-5}$ to $10^{-6}$ Pa) by a vacuum evacuator (not shown) in a known structure including a vacuum pump, not shown. In this event, the first loading chamber 41 may be held in a low vacuum atmosphere as a low vacuum chamber, while the second loading chamber 42 may be held in a high vacuum atmosphere as a high vacuum chamber, to effectively prevent contamination of wafers. The employment of such a structure allows a wafer, which is accommodated in the loading chamber and is next subjected to the defect inspection, to be carried into the working chamber without delay. The employment of such a loading chambers provides for an improved throughput for the defect inspection, and the highest possible vacuum state around the electron beam source which is required to be kept in a high vacuum state, together with the principle of a multi-beam type electron device, later described.

The first and second loading chambers 41, 42 are connected to a vacuum exhaust pipe and a vent pipe for an inert gas (for example, dried pure nitrogen) (neither of which are shown), respectively. In this way, the atmospheric state within each loading chamber is attained by an inert gas vent (which injects an inert gas to prevent oxygen and non-inert gases from contacting the surface). Since an apparatus itself for implementing the inert gas vent is known in structure, detailed description thereon is omitted.

In the inspection apparatus according to the present invention which uses an electron beam, when representative lanthanum hexaborate ($LaB_6$) used as an electron beam source for an electron-optical system, later described, is heated once to such a high temperature that it causes emission of thermal electrons, it should be exposed to oxygen as little as possible so as not to shorten its lifetime. The exposure of the electron beam source to oxygen can be prevented by carrying out the atmosphere control as mentioned above before introducing a wafer into the working chamber in which the electron-optical system is disposed.

Stage Device

The stage device 50 comprises a fixed table 51 disposed on the bottom wall 321 of the main housing 30; a Y-table 52 movable in the Y-direction on the fixed table 51 (the direction vertical to the drawing sheet in FIG. 1); an X-table 53 movable in the X-direction on the Y-table 52 (in the left-to-right direction in FIG. 1); a turntable 54 rotatable on the X-table; and a holder 55 disposed on the turntable 54. A wafer W is releasably held on a wafer carrying surface 551 of the holder 55. The holder 55 may be of a known structure which is capable of releasably holding a wafer by means of a mechanical or electrostatic chuck feature. The stage device 50 uses servo motors, encoders and a variety of sensors (not shown) to operate a plurality of tables as mentioned above to permit highly accurate alignment of a wafer W held on the carrying surface 551 by the holder 55 in the X-direction, Y-direction and Z-direction (in the up-down direction in FIG. 1) with respect to an electron beam irradiated from the electron-optical system 70, and in a direction about the axis normal to the wafer supporting surface ($\theta$ direction). The alignment in the Z-direction may be made such that the position on the carrying surface 551 of the holder 55, for example, can be finely adjusted in the Z-direction. In this event, a reference position on the carrying surface 551 is sensed by a position measuring device using a laser of small diameter (a laser interference range finder using the principles of interferometer) to control the position by a feedback circuit, not shown. Additionally or alternatively, the position of a notch or the orientation flat of a wafer is measured to sense the plane position and the rotational position of the wafer relative to the electron beam to control the position of the wafer by rotating the turntable 54 by a stepping motor which can be controlled in extremely small angular increments. In order to maximally prevent dust produced within the working chamber, servo motors 531, 531 and encoders 522, 532 for the stage device 50 are disposed outside the main housing 30. Since the stage device 50 may be of a known structure used, for example, in steppers and so on, detailed description of its structure and operation is omitted. Likewise, since the laser interference range finder may also be of a known structure, detailed description of its structure and operation is also omitted.

It is also possible to establish a basis for signals which are generated by previously inputting a rotational position, and X-, Y-positions of a wafer relative to the electron beam in a signal detecting system or an image processing system, later described. The wafer chucking mechanism provided in the holder 55 is configured to apply a voltage for chucking a wafer to an electrode of an electrostatic chuck, and the alignment is made by holding three points on the outer periphery of the wafer (preferably spaced equally in the circumferential direction). The wafer chucking mechanism comprises two fixed aligning pins and a push-type clamp pin. The clamp pin can effect automatic chucking and automatic releasing, and constitutes an electric conducting portion for applying the voltage.

While in this embodiment, the X-table is defined as a table which is movable in the left-to-right or right-to-left direction in FIG. 2; and the Y-table as a table which is movable in the up-down direction, a table movable in the left-to-right or right-to-left direction in FIG. 2 may be defined as the Y-table; and a table movable in the up-down direction as the X-table.

Loader

The loader 60 comprises a robot-type first carrier unit 61 disposed within the housing 22 of the mini-environment device 20; and a robot-type second carrier unit 63 disposed within the second loading chamber 42.

The first carrier unit 61 comprises an articulated arm 612 rotatable about an axis $O_1$-$O_1$ with respect to a driver 611. While an arbitrary structure may be used for the articulated arm, the articulated arm in this embodiment has three parts which are pivotably attached to each other. One part of the arm 612 of the first carrier unit 61, i.e., the first part closest to the driver 611 is attached to a rotatable shaft 613 by a driving mechanism (not shown) of a known structure, disposed within the driver 611. The arm 612 is pivotable about the axis $O_1$-$O_1$ by means of the shaft 613, and radially telescopic as a whole with respect to the axis $O_1$-

$O_1$ through relative rotations among the parts. At a leading end of the third part of the arm 612 furthest away from the shaft 613, a clamp 616 in a known structure for clamping a wafer, such as a mechanical chuck or an electrostatic chuck, is disposed. The driver 611 is movable in the vertical direction by an elevating mechanism 615 is of a known structure.

The first carrier unit 61 extends the arm 612 in either a direction M1 or a direction M2 within two cassettes c held in the cassette holder 10, and removes a wafer accommodated in a cassette c by carrying the wafer on the arm or by clamping the wafer with the chuck (not shown) attached at the leading end of the arm. Subsequently, the arm is retracted (in a state as illustrated in FIG. 2), and then rotated to a position at which the arm can extend in a direction M3 toward the pre-aligner 25, and stopped at this position. Then, the arm is extended to transfer the wafer held on the arm to the pre-aligner 25. After receiving a wafer from the pre-aligner 25, contrary to the foregoing, the arm is further rotated and stopped at a position at which it can extend to the second loading chamber 41 (in the direction M4), and transfers the wafer to a wafer receiver 47 within the second loading chamber 41. For mechanically clamping a wafer, the wafer should be clamped at a peripheral region (in a range of approximately 5 mm from the peripheral edge). This is because the wafer is formed with devices (circuit pattern) over the entire surface except for the peripheral region, and clamping the inner region would result in failed or defective devices.

The second carrier unit 63 is basically identical to the first carrier unit 61 in structure except that the second carrier unit 63 carries a wafer between the wafer rack 47 and the carrying surface of the stage device 50, so that detailed description thereon is omitted.

In the loader 60, the first and second carrier units 61, 63 carry a wafer from a cassette held in the cassette holder 10 to the stage device 50 disposed in the working chamber 31 and vice versa, while keeping the wafer substantially in a horizontal state. The arms of the carrier units are moved in the vertical direction only when a wafer is removed from and inserted into a cassette, when a wafer is carried on and removed from the wafer rack, and when a wafer is carried on and removed from the stage device 50. It is therefore possible to smoothly carry a wafer even if it is a large one, for example, a wafer having a diameter of 30 cm.

Transfer of Wafer

Next, how a wafer is transferred in the apparatus will be described in sequence from the cassette c held by the cassette holder 10 to the stage device 50 disposed in the working chamber 31.

As described above, when the cassette is manually set, the cassette holder 10 having a structure adapted to the manual setting is used, and when the cassette is automatically set, the cassette holder 10 having a structure adapted to the automatic setting is used. In this embodiment, as the cassette c is set on the up/down table 11 of the cassette holder 10, the up/down table 11 is moved down by the elevating mechanism 12 to align the cassette c with the access port 225.

As the cassette is aligned with the access port 225, a cover (not shown) provided for the cassette is opened, and a cylindrical cover is applied between the cassette c and the access port 225 of the mini-environment to block the cassette and the mini-environment space 21 from the outside. Since these structures are known, detailed description of their structures and operations omitted. When the mini-environment device 20 is provided with a shutter for opening and closing the access port 225, the shutter is operated to open the access port 225.

On the other hand, the arm 612 of the first carrier unit 61 remains oriented in either the direction M1 or M2 (in the direction M2 in this description). As the access port 225 is opened, the arm 612 extends to receive one of wafers accommodated in the cassette at the leading end. While the arm and a wafer to be removed from the cassette are adjusted in the vertical position by moving up or down the driver 611 and the arm 612 of the first carrier unit 61 in this embodiment, the adjustment may be made by moving the up/down table 11 of the cassette holder 10, or made by both.

As the arm 612 receives the wafer, the arm 621 is retracted, and the shutter is operated to close the access port (when the shutter is provided). Next, the arm 612 is pivoted about the axis $O_1$-$O_1$ such that it can extend in the direction M3. Then, the arm 612 is extended and transfers the wafer carried at the leading end or clamped by the chuck onto the pre-aligner 25 which aligns the orientation of the rotating direction of the wafer (the direction about the central axis vertical to the wafer plane) within a predetermined range. Upon completion of the alignment, the carrier unit 61 retracts the arm 612 after a wafer has been received from the pre-aligner 25 to the leading end of the arm 612, and rotates the arm 612 to a position in which the arm 612 can be extended in a direction M4. Then, the door 272 of the shutter device 27 is moved to open the access ports 226, 436, and the arm 612 is extended to place the wafer on the upper stage or the lower stage of the wafer rack 47 within the first loading chamber 41. It should be noted that before the shutter device 27 opens the access ports 226, 436 to transfer the wafer to the wafer rack 47, the opening 435 formed through the partition wall 434 is closed by the door 461 of the shutter 46 in an air-tight state.

In the process of carrying a wafer by the first carrier unit, clean air flows (as downflow) in laminar flow from the gas supply unit 231 disposed on the housing of the mini-environment device to prevent dust from attaching to the upper surface of the wafer while being carried. A portion of the air near the carrier unit (in this embodiment, about 20% of the air supplied from the supply unit 231, which is substantially contaminated air) is sucked from the suction duct 241 of the discharger 24 and discharged outside the housing. The remaining air is recovered through the recovery duct 232 disposed on the bottom of the housing and returned again to the gas supply unit 231.

As the wafer is placed into the wafer rack 47 within the first loading chamber 41 of the loader housing 40 by the first carrier unit 61, the shutter device 27 is closed to seal the loading chamber 41. Then, the first loading chamber 41 is filled with an inert gas to expel air. Subsequently, the inert gas is also discharged so that a vacuum atmosphere dominates within the loading chamber 41. The vacuum atmosphere within the loading chamber 41 may be at a low vacuum degree. When a certain degree of vacuum is formed within the loading chamber 41, the shutter 46 is operated to open the access port 434 which has been sealed by the door 461, and the arm 632 of the second carrier unit 63 is extended to receive one wafer from the wafer receiver 47 with the clamp at the leading end (the wafer is carried on the leading end or clamped by the chuck attached to the leading end). Upon completion of the receipt of the wafer, the arm 632 is retracted, followed by the shutter 46 again operated to close the access port 435 by the door 461. It should be noted that the arm 632 previously takes a posture in which it can extend in the direction N1 of the wafer rack 47 before the shutter 46 is operated to open the access port 435. Also, as described above, the access ports 437, 325 are closed by the door 452 of the shutter 45 before the shutter 46 is opened to block communication between the second loading chamber 42 and the working chamber 31 in an air-tight state, so that the second loading chamber 42 can be evacuated.

As the shutter 46 is operated to close the access port 435, the second loading chamber 42 is again evacuated at a higher degree of vacuum than the first loading chamber 41. Meanwhile, the arm 632 of the second carrier unit 63 is rotated to a position from which it can extend toward the stage device 50 within the working chamber 31. On the other hand, in the stage device 50 within the working chamber 31, the Y-table 52 is moved upward, as viewed in FIG. 2, to a position at which the center line $X.sub.0$-$X.sub.0$ of the X-table 53 substantially aligns with an X-axis $X.sub.1$-$X.sub.1$ which passes a pivotal axis $O.sub.2$-$O.sub.2$ of the second carrier unit 63. The X-table 53 in turn is moved to the position closest to the leftmost position in FIG. 2, and remains at this position. When the second loading chamber 42 is evacuated to substantially the same degree of vacuum as the working chamber 31, the door 452 of the shutter 45 is moved to open the access ports 437, 325, allowing the arm 632 to extend so that the leading end of the arm 632, which holds a wafer, approaches the stage device 50 within the working chamber 31. Then, the wafer is placed on the carrying surface 551 of the stage device 50. As the wafer has been placed on the carrying surface 551, the arm 632 is retracted, followed by the shutter 45 operated to close the access ports 437, 325.

The foregoing description has been made about the operations in which a wafer in the cassette c is carried and placed on the stage device 50. For returning a wafer, which has been carried on the stage device 50 and processed, from the stage device 50 to the cassette c, the operation reverse to the foregoing is performed. Since a plurality of wafers are stored in the wafer rack 47, the first carrier unit 61 can carry a wafer between the cassette and the wafer rack 47 while the second carrier unit 63 can carry a wafer between the wafer rack 47 and the stage device 50, so that the inspecting operation can be efficiently carried out.

Specifically, when there is a wafer A, which has been already been processed, and a wafer B, which has not yet been processed, in a wafer rack 47 of a second carrier unit, (1) at first, the wafer B which has not yet been processed is transferred to the stage 50 and the processing is started;

(2) during this processing, the wafer A which has already been processed is transferred from the stage 50 to the wafer rack 47 by an arm, a wafer C which has not yet been processed is picked up from the wafer rack again by the arm, which after having been positioned by a pre-aligner, is further transferred to the wafer rack 47 of a loading chamber 41.

This procedure may allow the wafer A, which has already been processed, to be substituted by the wafer C, which has not yet been processed, in the wafer rack 47, during processing of wafer B.

Alternatively, depending on how such an apparatus executes an inspection and/or an evaluation, a plurality of stage units 50 may be arranged in parallel, and in this case, wafers are transferred from one wafer rack 47 for each of the stage units 50, thereby providing simultaneous processing of a plurality of wafers.

Figure 6:
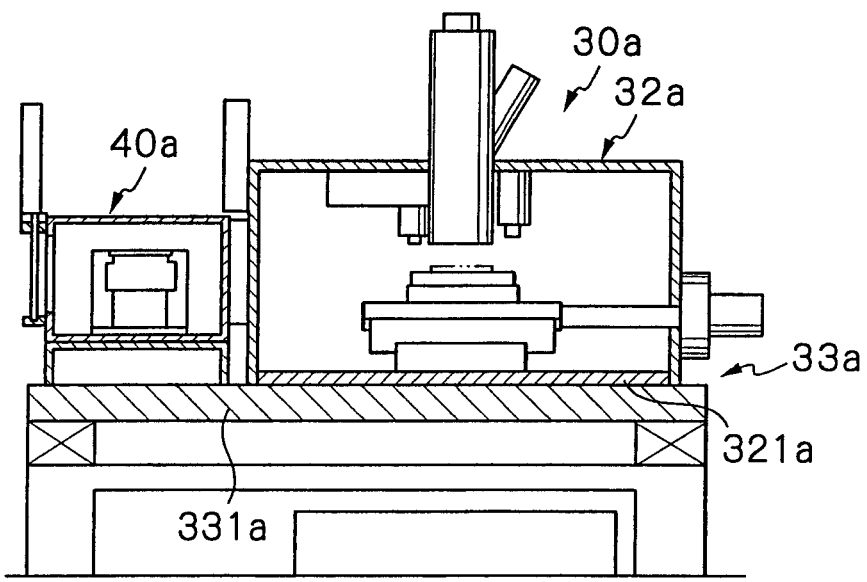
FIG. 6 is a diagram illustrating modifications to a method of supporting a main housing.
Figure 7:
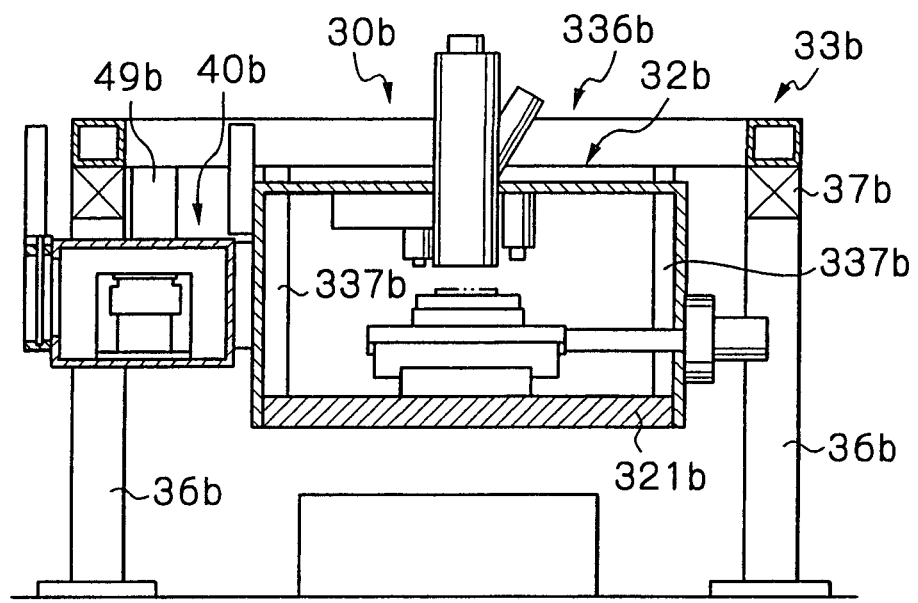
FIG. 7 is a diagram illustrating modifications to a method of supporting a main housing.

FIG. 6 illustrates typical modifications to the method of supporting the main housing 30. In an typical modification illustrated in FIG. 6, a housing supporting device 33a is made of a thick rectangular steel plate 331a, and a housing body 32a is carried on the steel plate. Therefore, the bottom wall 321a of the housing body 32a is thinner than the bottom wall 222 of the housing body 32 in the foregoing embodiment. In a typical modification illustrated in FIG. 7, a housing body 32b and a loader housing 40b are suspended from a frame structure 336b of a housing supporting device 33b. Lower ends of a plurality of vertical frames 337b fixed to the frame structure 336b are fixed to four corners of a bottom wall 321b of the housing body 32b, such that the peripheral wall and the top wall are supported by the bottom wall. Then, a vibration isolator 37b is disposed between the frame structure 336b and a base frame 36b. Likewise, the loader housing 40b is suspended by a suspending member 49b fixed to the frame structure 336. In the typical modification of the housing body 32b illustrated in FIG. 7, the housing body 32b is supported in suspension, the center of gravity of the main housing and a variety of devices disposed therein, as a whole, can be brought downward. The methods of supporting the main housing and the loader housing, including the typical modifications described above, are configured to prevent vibrations from being transmitted from the floor to the main housing and the loader housing.

In another typical modification, not shown, only the housing body of the main housing is supported by the housing supporting device from below, while the loader housing may be placed on the floor in the same way as the adjacent mini-environment device. Alternatively, in a further typical modification, not shown, only the housing body of the main housing is supported by suspension from the frame structure, while the loader housing may be placed on the floor in the same way as the adjacent mini-environment device.

According to the subject embodiment, the following advantages are provided:

(A) the general configuration can be established for an inspection apparatus in accordance with an electron beam based projection scheme, which can process objects under inspection at a high throughput;

(B) a clean gas is forced to flow onto an object to be inspected within the mini-environment space to prevent dust from attaching to the object to be inspected, and a sensor is provided for observing the cleanliness, thereby making it possible to inspect the object to be inspected while monitoring dust within the space;

(C) when the loading chamber and the working chamber are integrally supported through a vibration isolator, an object to be inspected can be carried to the stage device and inspected thereon without being affected by the external environment.

Electron-Optical-System

Figure 8:
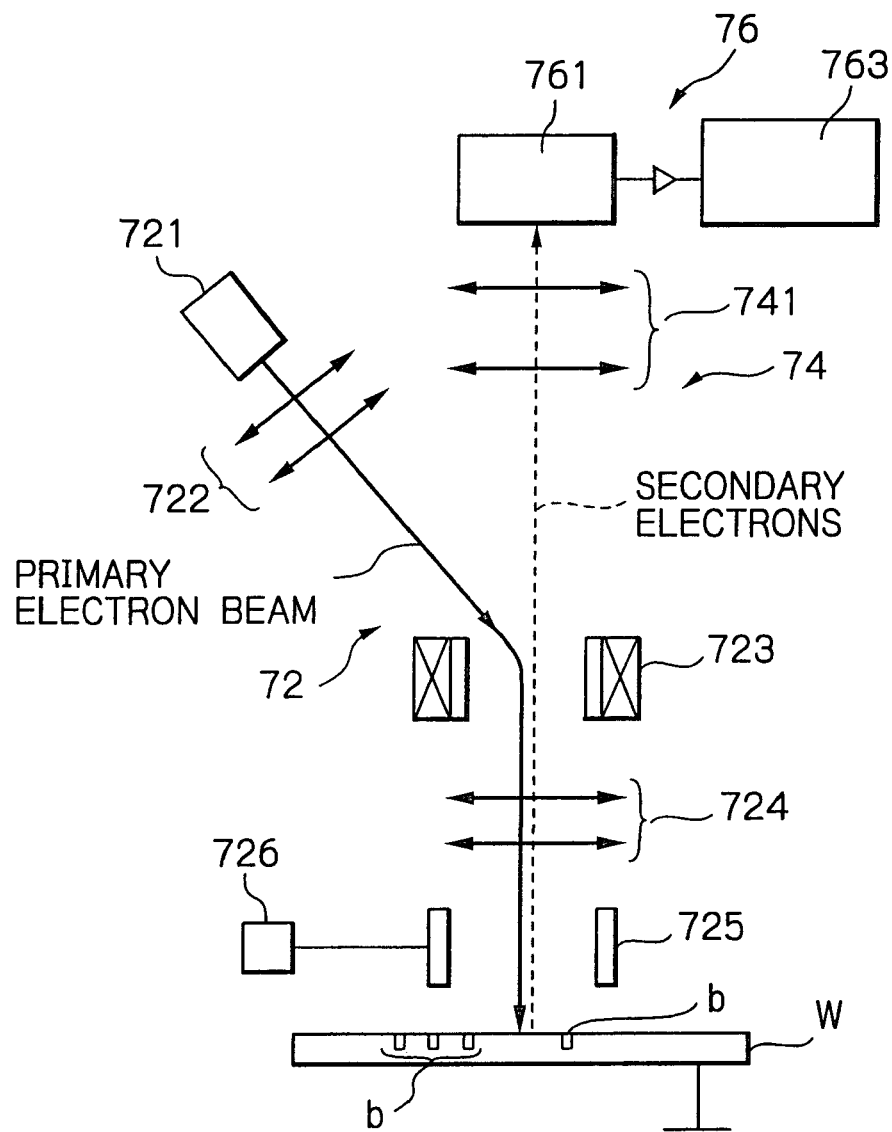
FIG. 8 is a schematic diagram generally illustrating the configuration of an electron-optical system in the inspection apparatus of FIG. 1.

The electron-optical system 70 comprises a column 71 fixed on the housing body 32. Disposed within the column 71 are an electron-optical system comprised of a primary electron-optical system (hereinafter simply called the "primary optical system") 72 and a secondary electron-optical system (hereinafter simply called the "secondary optical system") 74, and a detecting system 76, as illustrated generally in FIG. 8. The primary optical system 72, which is an optical system for irradiating the surface of a wafer W to be inspected with an electron beam, comprises an electron gun 721 for emitting an electron beam; a lens system 722 comprised of electrostatic lenses for converging a primary electron beam emitted from the electron gun 721; a Wien filter, i.e., an E.times.B separator 723; and an objective lens system 724. These components are arranged in order with the electron gun 721 placed at the top, as illustrated in FIG. 8. The lenses constituting the objective lens system 724 in this embodiment are retarding field type objective lenses. In this embodiment, the optical axis of the primary electron beam emitted from the electron gun 721 is oblique to the optical axis of irradiation along which the wafer W to be inspected is irradiated with the electron beam (perpendicular to the surface of the wafer). Electrodes 725 are disposed between the objective lens system 724 and the wafer W to be inspected. The electrodes 725 are axially symmetric about the optical axis of irradiation of the primary electron beam, and controlled in voltage by a power supply 726.

The secondary optical system 74 comprises a lens system 741 comprised of electrostatic lenses which pass secondary electrons separated from the primary optical system by an E.times.B deflector 723. This lens system 741 functions as a magnifier for enlarging a secondary electron image.

The detecting system 76 comprises a detector 761 and an image processing unit 763 which are disposed on a focal plane of the lens system 741.

Electron Gun (Electron Beam Source)

A thermal electron beam source is employed as an electron beam source. Cathode is $L_aB_6$. Other material may be used for the cathode so far as it has a high melting point (low vapor pressure at high temperature) and a small work function. The cathode with its tip portion formed into cone shape or the emitter member formed into trapezoidal cone shape with the tip portion of the cone having been cut away may be used. The diameter of the tip of the trapezoidal cone may be about 100 .mu.m. Although in other methods, an electron beam source of the field emission type or the thermal field emission type has been used, in such a case where a relatively large area (for example, 100.times.25 to 400.times.100 .mu.m.sup.2) is irradiated with a high current (in the order of 1 .mu.A) as is the case of the present invention, most preferably the thermal electron source using $L_aB_6$ should be employed. (In the SEM method, typically the thermal field electron beam source is used.) It is to be appreciated that the thermal electron beam source is one method in which the cathode is heated to emit an electron, while the thermal electric field emission electron beam source is one method in which a high electric field is applied to the cathode to emit an electron and further the electron emitting section is heated so as to stabilize the emission of electrons.

Primary Optical System

A section for forming an electron beam irradiated from an electron gun and irradiating the electron beam against a wafer surface, which forms a rectangle or circle (ellipse) on said wafer surface, said section is called the primary optical system. Controlling the lens condition in the primary optical system allows control of a beam size and/or a current density. Further, an E.times.B filter (Wien filter) disposed in coupling sections of the primary and the secondary electronic optical systems controls the primary electron beam so that it enters the wafer at right angles.

The thermal electrons emitted from a $L_aB_6$ cathode are formed into a cross-over image on a gun aperture by using a Wehnelt triple-anode lens. The electron beam, whose angle of incidence to the lens has been appropriately adjusted by a lighting field stop, is formed into an image on a NA aperture in a rotationally asymmetrical form by controlling the electrostatic lens in the primary electronic optical system, and then irradiated onto the wafer surface as a plane. The rear stage of the electrostatic lens in the primary electronic optical system is composed of a triple stage quadrupole (QL) and a single stage of electrode for correcting the aperture aberration. The quadrupole lens requires strict alignment accuracy but has a stronger focusing effect than a rotationally symmetrical lens, and thereby the aperture aberration corresponding to the spherical aberration of the rotationally symmetrical lens can be corrected by applying an appropriate voltage to the aperture aberration correcting electrode. Thereby, a uniform plane beam can be irradiated over a specified region.

Secondary Electronic Optical System

A two-dimensional secondary electron image generated by an electron beam irradiated onto a wafer is formed into an image by electrostatic lenses (CL, TL) corresponding to an objective lens on a location of field stop and magnified and projected by a subsequent stage of lens (PL). Said image-forming and projecting optical system is called the secondary optical system.

At that time, a negative bias voltage (decelerating electric field voltage) is applied to the wafer. The decelerating electric field effectively decelerates the irradiation beam to reduce damage in the sample, while it accelerates secondary electrons emitted from the sample surface using the potential difference between the CL and the wafer to reduce chromatic aberration. Electrons focused by the CL are further formed into an image on a FA by the TL, which image is then magnified and projected by the PL so as to be formed into an image on a secondary electron detector (MCP). In the present optical system, a NA is positioned between the CL and the TL, so that the optical system can be constructed in which an extra-axis aberration may be reduced by optimizing the NA.

Further, in order to correct errors in the fabrication of the electronic optical systems and/or astigmatism or an anisotropic magnification of an image resulting from electrons passing through an E.times.B filter (a Wien filter), an electrostatic octopole (STIG) is disposed to make a correction, while in order to deal with the problem of an axial offset, deflectors (OP) are arranged between respective lenses so as to make the correction. This yields a projecting optical system with a uniformed resolution in the field of view.

E.Times.B Unit (Wien Filter)

An E.times.B unit is a unit of electromagnetic prism optical system, in which an electrode and a magnetic pole are arranged in the directions orthogonal to each other so that an electric field and a magnetic field cross at right angles. If the electromagnetic field is selectively given appropriately, a condition (the Wien condition) can be made where an electron beam entering into the field from one direction is deflected, while in the electron beam entering from the opposite direction, a force applied by the electric field and another force applied by the magnetic field are offset to each other, and thereby the primary electron beam is deflected to be irradiated onto the wafer at right angles and the secondary electron beam advances straight ahead toward the detector.

Figure 9:
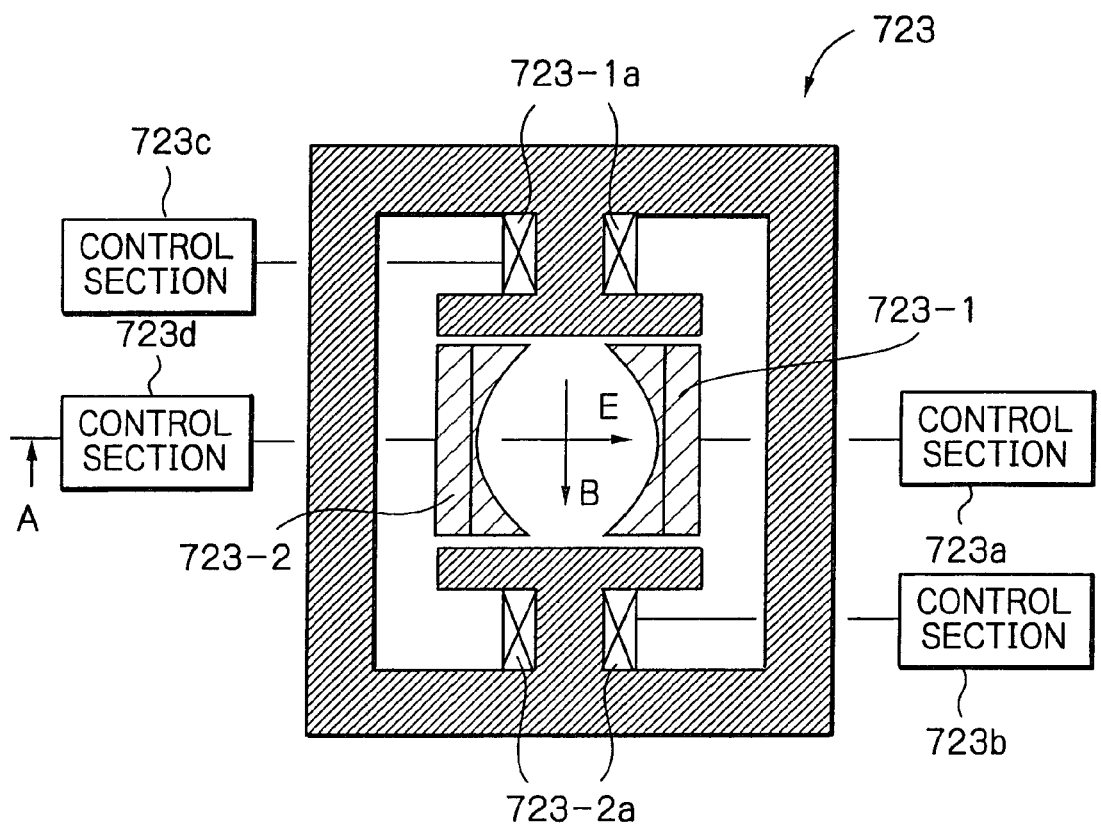
FIG. 9 is a sectional view of the construction of an electron beam deflecting section of the E.times.B separator.
Figure 10:
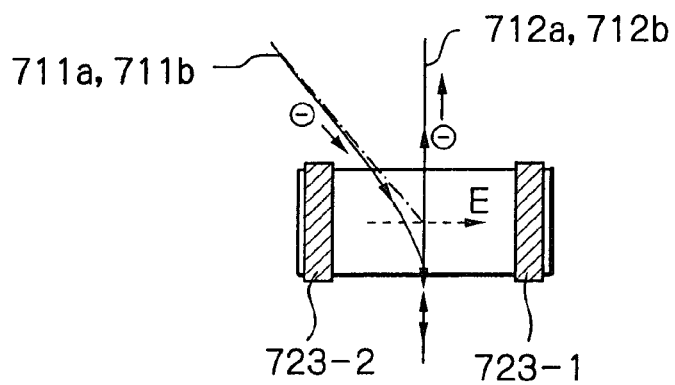
FIG. 10 is a sectional view taken along a line A-A in FIG. 9.

The detailed configuration of an electron beam deflecting section 723 will be described with reference to FIGS. 9 and 10 illustrating a longitudinal sectional view taken along the line A-A of FIG. 9. As shown in FIG. 9, a field in the electron beam deflecting section is structured such that the electric field is crossed with the magnetic field at right angles in a plane normal to the optical axis of said projecting optical system, that is, an E.times.B structure.

In this regard, the electric field may be generated by electrodes 723-1 and 723-2, each having a curved surface of concave shape. The electric fields generated by the electrodes 723-1 and 723-2 are respectively controlled by control sections 723a and 723b. On the other hand, arranging the electromagnetic coils 723-1a and 723-2a so as to be crossed with the electrodes 723-1 and 723-2 for generating the electric field allows the magnetic field to be generated. It is to be noted that those electrodes 723-1 and 723-2 for generating the electric field are arranged to be point-symmetrical (but may also be arranged in concentric circles).

In this case, in order to improve the uniformity of the magnetic field, a magnetic path 42 is formed with a pole piece in the form of parallel plate shape. The behavior of the electron beam on the longitudinal cross sectional plane taken along the A-A line is shown in FIG. 10. The irradiated electron beams 711a and 711b, after having been deflected by the electric field generated by the electrodes 723-1 and 723-2 and the magnetic field generated by the electromagnetic coils 723-1a and 723-2a, enter onto the sample surface in the vertical direction.

In this configuration, the positions and the angles of incidence of the irradiation electron beams 711a and 711b to the electron beam deflecting section 723 are univocally determined as the energy of the electron is determined. In addition, in order to advance the secondary electrons 712a and 712b straight ahead, the respective control sections 723a and 723d, and 723c and 723b control the electric field generated by the electrodes 723-1 and 723-2 and the magnetic field generated by the electromagnetic coils 723-1a and 723-2a so that the condition for the electric field and the magnetic field may be shown as vB=E, and thereby the secondary electrons are allowed to go straight through the electron beam deflecting section 723 into said projecting optical section. Where, V is a velocity of the electrons (m/s), B is the magnetic field (T), e is an amount of the electric charge (C) and E is the electric field (V/m).

Detector

A secondary electron image from the wafer, which is formed into an image by the secondary optical system, is primarily amplified in the micro-channel plate (MCP) and then impinges against a fluorescent screen to be converted into an optical image. As for the principle of the MCP, millions of very thin glass capillaries made of conductive material, each having a diameter of 6 to 25 .mu.m and a length of 0.24 to 1.0 mm, are bundled and formed into a thin plate, and application of a specified voltage makes each of the capillaries work as an individual secondary electron amplifier so as to form the secondary electron amplifier as a whole.

The image that has been converted into the light by said detector is projected on the TDI-CCD by the FOP system disposed in the atmosphere through a vacuum permeable window on a one-to-one basis.

Next, the operation of the electron-optical device 70 configured as described above will be described.

As shown in FIG. 8, the primary electron beam emitted from the electron gun 721 is converged by the lens system 722. The converged primary electron beam enters the E.times.B deflector 723, is deflected so that it is irradiated vertical to the surface of the wafer W, and focused on the surface of the wafer W by the objective lens system 724.

The secondary electrons emitted from the wafer by the irradiation of the primary electron beam are accelerated by the objective lens system 724, enter the E.times.B deflector 723, travels straight through the deflector 723, and are lead to the detector 761 by the lens system 741 of the secondary optical system. Then, the secondary electrons are detected by the detector 761 which generates a detection signal for an image processing unit 763.

Assume in this embodiment that the objective lens system 724 is applied with a high voltage in a range of 10 to 20 kV, and that a wafer has been prepared in place.

Here, when the electrodes 725 are applied with a voltage of −200 V if the wafer W includes a via b, an electric field of 0 to −0.1 V/mm ("−" indicates that the wafer W has a higher potential) is produced on the surface of the wafer W irradiated with the electron beam. In this state, although the wafer W can be inspected for defects without causing a discharge between the objective lens system 724 and the wafer W, a slight degradation is experienced in the efficiency of detecting the secondary electrons. Therefore, a sequence of operations involving irradiating the electron beam and detecting the secondary electrons is performed, for example, four times, such that the results of the four detections are applied with processing such as accumulative addition, averaging operation and so on to obtain a predetermined detection sensitivity.

On the other hand, when the wafer is free from the via b, no discharge is caused between the objective lens system 724 and the wafer even if the electrodes 725 are applied with a voltage of +350, so that the wafer W can be inspected for defects. In this event, since the secondary electrons are converged by the voltage applied to the electrodes 725 and further converged by the objective lens 724, the detector 761 with greater efficiency detects the secondary electrons. Consequently, the wafer defect detector processing is performed at a higher speed, so that the inspection can be carried at a higher throughput.

Figure 11:
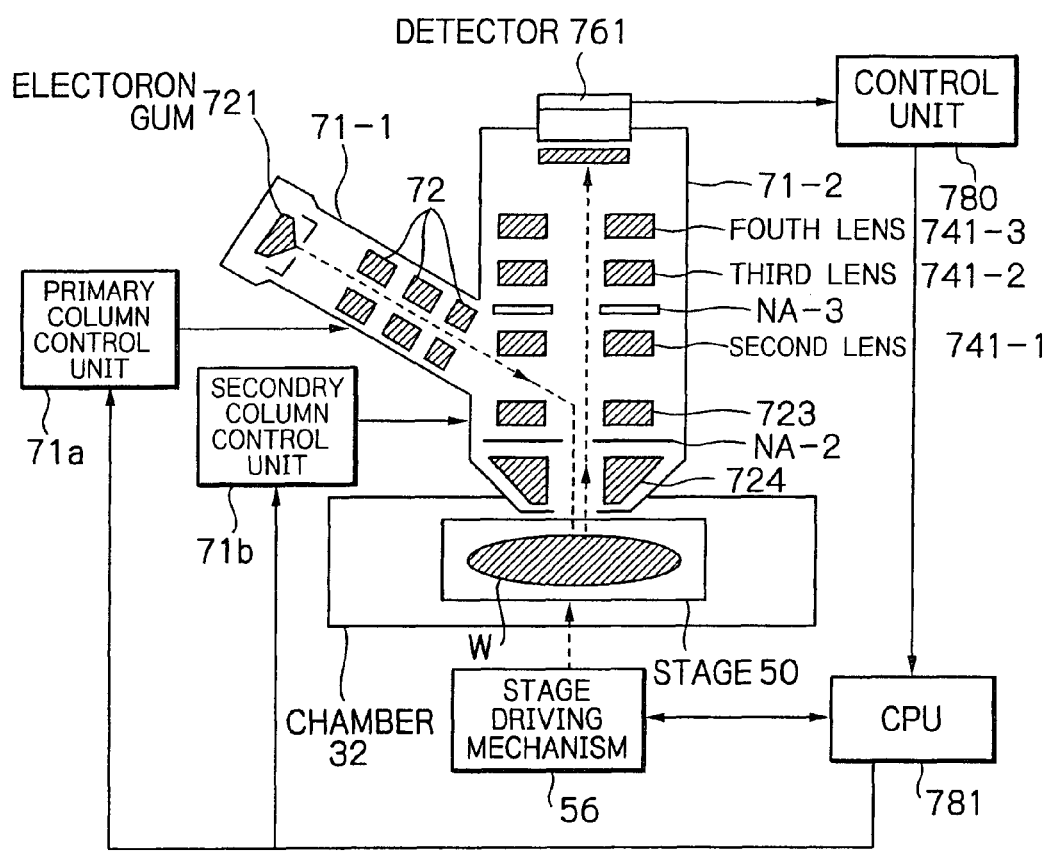
FIG. 11 is a schematic general view for explaining an apparatus according to one embodiment of the invention.

Description of the Relationship Among Main Functions in the Projecting Method and its General View A schematic general view of an inspection apparatus according to the present invention is shown in FIG. 11. However, some components are omitted for illustration.

In FIG. 11, the inspection apparatus has a primary column 71-1, a secondary column 71-2 and a chamber 32. An electron gun 721 is arranged on the inside of the primary column 71-1, and a primary optical system 72 is disposed along the optical axis of an electron beam (a primary electron beam) irradiated from the electron gun 721. Further, a stage 50 is installed in the interior of the chamber 32 and a sample W is loaded on the stage 50.

On the other hand, in the interior of the secondary column 71-2, a cathode lens 724, a numerical aperture NA-2, a Wien filter 723, a second lens 741-1, a field aperture NA-3, a third lens 741-2, a fourth lens 741-3 and a detector 761 are located on the optical axis of the secondary electron beam emanating from the sample W. It is to be noted that the numerical aperture NA-2 corresponds to an aperture diaphragm, which is a thin plate made of metal (Mo or the like) having a circular aperture formed therein. Herein, an aperture section is arranged so as to be at a focused location of the primary electron beam and also at a focusing location of the cathode lens 724. Accordingly, the cathode lens 724 and the numerical aperture NA-2 construct a telecentric electronic optical system.

On the other hand, the output from the detector 761 is input into a control unit 780, and the output from the control unit 780 is input into a CPU 781. A control signal from the CPU 781 is input into a primary column control unit 71a, a secondary column control unit 71b and a stage driving mechanism 56. The primary column control unit 71a controls a lens voltage in the primary optical system 72, and the secondary column control unit 71b controls lens voltages in the cathode lens 724 and the second lenses 741-1 to the fourth lens 741-3 and also an electromagnetic field applied to the Wien filter 723.

Further, the stage driving mechanism 56 transmits position data of the stage to the CPU 781. Still further, the primary column 71-1, the secondary column 71-2 and the chamber 32 are connected to the vacuum exhausting system (not shown) and exhausted by a turbo pump in the vacuum exhausting system so as for the interior thereof to be maintained in vacuum.

(PRIMARY BEAM) The primary electron beam from the electron gun 721 enters into the Wien filter 723 while receiving a lens effect caused by the primary optical system 72. Herein, L.sub.aB.sub.6 may be used for a chip of the electron gun, which is a rectangular negative electrode and from which a high current can be emitted. Further, the primary optical system 72 may use an electrostatic (or electromagnetic) quadrupole or octopole lens, asymmetric with respect to a rotating axis. This lens, similar to what is called a cylindrical lens, can cause a focusing and a divergence in the X and the Y axes respectively. Such a configuration comprising two or three steps of these lenses to optimize respective lens conditions allows the beam irradiation region on the sample surface to be formed into a rectangular or elliptical shape as desired without any loss of irradiated electrons.

Specifically, in the case of the electrostatic lenses being used, four cylindrical rods may be used. Each two opposite electrodes are made to be equal in potential and reverse voltage characteristics are given thereto.

It is to be appreciated that a lens formed in the shape of a quarter of a circular plate used commonly in the electrostatic deflector, rather than the cylindrical shape, may be used for the quadrupole lens. That case allows for the miniaturization of the lens. The primary electron beam after passing through the primary optical system 72 is forced by the deflecting effect from the Wien filter 723 so as to deflect the trajectory thereof. In the Wien filter 723, the magnetic field is crossed with the electric field at right angles, and only the charged particles satisfying the Wien condition of E=vB are advanced straight ahead, and the orbits of the other charged particles are deflected, where the electric field is E, the magnetic field B, and the velocity of the charged particle v. A force FB by the magnetic field and another force FE by the electric field may be generated against the primary beam, and consequently the primary beam is deflected. On the other hand, the force FB and the force FE are reversely applied to the secondary beam and those forces are cancelled to each other, so that the secondary beam is allowed to go directly forward.

A lens voltage of the primary optical system 72 has been determined beforehand such that the primary beam is formed into an image at the aperture portion of the numerical aperture NA-2. That numerical aperture NA-2 prevents any excess electron beams to be dispersed in the apparatus from reaching to the sample surface and thus prevents charging or contamination in the sample W. Further, since the numerical aperture NA-2 and the cathode lens 724 together form the telecentric electronic optical system, the primary beams that have passed through the cathode lens 724 may turn to be parallel beams, which are irradiated uniformly and similarly against the sample W. That is to say, it accomplishes what is called in an optical microscope, the Koehler illumination.

(SECONDARY BEAM) When the primary bean is irradiated against the sample, secondary electrons, reflected electrons or back-scattering electrons are generated as the secondary beam from the beam irradiated surface of the sample.

The secondary beam passes through the lens while receiving a lens effect from the cathode lens 724.

It is to be noted that the cathode lens 724 is composed of three pieces of electrodes. Among those electrodes, the one at the lowest position is designed to form a positive electric field between the potentials in the sample W side and itself, and to take in electrons (particularly, secondary electrons with smaller directivities) so that the electrons may be efficiently introduced into the lens.

Further, the lens effect takes place in such a way that voltages are applied to the first and the second electrodes of the cathode lens 724 and the third electrode is held to zero potential. On the other hand, the numerical aperture NA-2 is disposed at the focal position of the cathode lens 724, that is, the back focal position with respect to the sample W. Accordingly, the trajectories of electron beams originating from the center of the field of view (out of the axis) also become the parallel beams and pass through the central location in this numerical aperture NA-2 without being kicked out any further.

It is to be appreciated that the numerical aperture NA-2 serves to reduce lens aberrations of the second lens 741-1 to the fourth lens 741-3 for the secondary beams. Those secondary beams having passed through the numerical aperture NA-2 may not affected by the deflecting effect from the Wien filter 723 but may keep on going straight through the filter. It is to be noted that varying the electromagnetic field applied to the Wien filter 723 may allow only electrons having specified energies (for example, secondary electrons, reflected electrons or back-scattering electrons) to be introduced into the detector 761.

If the secondary beam is formed into an image only by the cathode lens 724, the lens effect may be great and an aberration is more likely to occur. Accordingly, the cathode lens 724 may be combined with the second lens 741-1 to perform first image forming. The secondary beam can be formed into an intermediate image on the field aperture NA-3 by the combination of the cathode lens 724 and the second lens 741-1. In that case, since typically the magnification required for the secondary optical system has often been insufficient, the third lens 741-2 and the fourth lens 741-3 are added in the configuration as the lenses for magnifying the intermediate image. The secondary beam is magnified and formed into an image by the third lens 741-2 and the fourth lens 741-3 respectively, which means that the secondary beam is formed into an image three times in this case. It is to be noted that the beam may be focused only once by using both the third lens 741-2 and the fourth lens 741-3 (a total of two times).

In addition, each of the second lens 741-1 to the fourth lens 741-3 should be a lens symmetrical with respect to a rotating axis of the kind referred to as a uni-potential lens or Einzell lens. Each lens is composed of three electrodes, in which typically the outer two electrodes have zero potentials and a voltage applied to the center electrode is used to causes a controlling lens effect. Further, the field aperture NA-3 is located in the intermediate image forming point. The field aperture NA-3, which constrains the field of view to be limited to a required range, similar to a field stop in an optical microscope, for the case of an electron beam, cooperatively blocks any excess beams with the subsequent stages of the third and the fourth lenses 741-2 and 741-3 so as to prevent charging and/or contamination of the detector 761. It is to be noted the magnification can be controlled by varying the lens conditions (the focal distances) of the third and the fourth lenses 741-2 and 741-3.

The secondary beam is magnified and projected by the secondary optical system and formed into an image on the detection plane of the detector 761. The detector 761 comprises a MCP for amplifying an electron, a fluorescent screen for converting the electrons into light, lenses and other optical elements for use as a relay and transmitting an optical image between the vacuum system and external components, and an image sensor (CCD or the like). The secondary beam is formed into an image on the MCP detection plane and amplified, and then the electrons are converted into light signals by the fluorescent screen, which are in turn converted into photoelectric signals by the image sensor.

The control unit 780 reads out the image signal of the sample from the detector 761 and transmits it to the CPU 781. The CPU 781 performs a defect inspection of the pattern by template matching and so forth from the image signal. On the other hand, the stage 50 is adapted to be movable in the X and Y directions by a stage driving mechanism 56. The CPU 781 reads the position of the stage 50 and outputs a drive control signal to the stage driving mechanism 56 to drive the stage 50, allowing for sequential detection and inspection of the images.

Thus, in the inspection apparatus according to the embodiment, since the numerical aperture NA-2 and the cathode lens 724 comprise the telecentric electronic-optical system, therefore the primary beam may be irradiated uniformly against the sample. That is, it accomplishes the Koehler illumination.

Further, as to the secondary beam, since all of the principle beams from the sample W enter the cathode lens 724 at a right angle (parallel to the optical axis of the lens) and pass through the numerical aperture NA-2, therefore the peripheral beam would not be kicked out thus preventing deterioration of image brightness in the periphery of the sample. In addition, although a variation of the energy pertaining to the electrons gives a different focal position, which causes what is called a magnification chromatic aberration (especially for the secondary electrons, since the energies thereof are varied to a great extent, the magnification chromatic aberration is rather great), the arrangement of the numerical aperture NA-2 at the focal position of the cathode lens 724 makes it possible to control the magnification chromatic aberration so that it is kept low.

On the other hand, since a change of the magnification factor is executed after the beam has passed through the numerical aperture NA-2, any changes in the determined magnification factor in the lens condition for the third and the fourth lenses 741-2 and 741-3 can still bring a uniform image over the field of view to be obtained in the detection side. It should be appreciated that although an even and uniform image can be obtained in the present embodiment, typically, increasing the magnification may problematically cause deterioration in the brightness of the image. Accordingly, in order to improve this problematic condition, when the lens condition for the secondary optical system is changed to vary the magnification factor, the lens condition for the primary optical system should be controlled such that the effective field of view on the sample determined in association with the magnification and the electron beam to be irradiated on the sample may be equally sized.

That means, as the magnification is increased, consequently the field of view gets smaller, but when the irradiation beam current of the electron beam is increased at the same time, the signal density of the detected electron can be kept at a constant level and the brightness of the image may be prevented from deterioration even if the beam is magnified and projected in the secondary optical system.

Further, although in the inspection apparatus according to the present embodiment, a Wien filter 723 has been employed, which deflects the trajectories of a primary beam but allows a secondary beam to go straight forward, the application is not limited to this and the apparatus may employ a Wien filter with another configuration in which the primary beam is allowed to go straight forward but the orbit of the secondary beam is deflected. Still further, although in the present embodiment, a rectangular cathode and a quadrupole element lens are used to form a rectangular beam, the application is not limited to this and, for example, a rectangular beam or elliptical beam may be formed from a circular beam, or the circular beam may be passed through a slit to extract the rectangular beam.

Electrode

Between the objective lens 724 and the wafer W, there is disposed an electrode 725 having a shape approximately symmetrical with respect to the optical axis of irradiation of the electron beam. Typical shapes of the electrode 725 are shown in FIGS. 12 and 13.

Figure 12:
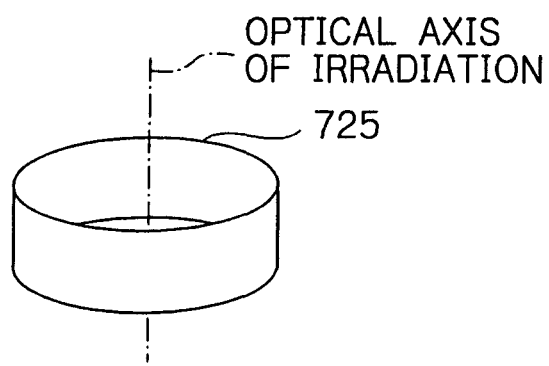
FIG. 12 is a perspective view of an electrodes, wherein the electrode has a cylindrical shape formed to be axis-symmetrical.
Figure 13:
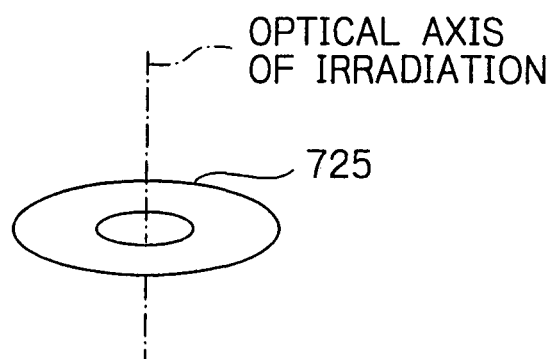
FIG. 13 is a perspective view of an electrode, wherein the electrode has a disk-like shape formed to be axis-symmetrical.

FIGS. 12 and 13 are perspective views of the electrode 725, wherein FIG. 12 is a perspective view of an electrode 725 with a cylindrical shape formed to be axially symmetrical, while FIG. 13 is a perspective view of another electrode 725 with a disk-like shape formed to be axially symmetrical.

Although in this embodiment, the explanation is made for the case where the electrode 725 is cylindrical in shape as shown in FIG. 12, the electrode may have a disk-like shape as shown in FIG. 13 so far as it is approximately symmetrical with respect to the optical axis of irradiation of the electron beam.

Further, in order to generate the field which is to prevent an electric discharge between the objective lens 724 and the wafer W, a predetermined voltage (negative potential) lower than that applied to the wafer W (the potential thereof is 0V since the wafer is grounded in this embodiment) is applied to the electrode 725 by the power supply 726. The potential distribution between the wafer W and the objective lens 724 at this point in time will be described with reference to FIG. 14.

Figure 14:
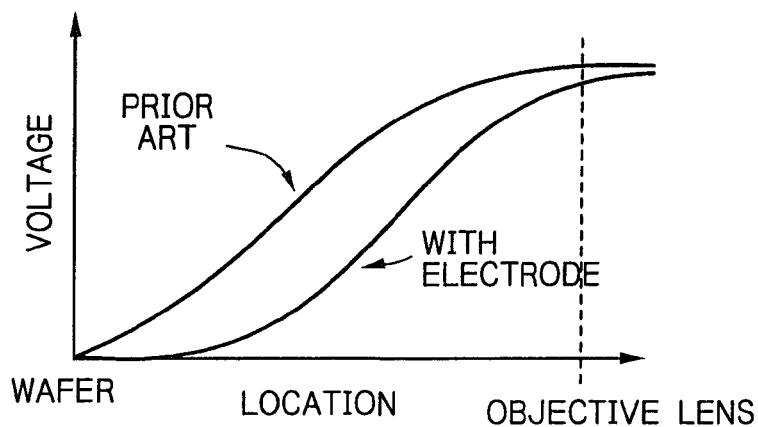
FIG. 14 is a graph illustrating a voltage distribution between a wafer and an objective lens.

FIG. 14 is a graph of the voltage distribution between the wafer W and the objective lens 724.

In FIG. 14, the voltage distribution is shown over a range from the wafer W to the objective lens 724 along the optical axis of irradiation of the electron beam, indicating the position on the optical axis by the horizontal axis.

The voltage distribution from the objective lens 724 to the wafer W for the prior art with no electrode 725 is shown to vary gently from the maximum value of the voltage applied to the objective lens 724 to the wafer W that has been grounded (as shown with the thinner line in FIG. 14).

In contrast, for the electron beam apparatus according to the present invention, since the electrode 725 is arranged between the objective lens 724 and the wafer W, and further the electrode 725 is supplied with a predetermined voltage (negative potential) lower than that applied to the wafer W from the power supply 726, the electric field of the wafer W is weakened (as shown with the thicker line).

Therefore, with the electron beam apparatus of the present invention, the electric field could not be dense in the vicinity of the via b in the wafer W, so that there is no strong electric field. Accordingly, even if there is an emission of secondary electrons emitted by the electron beam irradiated onto the via b, these emitted secondary electrons would not be accelerated enough to ionize the residual gas, so that electric discharge may be prevented between the objective lens 724 and the wafer W.

Further, since electric discharge is prevented between the objective lens 724 and the wafer W, there would be no damage to the pattern in the wafer W, which otherwise would be caused by an electric discharge.

On the other hand, although in the above embodiment, the electric discharge can be prevented between the objective lens 724 and the wafer W having the via b, the detection sensitivity of the detector 761 to the secondary electrons may possibly decrease depending on the level of the negative potential applied to the electrode 725. Accordingly, it is suggested that in the case of a decrease in the detection sensitivity, a series of operations including the irradiation of the electron beam and the detection of the secondary electrons should be repeated a plurality times, and the obtained number of detection results are processed with an accumulative addition or averaging operation to obtain a desired sensitivity (S/N ratio of the signal).

In the present invention, the detection sensitivity, for the purpose of explanation, is exemplarily defined as a signal to noise ratio (S/N ratio).

The above described operation for detecting secondary electrons will now be described with reference to FIG. 15.

Figure 15:
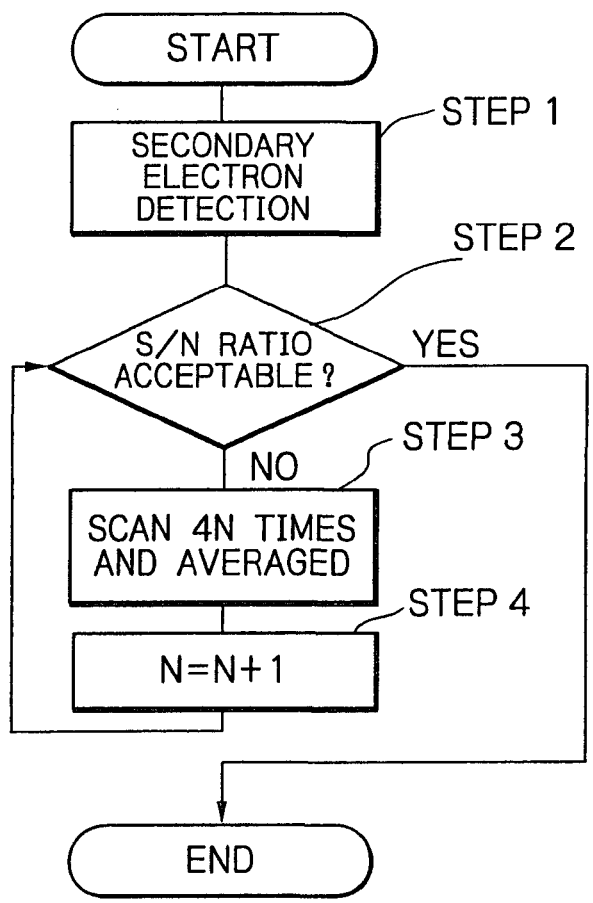
FIG. 15 is a flow chart for the secondary electron detecting operation of an electron beam apparatus.

FIG. 15 is a flow chart illustrating the operation for detecting secondary electrons in the electron beam apparatus.

Primarily, the secondary electrons from the sample to be inspected are detected by the detector 761 (Step 1). Then, a determination is made on whether or not the signal to noise ratio (the S/N ratio) is equal to or greater than a predetermined value (Step 2). At step 2, if the signal to noise ratio is equal to or greater than the predetermined value, then the detecting operation by the detector 761 for the secondary electrons is determined to be sufficient, and the secondary electron detecting operation is completed.

On the contrary, if the signal to noise ratio is lower than the predetermined value at step 2, a series of operations comprising the irradiation of the electron beam and the detection of the secondary electrons is repeated 4N times and the results are averaged (Step 3). At that time, since the initial value for N has been set to "1", therefore the secondary electron detecting operation should be performed 4 times for the first time at step 3.

Then, N is incremented by "1" for counting up (Step 4), and again at step 2 a determination is made on whether or not the signal to noise ratio is equal to or greater than the predetermined value. If the signal to noise ratio is again lower than the predetermined value, the process goes to step 3 again, and this time, the detecting operation of the secondary electrons should be repeated 8 times. Then N is incremented and the steps 2 to 4 should be repeated until the signal to noise ratio is equal to or greater than the predetermined value.

Further in this embodiment, although the explanation is given for the case where the electric discharge to the wafer W having the via b may be effectively prevented by applying to the electrode 725 a predetermined voltage (a negative potential) lower than that applied to the wafer 8, there would be another case where the detection sensitivity to the secondary electrons is disadvantageously decreased.

Accordingly, if the sample to be inspected is a wafer having no vias or the like, which is of a kind in which electric discharge is less likely to occur between itself and the objective lens 724, then the voltage applied to the electrode 725 may be controlled so that the efficiency of detection of secondary electrons can be increased.

Specifically, even in the case where the sample to be inspected is grounded, a voltage applied to the electrode 725 may be set to a predetermined voltage higher than that applied to the sample to be inspected, for example, the voltage of +10 V. Further, at that time, the distance between the electrode 725 and the sample to be inspected should be determined to be enough that the electric discharge would not occur between the electrode 725 and the sample to be inspected.

In this case, the secondary electrons generated by the irradiation of the electron beam onto the sample to be inspected is accelerated toward the side of the electron beam source 721 by the electric field generated by the voltage applied to the electrode 725. Then, the secondary electrons are further accelerated by the electric field generated by the voltage applied to the objective lens 724 toward the side of the electron beam source 721 to be subject to the convergent effect, resulting in many electrons entering the detector 761, thus increasing the detection efficiency.

Still further, since the electrode 725 is axially symmetrical, it also serves as a lens to converge the electron beam irradiated to the sample to be inspected. Therefore, by controlling the voltage applied to the electrode 725, the primary electron beam can be converged to be narrower. Further, since the primary electron beam can also be converged to be narrower by way of the electrode 725, an objective lens system having lower aberration can be constructed by means of the combination of the objective lens 724 and the electrode 725. The electrode 725 may be approximately axially symmetrical so long as such lens action can be obtained.

According to an electron beam apparatus of the subject embodiment, since an electrode having a shape approximately symmetrical with respect to the axis of irradiation of the electron beam has been arranged between the sample to be inspected and the objective lens so as to control the electric field intensity in the electron beam irradiated plane of the sample to be inspected, therefore the electric field between the sample to be inspected and the objective lens can be controlled.

Further, since an electrode having a shape approximately symmetrical with respect to the axis of irradiation of the electron beam has been arranged between the sample to be inspected and the objective lens so as to weaken the electric field intensity in the electron beam irradiated plane of the sample to be inspected, the electric discharge between the sample to be inspected and the objective lens can be eliminated.

Since there has been no modification such as decreasing the voltage applied to the objective lens and therefore the secondary electrons can go through the objective lens efficiently, the detection efficiency can be improved and a signal with good S/N ratio can be obtained.

Further, the voltage can be controlled so as to weaken the electric field intensity in the electron beam irradiated plane of the sample to be inspected, depending on the category of the sample to be inspected.

For example, if the sample to be inspected is of a type likely to cause an electric discharge between the objective lens and itself, the electric discharge can be prevented by weakening the electric field intensity in the electron beam irradiated plane of the sample to be inspected by changing the voltage applied to the electrode.

Further, the voltage applied to the electrode can be changed depending on whether or not said semiconductor device has a via, that is, the voltage applied in order to weaken the electric field intensity in the electron beam irradiated plane of the semiconductor wafer can be changed.

For example, if the sample to be inspected is of a type that is likely to cause an electric discharge between the objective lens and itself, the electric discharge especially in the via or in the vicinity of the via can be prevented by changing the electric field generated by the electrodes, thereby weakening the electric field intensity in the electron beam irradiated plane of the sample to be inspected.

Further, since the electric discharge is prevented between the via and the objective lens, there would be no damage to the pattern or the like in the semiconductor wafer, which otherwise would be caused by the electric discharge.

Further, since the potential applied to the electrode has been made lower than that applied to the sample to be inspected, the electric field intensity in the electron beam irradiated plane of the sample to be inspected can be weakened, thus preventing the electric discharge to the sample to be inspected.

Yet further, since the potential applied to said electrode is a negative potential and the sample to be inspected is grounded, the electric field intensity can be weakened in the electron beam irradiated plane of the sample to be inspected, thus preventing the electric discharge to the sample to be inspected.

Modified Embodiment of E.Times.B Separator

Figure 16:
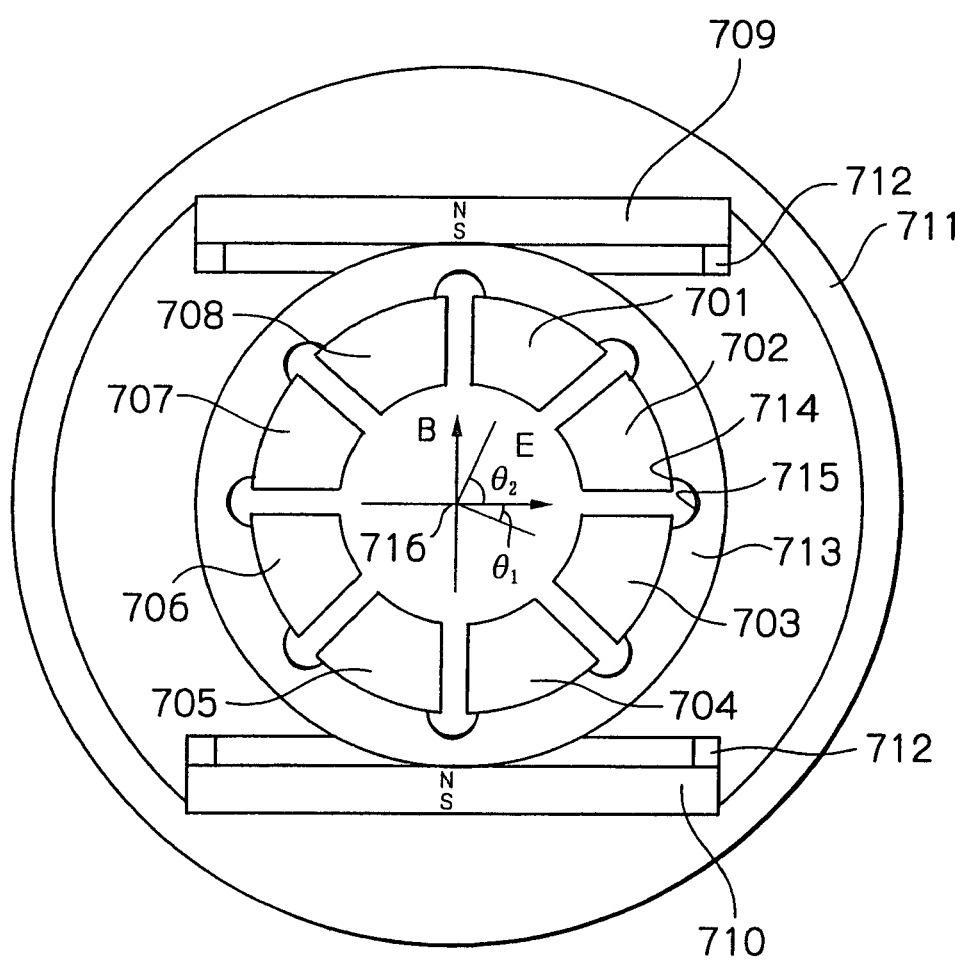
FIG. 16 is a cross sectional view of an E.times.B separator according to the present invention.

FIG. 16 shows an E.times.B separator of an embodiment according to the present invention. FIG. 16 is a cross sectional view taken along a plane normal to an optical axis. Four pairs of electrodes 701 and 708, 702 and 707, 703 and 706, and 704 and 705 used for generating an electric field are made of a non-magnetic conductive material, together forming an approximately cylindrical shape as a whole, and fixedly secured with screws or the like (not shown) on an inner face of a cylinder 713 made of insulating material for supporting the electrodes. An axis of the cylinder 713 for supporting the electrodes and an axis of the cylinder formed by the electrodes are made identical with the optical axis 716. A plurality of grooves 714 is respectively arranged on the inner face of the electrode supporting cylinder 713 in parallel with the optical axis 716 in each space between the electrodes 701, 702, 703, 704, 705, 706, 707, and 708. Then, the inner face areas of said grooves are coated with conductive material 715, and are set to the ground potential.

Figure 17:
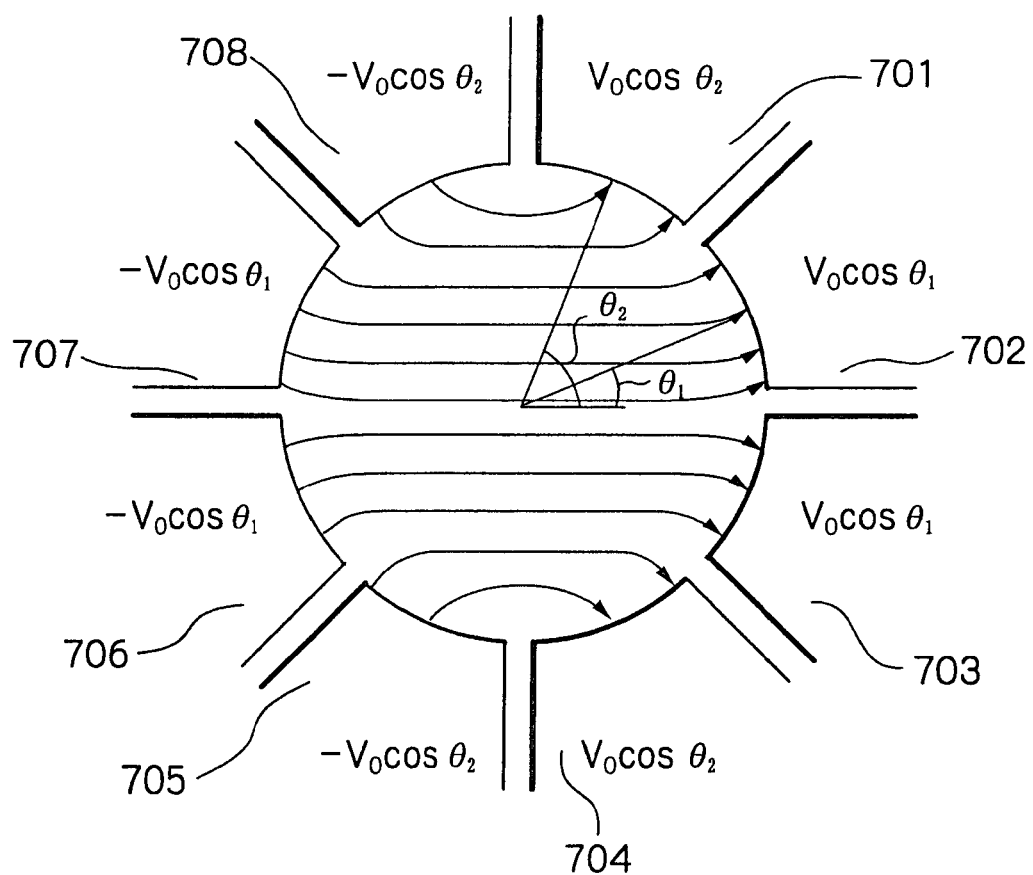
FIG. 17 is a diagram illustrating the electric field distribution of the E.times.B separator according to the present invention.

Upon generating the electric field, if the voltages are applied respectively to the electrodes in such a manner that a voltage proportional to "cos .theta..sub.1" is applied to the electrodes 702 and 703, "−cos .theta..sub.1" to the electrodes 706 and 707, "cos .theta..sub.2" to the electrodes 701 and 704, and "−cos .theta..sub.2" to the electrodes 705 and 708, there emerges an electric field that has a uniform and parallel pattern over a region equivalent to approximately 60% of the region within the inner diameter of the electrodes. FIG. 17 shows a simulation result for the electric field distribution. It should be noted that although this example uses four pairs of electrodes, even with three pairs of electrodes a uniform and parallel pattern of the electric field can be obtained for the region equivalent to approximately 40% of the region within the inner diameter.

The generation of the magnetic field is accomplished by placing two rectangular permanent magnets made of platinum alloy 709 and 710 in parallel outside the electrode supporting cylinder 713. Projections 712 made of magnetic material are arranged in peripheral portions of the permanent magnets 709 and 710 in the sides facing the optical axis 716. These projections 712 are arranged to compensate for the outwardly convex distortion of the lines of magnetic force in the sides facing the optical axis 716, and the size and shape of the projection may be determined based on the simulation analysis.

The exterior of the permanent magnets 709 and 710 is provided with a magnetic circuit 711 made up of ferromagnetic material so that the passage for the lines of magnetic force by the permanent magnets 709 and 710 in the opposite side to the optical axis 716 is formed to be a cylindrical shape that is coaxial with the electrode supporting cylinder 713.

The E.times.B separator as shown in FIG. 16 is also applicable to a scanning type electron beam inspection apparatus as well as a projective electron beam inspection apparatus as shown in FIG. 8.

As is apparent from the above description, according to the subject embodiment, both the electric field and the magnetic field are allowed to emerge uniformly in the larger region around the optical axis, so that even if the area exposed to the irradiation of the primary electron beam is extended, the aberration for the image passed through the E.times.B separator would fall into a reasonable range of values.

Since the projections have been arranged in the peripheral portions of the magnetic poles generating the magnetic field, and also said magnet poles are arranged outside of the electrodes for generating the electric field, it allows a uniform magnetic field to be generated and distortion by the magnetic poles to be reduced. Further, since the magnetic field has been generated by use of the permanent magnets, the E.times.B separator can be fully installed in a vacuum. Still further, the electrodes for generating the electric field and the magnetic circuit for forming the magnetic path have been formed into coaxial cylindrical shapes centered on the optical axis, which makes it possible to reduce in size the E.times.B separator as a whole.

Precharge Unit

The precharge unit 81, as illustrated in FIG. 1, is disposed adjacent to the column 71 of the electron-optical system 70 within the working chamber 31. Since this inspection apparatus is configured to inspect device patterns or the like formed on the surface of a substrate or a wafer to be inspected by irradiating the wafer with an electron beam, so that the secondary electrons generated by the irradiation of the electron beam are used as information on the surface of the wafer. However, the surface of the wafer may be charged up depending on conditions such as the wafer material, energy of the irradiated electrons, and so on. Further, on the surface of a single wafer, some regions may be highly charged, while other regions may be lightly charged. Variations in the amount of charge on the surface of the wafer cause corresponding variations in information provided by the resulting secondary electrons, thereby failing to provide correct information. For preventing such variations, in this embodiment, the precharge unit 81 is provided with a charged particle irradiating unit 811. Before electrons for inspection are irradiated to a predetermined region on a wafer to be inspected, charged particles are irradiated from the charged particle irradiating unit 811 of the precharge unit 81 to eliminate variations in charge. The charges on the surface of the wafer may be detected by previously forming an image of the surface of the wafer to be inspected, and by evaluating the image, and the precharge unit 81 can be operated based on such detection.

Alternatively, the precharge unit 81 may be operated while blurring the primary electron beam.

Figure 18:
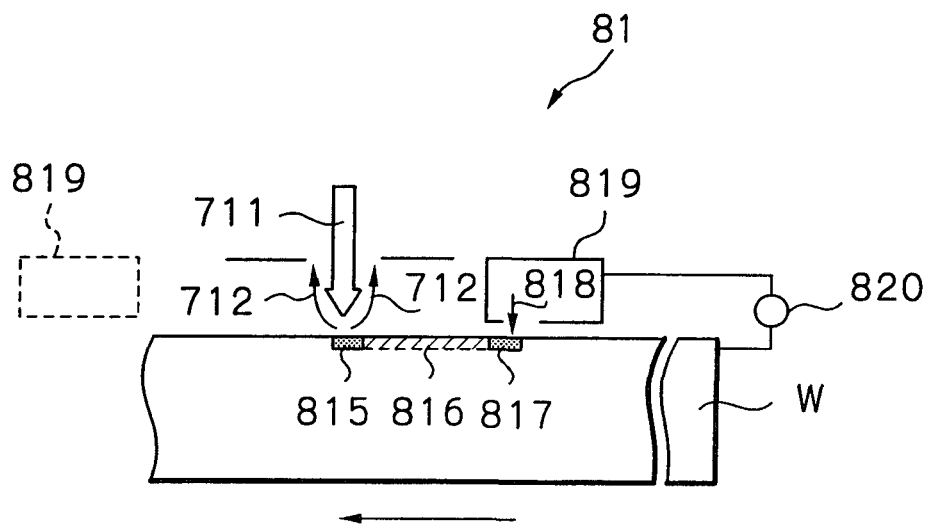
FIG. 18 is a schematic diagram of the main components of the precharge unit of an embodiment according to the present invention.

FIG. 18 shows the main components of a precharge unit of an embodiment according to the present invention.

Charged particles 818 from a charged particle irradiation source 819 are accelerated with a voltage determined by a bias supply 820 so as to be irradiated onto a sample substrate W. An inspecting region 815, and a region 816 as well, are indicated as locations that have been already exposed to the charged particle irradiation for a pre-treatment, and the region 817 is indicated as a location which is currently exposed to the charged particle irradiation. In this drawing, although the sample substrate W is shown to be scanned in the direction indicated with an arrow, another charged particle beam source 819 may be arranged on the opposite side to the first electron beam source as shown with the dotted line in the drawing, so that the charged particle beam sources 819 and 819 may be alternately turned on and off in synchrony with the direction of the scanning of the sample W. In this case, if the energy of the charged particles is too high, the secondary electron 712 yield from an insulating portion of the sample substrate W would exceed 1, thus causing the surface to be positively charged, and even a yield of not more than 1 would still make the phenomenon complicated with the generated secondary electrons thus decreasing the irradiation effect, and accordingly, it is preferred that the voltage for the energy of the charged particles should be set to a landing voltage of 100 eV or lower (preferably higher than 0 eV and lower than 30 eV), which can significantly reduce the generation of the secondary electrons.

Figure 19:
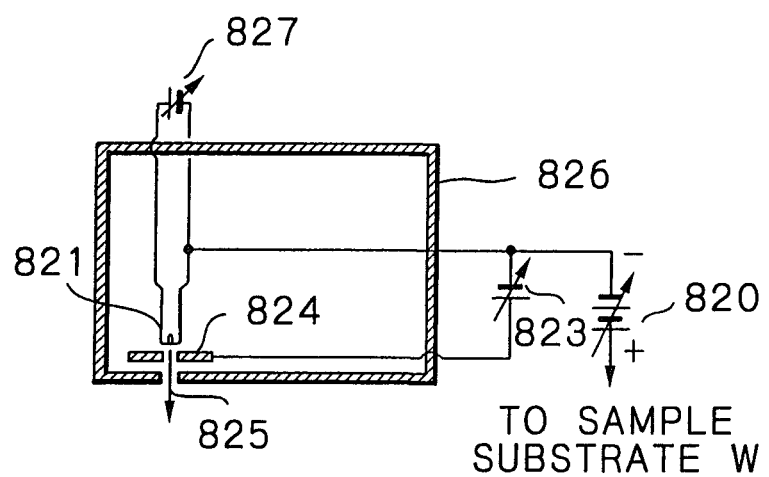
FIG. 19 is a schematic diagram of a precharge unit of another embodiment according to the present invention.

FIG. 19 shows a second embodiment of a precharge unit of the present invention. FIG. 19 shows an irradiation source of such type that irradiates an electron beam as a charged particle beam. The irradiation source comprises a hot filament 821, a deriving electrode 824, a shield case 826, a filament power supply 827, and an electron deriving power supply 823. The deriving electrode 824 is 0.1 mm in thickness, has a slit 0.2 mm wide and 1.0 mm long, and is arranged relative to the filament 821 of a diameter of 0.1 mm so as to take the form of a three-electrode type electron gun. The shield case 826 is also provided with a slit of 1 mm wide and 2 mm long, and is assembled so that the shield case 826 is spaced from the deriving electrode 824 by 1 mm with its slit center being aligned with the slit center of the deriving electrode 824. The filament is made of tungsten (W), and it is found that an electron current of in the order of .mu.A can be obtained with a current of 2 A being supplied to the filament when a deriving voltage of 20 V and a bias voltage of −30 V are applied.

The example has been shown for illustrative purposes only and the filament may be made of other materials, for example, a high melting point metal such as Ta, Ir, Re or the like, thoria-coated W, or an oxide electrode, and in this case, needless to say, the filament current should be varied depending on the material, the line diameter and the line length to be used. Further, other kinds of electron guns may be used as long as the electron beam irradiated area, the electron current and the energy can be respectively set to appropriate value.

Figure 20:
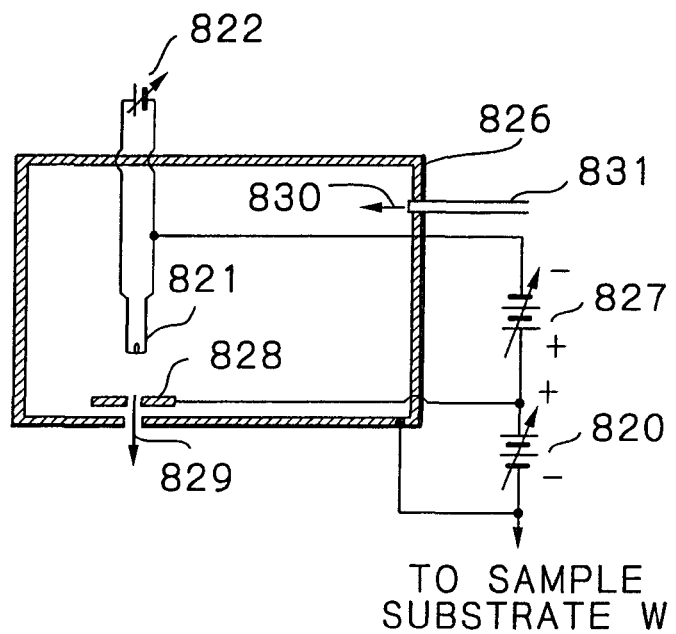
FIG. 20 is a schematic diagram of the precharge unit of still another embodiment according to the present invention.

FIG. 20 shows a third embodiment of a precharge unit of the present invention. FIG. 20 shows an irradiation source of a type that irradiates ions 829 as a charged particle beam. This irradiation source comprises a filament 821, a filament power supply 822, an electric discharge power supply 827, and an anode shield case 826, in which both of anode 828 and the shield case 826 have the same sized slit of 1 mm.times.2 mm respectively formed therethrough, and they are assembled so that the centers of both slits are aligned with each other. Ar gas 830 is introduced into the shield case 826 through a pipe 831 with about 1 Pa and this irradiation source is operated by way of an arc discharge caused by the hot filament 821. The bias voltage is set to a positive value.

Figure 21:
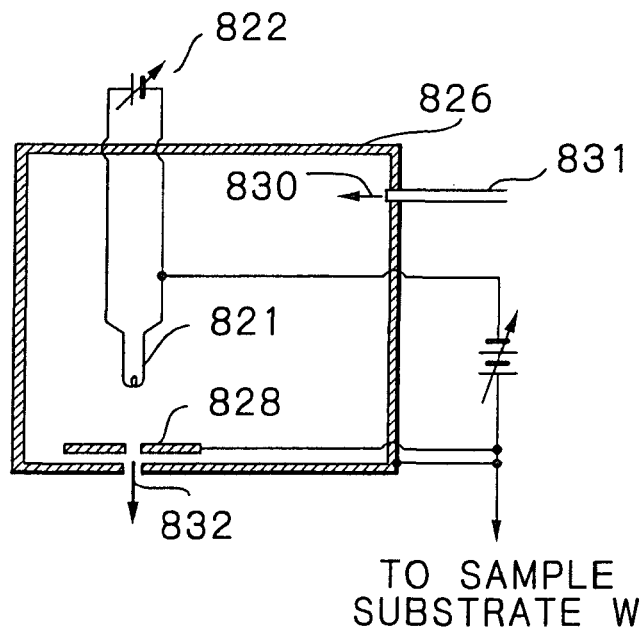
FIG. 21 is a schematic diagram of the precharge unit of yet another embodiment according to the present invention.

FIG. 21 shows a plasma irradiation type of a fourth embodiment of a precharge unit according to the present invention. It has the same structure as that of FIG. 20. The operation thereof, similarly to the above description, is made effective by way of the arc discharge by the hot filament 821, in which by setting the bias potential to 0V, the plasmas 832 are forced by gas pressure to effuse through the slit to be irradiated onto a sample substrate. Since in the plasma irradiation method, the beam is composed of a group of particles that has both positive and negative charges, which is different from the other irradiation methods, it allows both positive and negative surface potentials in the surface of the sample substrate to approach zero.

A charged particle irradiating section 819 arranged in the proximity of the sample substrate W has a configuration as illustrated in any of FIGS. 18 to 21, which is designed to irradiate charged particles 818 onto the sample substrate with a suitable condition depending on the difference in the surface structure, e.g., silicon dioxide film or silicon nitride film, of the sample W, or depending on a different requirement for each sample substrate after respective different processes, and in which after performing the irradiation to the sample substrate under the optimal irradiation condition, that is, after smoothing the potential in the surface of the sample substrate W or saturating the potential therein with the charged particles, an image is formed by the electron beam 711 and 712 to be used to detect any defects.

As described above, since according to the subject embodiment, pre-treatment by means of charged particle irradiation is employed just before measurement and thereby an evaluated image distortion by the charging would not occur or would be negligible, any defects can be accurately detected.

Further, according to the embodiment according to the present invention, since a high current is allowed to be used for scanning a stage by an amount that has caused problems in the prior art, a large number of secondary electrons can be detected and a detection signal having a good S/N ratio can be obtained, thus improving the reliability of defect detection.

Still further, with a larger S/N ratio, faster scanning of the stage still can produce good image data, thus allowing inspection throughput to be greater.

Figure 22:
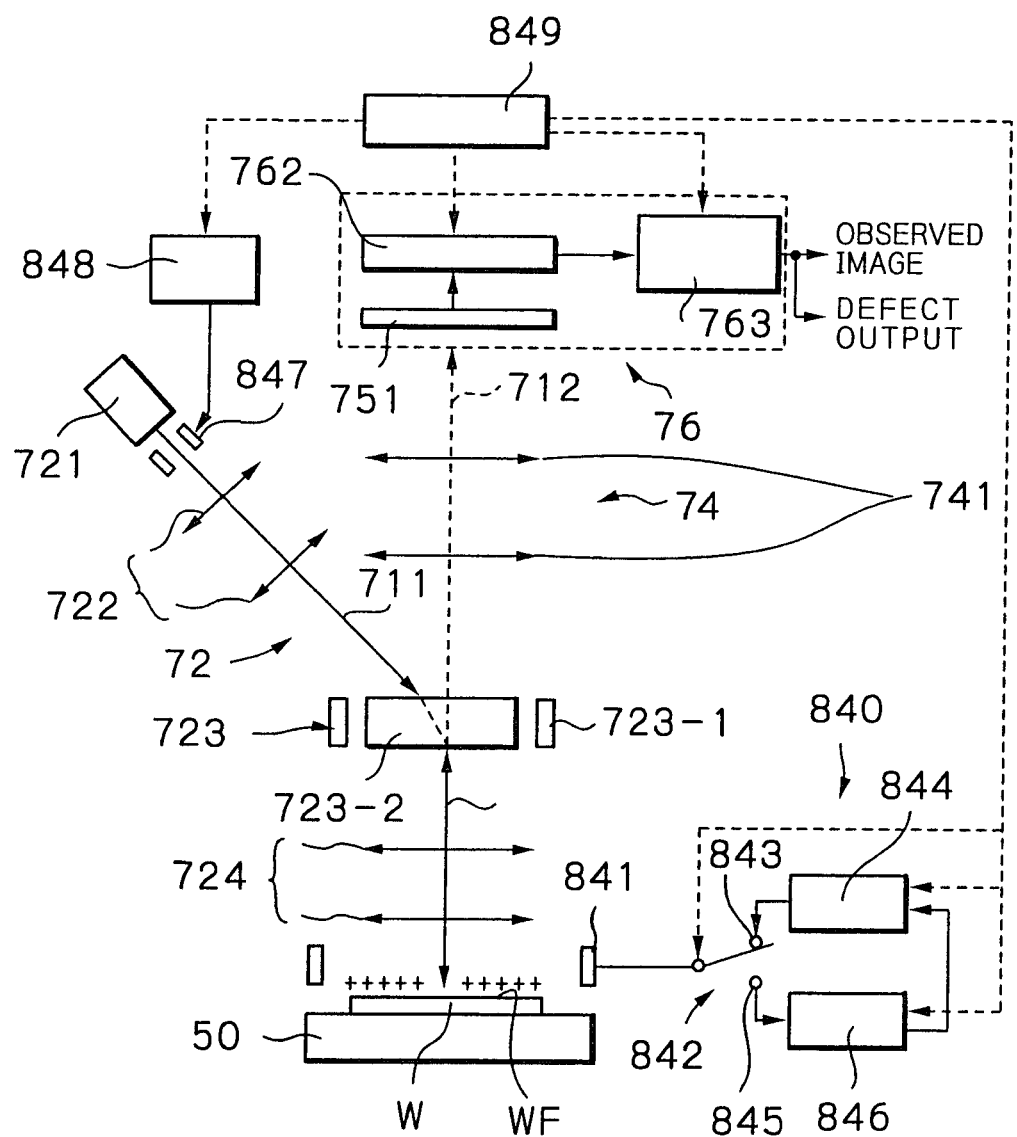
FIG. 22 is a schematic diagram illustrating an imaging apparatus of one embodiment according to the present invention.

FIG. 22 schematically shows an imaging apparatus equipped with a precharge unit according to the present embodiment. The imaging apparatus comprises a primary optical system 72, a secondary optical system 74, a detecting system 76 and an electric charge control means 840 for uniforming a distribution or reducing a potential level of electric charge residing on an object. The primary optical system 72 is an optical system for irradiating an electron beam or a charged particle beam against the surface of an object to be inspected (hereafter referred to as an object) "W", and comprises: an electron gun 721 for emitting the electron beam; electrostatic lenses 722 for respectively focusing and contracting a primary electron beam 711 emitted from the electron gun 721; a Wien filter or an E.times.B separator 723 for deflecting the primary electron beam so that the optical axis thereof may be normal to the surface of the object; and electrostatic lenses 724 for respectively focusing and magnifying the electron beam, wherein those components are arranged in the order as illustrated in FIG. 22, with the electron gun 721 being disposed in the topmost location and the optical axis of the primary electron beam 711 emitted from the electron gun being inclined with respect to the line normal to the surface of the object W (i.e., the sample surface). The E.times.B deflecting system 723 comprises an electrode 723-1 and a magnet 723-2.

The secondary optical system 74 comprises electrostatic lenses 741 each disposed above the E.times.B deflecting system 723 of the primary optical system. The detecting system 76 comprises a combination 751 of a scintillator and a microchannel plate (MCP) for converting a secondary electron 712 into an optical signal, a CCD 762 for converting the optical signal into an electric signal, and an image processing unit 763. The structures and functions of these components in the above-mentioned primary optical system 72, secondary optical system 74 and detecting system 76 are all similar to those according to the prior art, and detailed description thereof will be omitted.

In this embodiment, an electric charge control means 840 for uniforming a distribution or reducing the potential level of electric charge residing on an object comprises an electrode 841 disposed in proximity to the object W between the object W and the electrostatic deflecting lens 724 of the primary optical system 72 located most closely to the object W, a change-over switch 842 electrically connected to the electrode 841, a voltage generator 844 electrically connected to one terminal 843 of the change-over switch 842, an electric charge detector 846 electrically connected to the other terminal 845 of the change-over switch 842. The electric charge detector 846 has a high level of impedance. The electric charge reducing means 840 further comprises a grid 847 disposed between the electron gun 721 and the electrostatic lens 722 of the primary optical system, and a voltage generator 848 electrically connected to the grid 847. A timing generator 849 functions to give commands on the operational timings to the CCD 762 and the image processing unit 763 of the detecting system 76, and the change-over switch 842, and the electric charge detectors 846 and 848 of the electric charge reducing means 840.

The operation of the electron beam apparatus with the above configuration will now be described.

A primary electron beam 711 emitted from the electron gun 721 passes trough the electrostatic lenses 722 of the primary optical system 72 and reaches up to the E.times.B deflecting system 723, where the beam 711 is deflected to be normal to the surface of the object W by the E.times.B deflecting system 723, and then further goes through the electrostatic deflectors 724 to be irradiated onto the surface (the objective surface) WF of the object W. The secondary electrons emanate from the surface WF of the object W depending on the properties of the object. This secondary electrons 712 are sent to the combination of scintillator and MCP 751 of the detecting system 76 via the electrostatic lenses 741 of the secondary optical system 74 and converted into light by the scintillator, which light is photo-electrically converted by the CCD 762, and the converted electric signal is used by the image processing unit 763 to form a two dimensional image (having a gradation). It is to be appreciated that, in any typical inspection apparatus of this kind, the primary electron beam to be irradiated against the object is adapted to be irradiated onto the objective surface WF covering all of the desired locations so as to collect data on that objective surface either by performing a scanning operation with the primary electron beam by the known deflecting means (not shown), by moving a table T carrying the object thereon in the two dimensional directions X and Y, or by the combination of those movements.

The primary electron beam 711 irradiated onto the object W electrifies the object W on the vicinity of the surface thereof to be positively charged. As a result, the secondary electrons 712 emanating from the surface WF of the object W are forced by Coulomb forces associated with this electric charge to change their trajectory thereof depending on the condition of the electric charge. This results in a distortion occurring in the image formed in the image processing unit 763. Since the electric charging of the objective surface WF depends on the properties of the object W, therefore in the case of a wafer having been employed as the object, the electric charging of the surface is not necessarily the same even on the same wafer and further it is variable as time passes. Accordingly, there might be a risk of error in detection when the two patterns in the different two locations on the wafer are compared.

In this viewpoint, in the embodiment of the present invention, the electric charge detector 846 having a high level of impedance utilizes an idle time after the CCD 762 of the detecting system 76 has captured an image for one scanning in order to measure the amount of the electric charge of the electrode 841 located in the proximity of the object W. Then the power source 844 is invoked to generate a voltage sufficient to irradiate electrons corresponding to the measured amount of electric charge, and after measurement the change-over switch 842 is actuated to connect the electrode 841 to the power source 844, so that the voltage generated by the power source 844 may be applied to the electrode 841 to offset the potential level of the charging. This prevents the distortion from occurring in the image formed in the image processing unit 763. Specifically, while a regular voltage is applied to the electrode 841, a focused electron beam may be irradiated against the object W, and in contrast once another voltage is applied to the electrode 841, which causes the focusing condition to vary greatly, an irradiation may be carried out with smaller current density covering a wide area expected to be charged, so as to neutralize the positive charging on the object and to thereby uniform the potential of the wide area expected to be charged to a specific positive (or negative) value or the potential of the wide area is reduced to a lower positive (or negative) value (including 0V) by uniforming and reducing the positive charging on the object. Such an offset operation as described above may be carried out for each scan.

Figure 23:
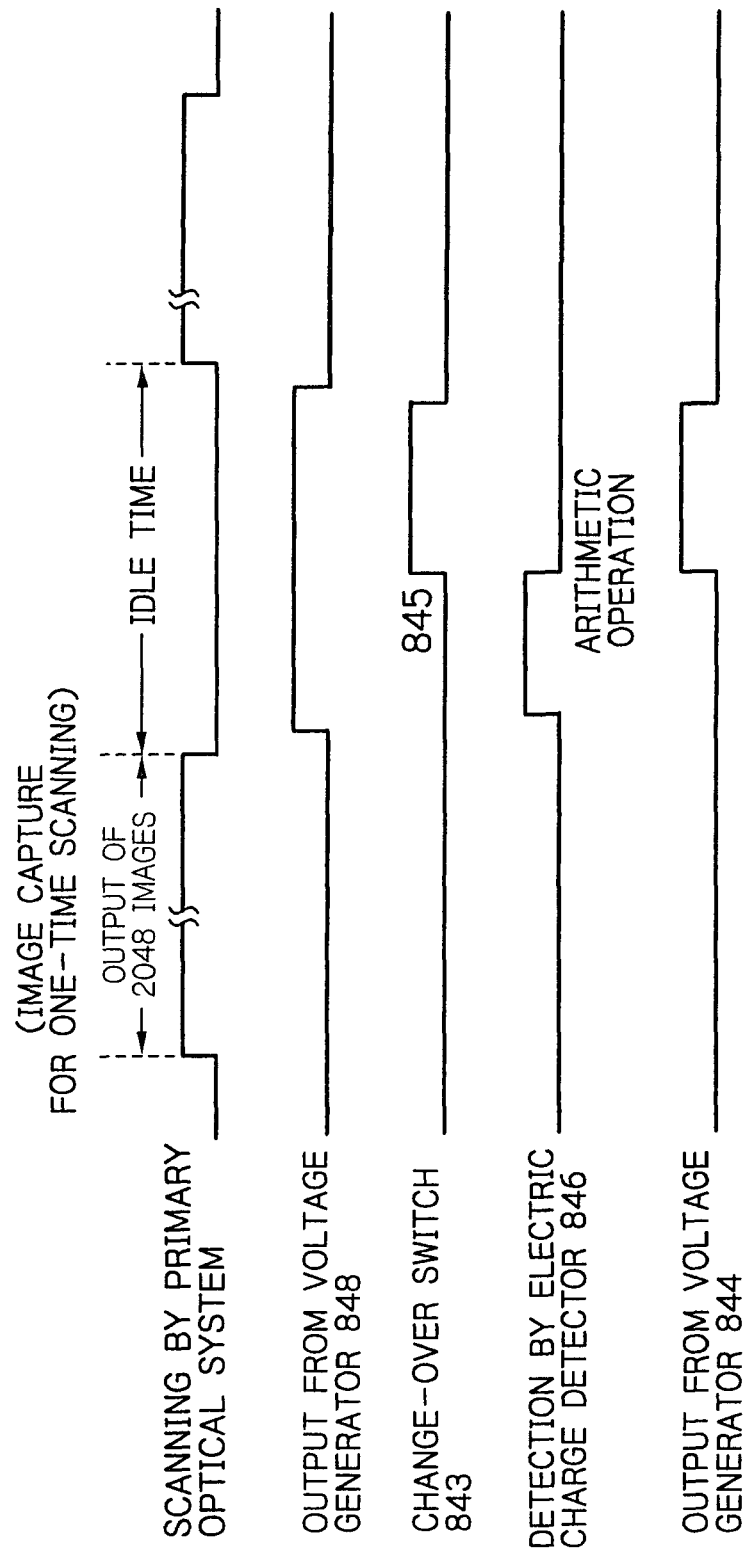
FIG. 23 is a chart illustrating operational timings for uniforming a distribution or reducing the potential level of electric charge residing on an object in the imaging apparatus of FIG. 22.

The Whehnelt electrode or the grid 847 has the function of stopping the electron beam to be irradiated from the electron gun 721 during the timing of the idle time so as to stably carry out measurement of the charging amount as well as the offset operation of the charging. The timings for the above-described operations may be commanded by the timing generator 849, which are illustrated in the timing chart of FIG. 23. It is to be noted that since the charging amount may be varied depending on the locations in the case of a wafer being used as an object, a plurality of groups composed of the electrodes 841, the change-over switches 842, the voltage generators 844 and the electric charge detectors 846 may be arranged along a scanning direction so as to subdivide the area on the object and to accomplish control with much higher precision.

According to the embodiment according to the present invention of the invention, the following effects may be expected to obtain:

(A) distortion in an image caused by the charging may be reduced with no regard to the properties of an object to be inspected;

(B) since idle time between the timings for the conventional measurement is used to execute the uniforming and offsetting of the charging, there will be no effect on throughput;

(C) since real-time processing becomes possible, a time for any post-processing, a memory and the like are no longer necessary; and, (D) fast and highly accurate observation of an image and detection of defects may be accomplished.

Figure 24:
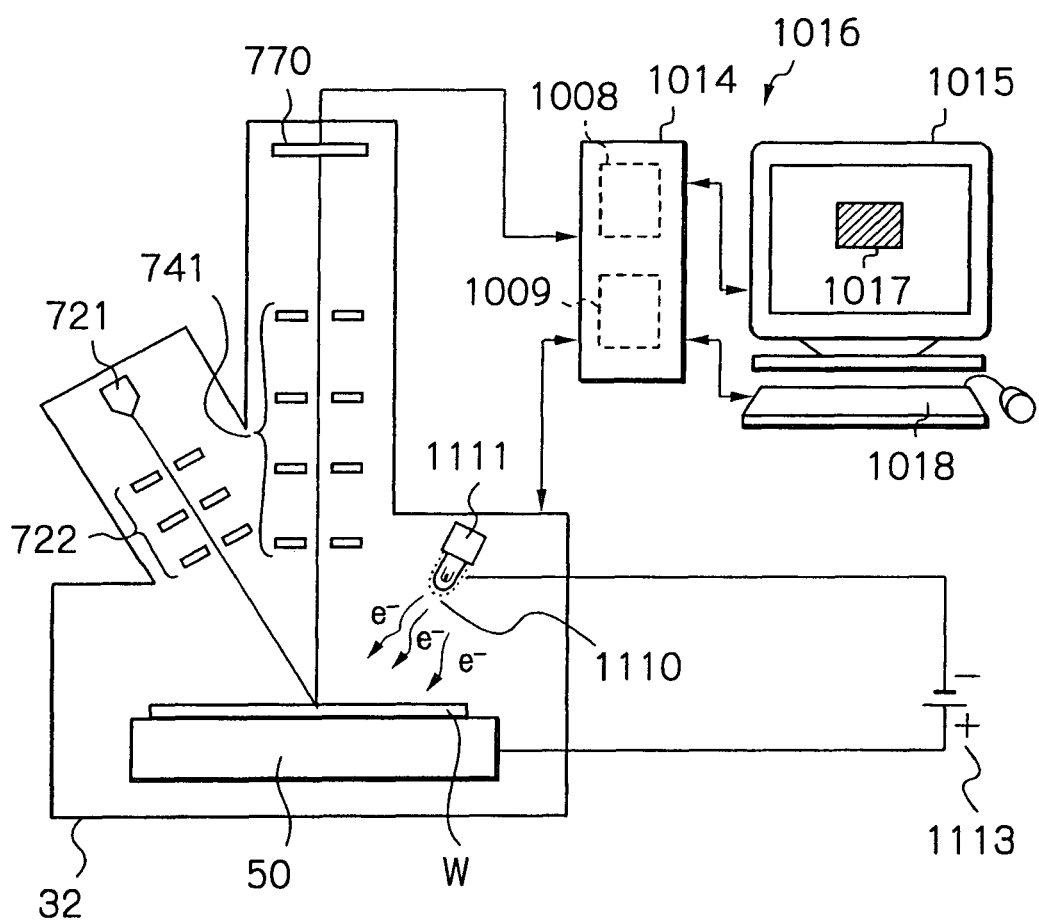
FIG. 24 is a schematic diagram of a defect inspection apparatus equipped with a precharge unit according to another embodiment of the present invention.

FIG. 24 shows a general configuration of a defect inspection apparatus equipped with a pre-charge unit according to another embodiment of the present invention. The defect inspection apparatus comprises: an electron gun 721 for emitting a primary electron beam; an electrostatic lens 722 for deflecting the emitted primary electron beam to be appropriately formed; a sample chamber 32 capable of being evacuated to vacuum by a pump (not shown); a stage 50 disposed in the sample chamber and capable of being moved in a horizontal plane with a sample such as a semiconductor wafer W or the like loaded thereon; an electrostatic lens 741 of a projecting system for projecting at a specified magnification a secondary electron beam emanated from the wafer W and/or a reflected electron beam caused by an irradiation of the primary electron beam thereto, thereby forming an image; a detector 770 for detecting a formed image as a secondary electron image of the wafer W; and a control section 1016 for performing a processing of detecting a defect in the wafer W based on the secondary electron image detected by the detector 770 as well as for controlling the overall apparatus. It is to be appreciated that the above-described secondary electron image includes a contribution not only from the secondary electrons but also from the reflected electrons, though herein it is only referred to as the secondary electron image.

Further, in the sample chamber 32, there is provided an UV lamp 1111 mounted above the wafer W, which emits a beam of light in a wave length range including ultra-violet ray. A glass surface of the UV lamp 1111 is coated with a photo-electron emission material 1110 for emitting a photoelectron "e.sup.−" resulting from photoelectric effect caused by the beam emitted from the UV lamp 1111. Any light source may be employed for the UV lamp 1111 so far as it can emit a beam in a wave length range capable of causing the photoelectron emission material 1110 to emit the photoelectrons. Generally, it is advantageous from a viewpoint of cost to employ a low-pressure mercury lamp capable of emitting ultra-violet ray of 254 nm wave length. Further, the photoelectron emission material 1110 may be selected from any arbitrary metals as far as it has an ability to emit photoelectrons and, for example, "Au" may be preferable.

The above-described photoelectron has energy lower than that of the primary electron beam. Herein, the lower energy means the energy in the order of some eV to some ten eV, preferably 0 eV-10 eV. The present invention may employ any arbitrary means for generating those electrons having such lower energy. For example, the present invention may be accomplished also by employing a lower energy electron gun (not shown), in place of the UV lamp 1111.

Further, the defect inspection apparatus of the present embodiment comprises a power supply 1113. A cathode of the power supply 1113 is connected to the photoelectron emission material 1110, while a positive pole thereof is connected to the stage 50. Therefore, a negative voltage is applied to the photoelectron emission material 1110 with respect to a voltage applied to the stage 50 and thus the wafer W.

Figure 46:
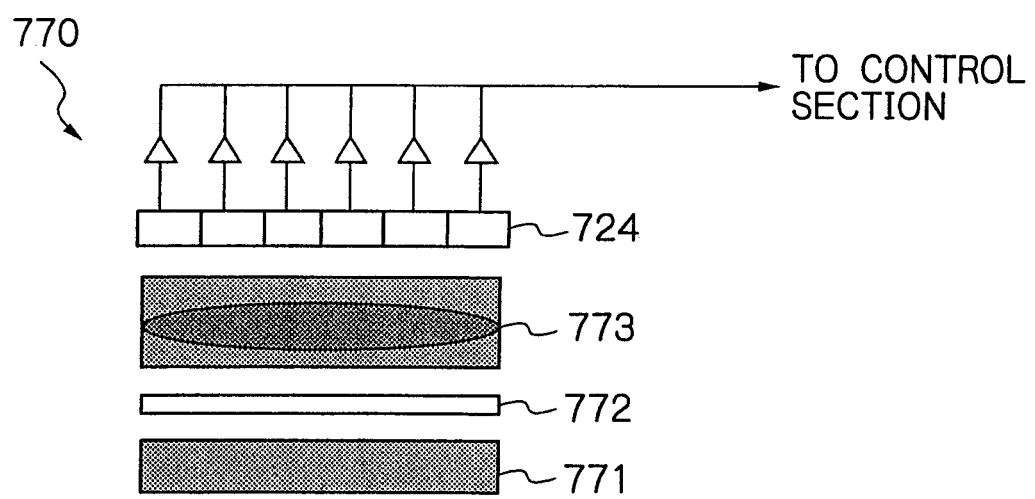
FIG. 46 is a schematic diagram illustrating an exemplary configuration of a detector in the defect inspection apparatus of FIG. 41.

The detector 770 may have any arbitrary configuration so far as it can convert the secondary electron image formed by the electrostatic lens 741 into a signal that can be treated in a subsequent process. For example, as shown in detail in FIG. 46, the detector 770 may comprise a multi-channel plate 771, a fluorescence screen 772, a relay lens system 773, and an imaging sensor 774 composed of multiple CCD elements. The multi-channel plate 771 includes a large number of channels in the plate and generates more electrons while the secondary electrons formed into an image by the electrostatic lens 741 are passing through said channels. That is, the multi-channel plate 771 increase the number of those secondary electrons. The fluorescence screen 772 converts the secondary electrons into light by emitting fluorescence with the amplified secondary electrons. The relay lens system 773 guides this fluorescence to the CCD imaging sensor 774, and then the CCD imaging sensor 774 converts an intensity distribution of the secondary electrons on the surface of the wafer W into an electric signal for each element, namely, digital image data, which is, in turn, output to the control section 1016.

The control section 1016 may be composed of a general purpose personal computer or the like, as shown in FIG. 24. This computer may comprise a control section main body 1014 for executing various controls and operations according to a predetermined program, a CRT 1015 for displaying a processed results from the main body 1014, and an input section 1018, such as a keyboard and a mouse, for an operator to input a command; and of course, the computer may have a control section 1016 that is composed of hardware or a workstation exclusively tailored for a defect inspection apparatus.

The control section main body 1014 comprises a CPU, a RAM, a ROM, a hard disk, and various control substrates including a video substrate (not shown). A secondary electron image storage region 1008 has been allocated memory such as the RAM or the hard disk, for storing the electric signal received from the detector 770, that is, the digital image data of the secondary electron image of the wafer W. Further, the hard disk contains, in addition to a control program for controlling the overall defect inspection apparatus, a defect detection program 1009 stored therein for reading out the secondary electron image data from the storage region 1008 and automatically detecting any defects in the wafer W based on said image data according to a specific algorithm. The defect detection program 1009 may have, for example, a function for comparing an inspection spot on the wafer W to another inspection spot on the same wafer 5 and giving the operator a warning by displaying as a defect a pattern different from those patterns at a majority of other inspection spots. Further, the secondary electron image 1017 may be displayed on the display section of the CRT 1015, so that the defect on the wafer W may be detected by the operator's visual observation.

An operation of the electron beam apparatus according to the embodiment according to the present invention of the present invention will now be described with reference to the flow chart shown in FIG. 27.

At first, the wafer 5, an object to be inspected, is set on the stage 50 (Step 1200). This may be conducted in such a manner whereby a plurality of wafers W contained in a loader (not shown), is set onto the stage 50 one-by-one. Then, the electron gun 721 emits a primary electron beam, which passes through the electrostatic lens 722 and is irradiated onto a specified inspection region on the set wafer W (Step 1202). The secondary electrons and/or reflected electrons (hereafter, referred to as "secondary electron") emanate from the wafer W having been irradiated with the primary electron beam, and resultantly the wafer W is charged up with positive potential. Then, those emanated secondary electrons are formed into an image on the detector 770 at a predetermined magnification through the electrostatic lens 741 of a magnified projection system (Step 1204). At that time, while a negative voltage is being applied to the photoelectron emission material 1110 by the stage 50, the UV lamp 1111 is turned on (Step 1206). As a result, an ultra-violet ray with a vibration frequency of ".nu." emitted from the UV lamp 1111 actuates the photoelectron emission material 1110 to emit a photoelectron therefrom according to its energy quantum "h.nu." (where, "h" is the Planck's constant). Those photoelectrons, "e.sup.-"s, are irradiated from the negatively charged photoelectron emission material 1110 toward the positively charged-up wafer W so as to electrically neutralize said wafer W. Thus, the secondary electron beam is allowed to form an image on the detector 770 without being substantially affected by the potential of the wafer W, which is otherwise possibly charged-up to be positive.

In this way, the detector 770 detects an image of the secondary electron beam that has emanated from the electrically neutralized wafer W with the reduced image disorders, and converts it into digital image data to output (Step 1208). Then, the control section 1016, according to the defect detection program 1009, executes a defect detection processing of the wafer W based on the detected image data (Step 1210). In this defect detection processing, the control section 1016 may extract any defective portions by comparing each detected images which has been detected for each of dies to one another, as described above, in the case of the wafer having a large number of equivalent dies. The control section 1016 may make a comparison to inspect any matching between a reference secondary electron beam image stored in the memory for a wafer having no defects and an actually detected secondary electron beam image, to enable automatic detection of the defective portion. At that time, the detected image may be displayed on the CRT 1015 with a mark indicating a portion that has been determined as a defective portion so that the operator can make a final inspection to determine whether or not the wafer W actually has a defect. A specific example of this defect inspection method will be described later in detail.

If the result of the defect inspection processing at Step 1210 indicates that a defect exists in the wafer W (Step 1212, affirmative determination), the operator is informed by a warning of the defect existing (Step 1218). As for the way of warning, for example, a message notifying the existence of the defect may be indicated on the display section of the CRT 1015, or additionally an enlarged image 1017 of the pattern in which the defect exists may be displayed thereon. Such a defective wafer may be immediately taken out of the sample chamber 32 so as to be stored in a different storage separate from the wafers with no defect (Step 1219).

If the result of the defect inspection processing at Step 1210 indicates that no defect exists in the wafer W (Step 1212, negative determination), it is determined whether or not there are still any remaining regions to be inspected (Step 1214). If some regions to be inspected still remain (Step 1214, affirmative determination), then the stage 50 is driven to move the wafer W so that the region to be further inspected may be positioned within the irradiative range of the primary electron beam (Step 1216). After that, the process goes back to Step 1202 to repeat the same procedure for the other regions.

If no more regions to be further inspected remain (Step 1214, negative determination), or the process of taking out the defective wafer (Step 1219) has been carried out, it is determined whether or not a wafer W, which is the current object to be inspected, is the last wafer, that is to say, whether or not any wafers remain in the loader (not shown) (Step 1220). If the current wafer is not the last one (Step 1220, negative determination), the wafer that has already been inspected is stored in a specified storage and a new wafer that has not been inspected yet is set instead on the stage 50 (Step 1222). After that, the process goes back to the Step 1202 to repeat the same procedures for that wafer. In contrast, if the current wafer is the last one to be inspected (Step 1220, affirmative determination), the wafer that has already been inspected is stored in the specified storage to complete the whole process.

The UV photoelectron irradiation (Step 1206) may be performed at any arbitrary timing and for any arbitrary period so far as it can help prevent positive charging in the wafer W and detecting the secondary electron image with the image disorders having been reduced (Step 1206). While the process of FIG. 27 is repeated, the UV lamp 1111 may be kept on, or otherwise the turning on and off of the UV lamp 1111 may be repeated periodically in a cycle specified for each wafer. In the latter case, an typical timing of the illumination, in addition to that shown in FIG. 27, may be before the secondary electron beam is formed into an image (Step 1204), or the illumination may begin before the primary electron beam is irradiated (Step 1202). Preferably, the UV photoelectron irradiation should be continued at least during the secondary electron detection, but the irradiation of the UV photoelectrons may be stopped even before or during the secondary electron detection so far as the wafer has been sufficiently neutralized.

Figure 28A:
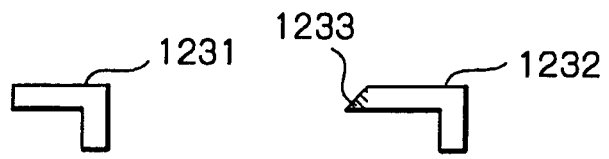
Figure 28B:
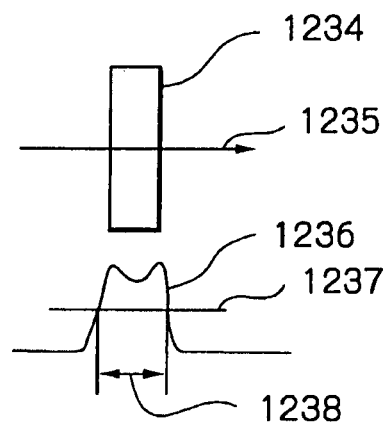
Figure 28C:
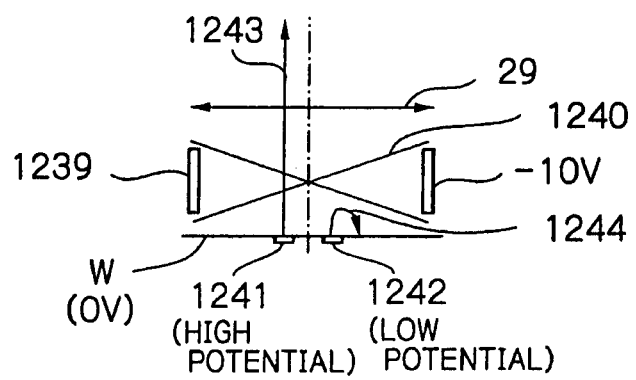

A specific example for the defect inspection method at Step 1210 is shown in FIGS. 28A to 28C. FIG. 28A shows an image 1231 for a die and an image 1232 for another die, which have been detected first and second respectively. If an image for another die, which has been detected third, is evaluated to be similar to the first image 1231, a portion 1233 of the second die image 1232 is determined to have a defect, and thus the defective portion can be detected.

FIG. 28B shows an example for measuring a line width of a pattern formed on a wafer. The reference numeral 1236 designates an intensity signal of an actual secondary electron in the scanning of an actual pattern 1234 along the direction 1235, and a width 1238 indicative of a portion where said signal continuously exceeds a threshold level 1237, which has been determined in advance by calibration, is measured as the line width of the pattern 1234. If any line width of the pattern measured in this way does not fall within a predetermined range, then that pattern may be determined to have a defect.

FIG. 28C shows an example for measuring a potential contrast of a pattern formed on a wafer. In the configuration shown in FIG. 24, an axially symmetrical electrode 1239 has been provided above the wafer W, and to the electrode 1239 has been applied, for example, a potential of −10V relative to a wafer potential of 0V. At that time, an equipotential surface is assumed to be drawn in the shape as indicated by 1240. It is to be assumed herein that patterns 1241 and 1242 are at the potentials of −4V and 0V respectively. In this case, since a second electron emanated from the pattern 1241 has an upward velocity equivalent to the kinetic energy of 2 eV in the −2V equipotential surface 40, the second electron overcomes that potential barrier 1240 and escapes from the electrode 1239 as indicated by an trajectory 1243, which would be detected by the detector 770. On the other hand, a second electron emanated from the pattern 1242 can not overcome the potential barrier of −2V and is driven back to the wafer surface as indicated by an orbit 1244, which would not be detected. Accordingly, a detected image for the pattern 1241 appears to be brighter, while the detected image for the pattern 1242 appears to be darker. Thus the potential contrast can be obtained. If the brightness and potential for a detected image has been calibrated in advance, a potential of a pattern can be measured from the detected image. Further, based on that potential distribution, the pattern can be evaluated on any defective portions.

Figure 25:
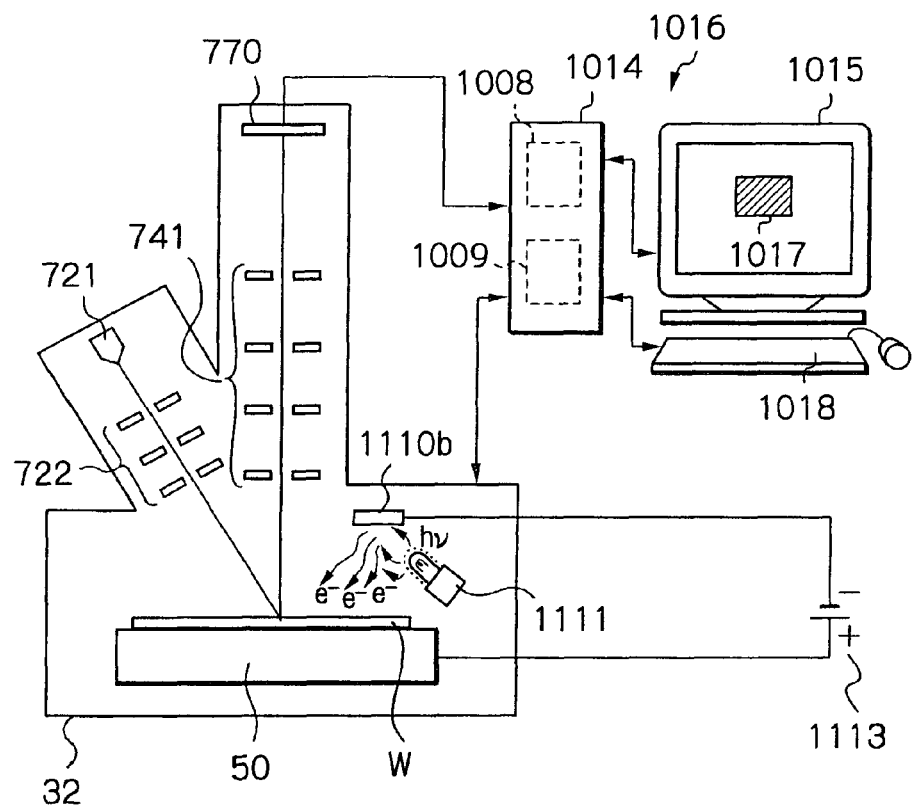
FIG. 25 is a schematic diagram of a defect inspection apparatus equipped with a precharge unit according to a further embodiment of the present invention.

FIG. 25 shows a general configuration of a defect inspection apparatus equipped with a pre-charge unit according to a further embodiment of the present invention. It should be noted that components similar to those in the embodiment of FIG. 24 are designated by the same reference numerals, and a detailed description thereof will be omitted.

In this embodiment, as shown in FIG. 25, a glass surface of an UV lamp 1111 is not coated with a photoelectron emission material. Instead, a photoelectron emission plate 1110*b* is disposed in a sample chamber 32 above a wafer W, and the UV lamp 1111 is located in such a position that the radiated ultra-violet ray is irradiated onto the photoelectron emission plate 1110*b*. The photoelectron emission plate 1110*b* is connected with a cathode, while a stage 50 is connected with a positive pole of a power supply 1113. The photoelectron emission plate 1110*b* may be made of metal such as Au or the like, or may be a plate coated with such metals.

An operation in the embodiment shown in FIG. 25 is similar to that in the embodiment shown in FIG. 24. Since the embodiment of FIG. 25 also allows the photoelectrons to be irradiated onto a surface of a wafer W, a similar effect to that in the embodiment of FIG. 24 may be obtained.

Figure 26:
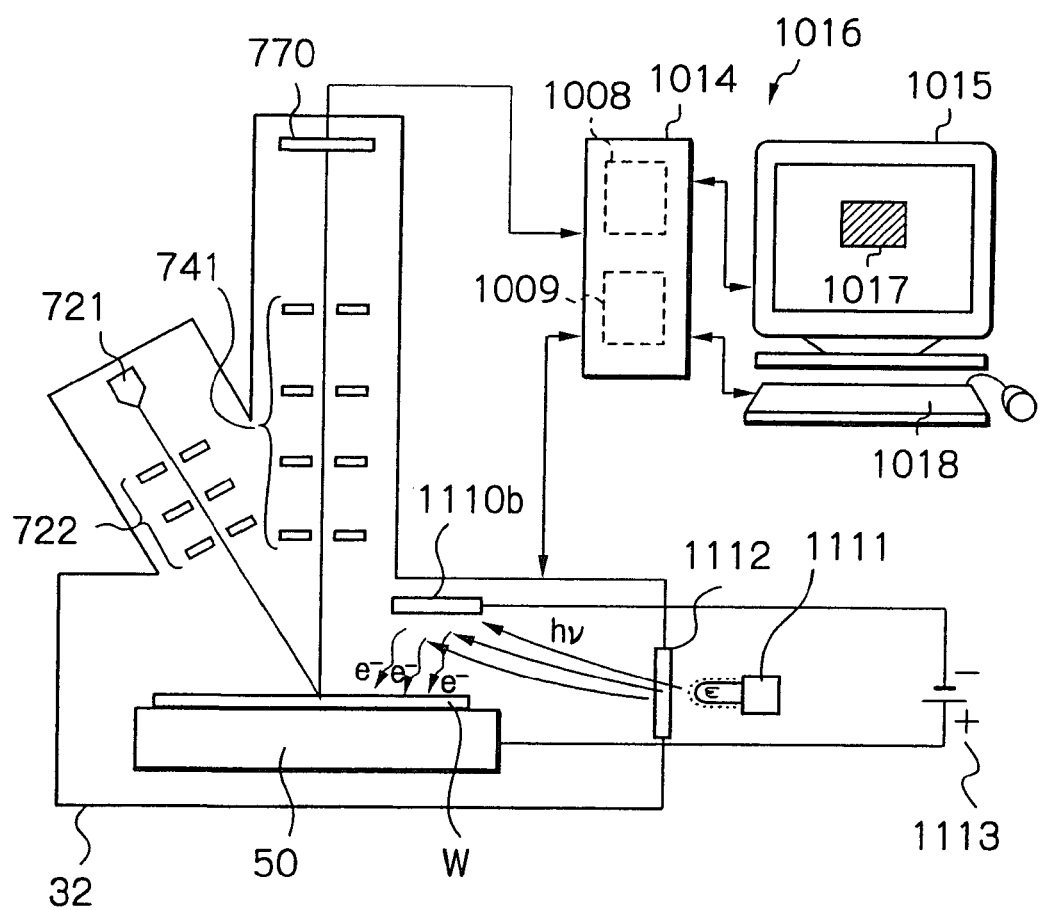
FIG. 26 is a schematic diagram of a defect inspection apparatus equipped with a precharge unit according to still further embodiment of the present invention.

FIG. 26 shows a general configuration of a defect inspection apparatus equipped with a pre-charge unit according to a still further embodiment of the present invention. It should be noted that components similar to those in the embodiments of FIGS. 24 and 25 are designated by the same reference numerals, and a detailed explanation on those components will be omitted.

In this embodiment, as shown in FIG. 26, a transparent window member 1112 is arranged in a side face wall of a sample chamber 32, and a UV lamp 1111 is located outside the sample chamber 32 so that the ultra-violet ray emitted from the UV lamp 1111 may pass through the window member 1112 and is irradiated onto a photoelectron emission plate 1110*b* disposed above a wafer W in the sample chamber 32.

In the embodiment shown in FIG. 26, since the UV lamp 1111 is located external to the sample chamber 32, which would be made vacuous, there is no more need to consider the resistivity of the UV lamp 1111 to the vacuum, thus giving more selections for the UV lamp 1111 than the first and the second embodiments.

Other operations in the embodiment of FIG. 26 are similar to those in the embodiments shown in FIGS. 24 and 25. Again, the embodiment of FIG. 26 allows the photoelectrons to be appropriately irradiated onto a surface of the wafer W, and a similar effect to those in the embodiment of FIG. 24 or 25 may be exhibited.

Although the present invention described above takes some preferred embodiments as examples, the defect inspection apparatus equipped with the pre-charge unit of the present invention is not limited to those embodiments described above, but may be arbitrarily and preferably modified within the scope of the subject matter of the present invention.

For example, although a wafer W has been selected as an example of a sample to be inspected, the sample to be inspected in the present invention is not limited to a wafer, and any object to which the electron beam is applicable in detecting a defect may be selected as the sample. For example, a mask, on which an exposing pattern for the wafer has been formed, or the like may be an object to be inspected.

Further, although typical configurations for the electron beam apparatus used in the defect inspection are illustrated in FIGS. 24 to 26, the electron optical system and others may be arbitrarily and preferably modified. For example, although the electron beam irradiation system (721, 722) of the defect inspection apparatus shown in FIGS. 24 to 26 employs a configuration in which the primary electron beam is irradiated to enter a surface of the wafer W from diagonally above, a deflection means for the primary electron beam may be arranged beneath the electrostatic lens 741 so that the primary electron beam enters the surface of the wafer W at right angles. As for such a separator, for example, a Wien filter may be used, which deflects the primary electron beam by an E.times.B field where an electric field and a magnetic field cross at right angles.

Further, it is apparent that any arbitrary means, other than the combination of the UV lamp 1111 with the photoelectron emission material 1110 or with the photoelectron emission plate 1110b shown in FIGS. 24 to 26, may be used as a means for emitting a photoelectron.

Figure 27:
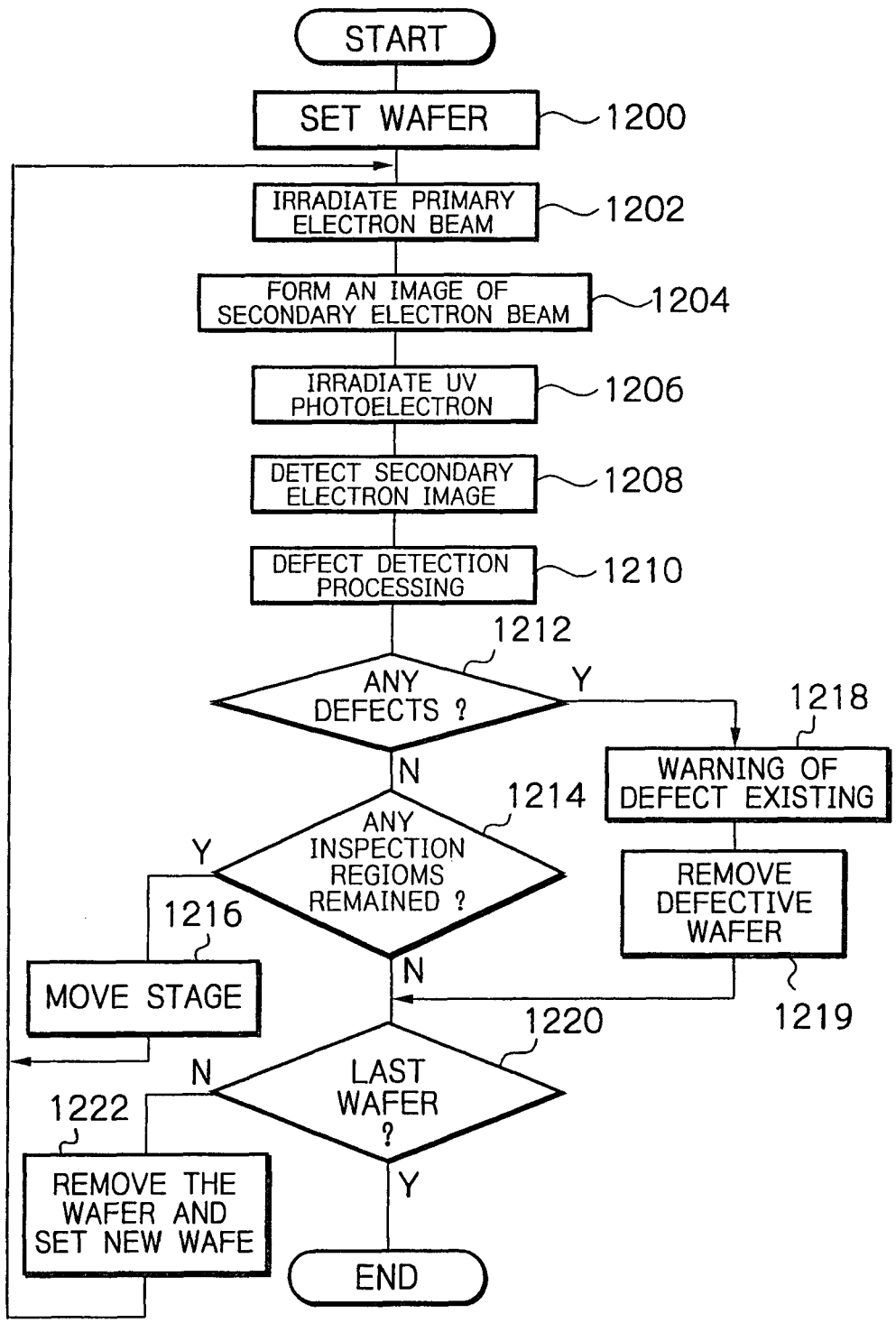
FIG. 27 is a flow chart showing a flow of a wafer inspection in the defect inspection apparatus according to any of the embodiments shown in FIGS. 24 to 26.

Still further, a process flow is not limited to that illustrated in FIG. 27. For example, although a sample in the above embodiment, which has already been determined to be defective at Step 1212, would not have been further inspected for other regions on the sample, the flow may be changed so that the defect may be detected through the inspection covering all regions. Further, if an irradiative region of the primary electron beam is extended so that one irradiation operation can cover all the inspection regions on a sample at once, Steps 1214 and 1216 may be omitted.

Further, although in FIG. 27, when a wafer has been determined to have a defect at Step 1212 and the warning has been immediately given to the operator to indicate the existence of the defect on the wafer at Step 1218 requesting that it be dealt with in the subsequent process (Step 1219), the flow may be changed so that a defect information may be recorded once and after a batch processing has been completed (i.e., after the affirmative determination at Step 1220), the defect information on a defective wafer may be reported.

As explained in detail above, according to the defect inspection apparatus and the defect inspecting method of the embodiments shown in FIGS. 24 to 26, since the electrons having energy lower than that of the primary electron beam are supplied to the sample to be inspected, positive charging in the surface of the sample possibly caused by the secondary electron emanation may be reduced, and thereby an image disorder of the secondary electron beam resulting from the charging may be also resolved, and eventually such an advantageous effect can be obtained that the sample may be inspected for a defect with high accuracy.

Further, according to the device manufacturing method which adopted the defect inspection apparatus of the embodiments shown in FIGS. 24 to 26, since the defect inspection is conducted by using such the defect inspection apparatus as described above, other significant effects may be obtained; that is, the yield of the product can be improved and the delivery of defective products can also be prevented.

Potential Applying Mechanism

Figure 29:
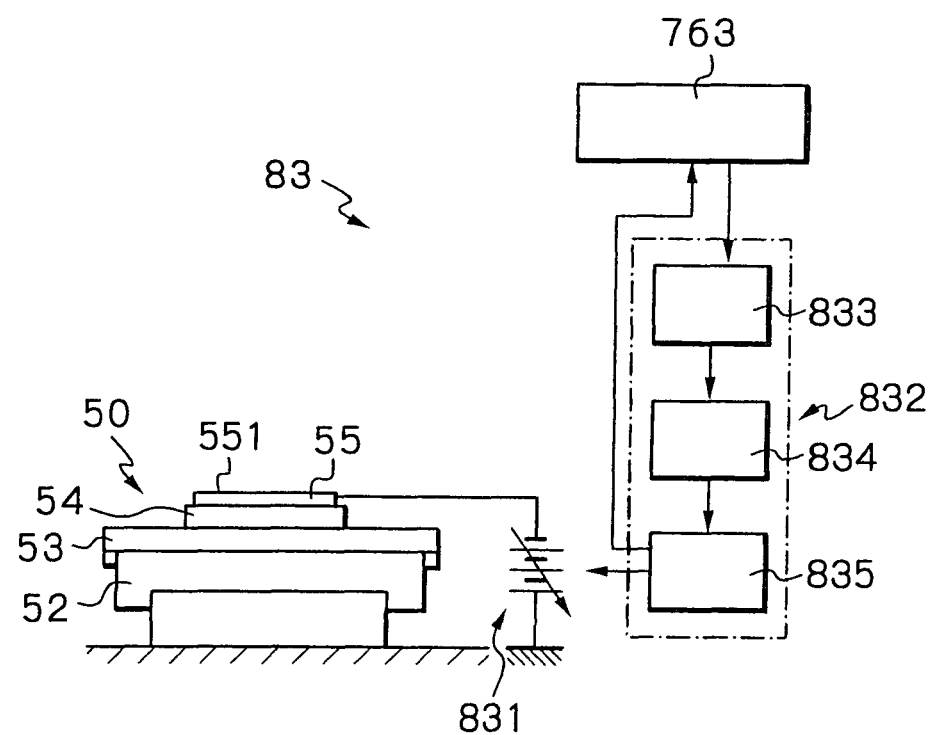
FIG. 29 is a diagram illustrating a potential applying mechanism.

Referring next to FIG. 29, the potential applying mechanism 83 applies a potential of .+-. several volts to a carrier of a stage, on which the wafer is placed, to control the generation of secondary electrons based on the fact that the secondary electron information or data emitted from the wafer (secondary electron generating rate) depend on the potential on the wafer. The potential applying mechanism 83 also serves to decelerate the energy originally possessed by irradiated electrons to provide the wafer with irradiated electron energy of approximately 100 to 500 eV.

As illustrated in FIG. 29, the potential applying mechanism 83 comprises a voltage applying device 831 electrically connected to the carrying surface 541 of the stage device 50; and a charging examining/voltage determining system (hereinafter referred to as examining/determining system) 832. The examining/determining system 832 comprises a monitor 833 electrically connected to an image forming unit 763 of the detecting system 76 in the electron-optical system 70; an operator 834 connected to the monitor 833; and a CPU 835 connected to the operator 834. The CPU 835 supplies a signal to the voltage applying device 831.

The potential applying mechanism 83 is designed to find a potential at which the wafer to be inspected is hardly charged, and to apply such potential to the carrying surface 541.

In a method for inspecting for an electrical defect on a sample to be inspected, the defect on the portion which is designed to be electrically insulated can be detected based on the fact that there is a voltage difference therein between the normal case where the portion is insulated and the defective case where the portion is in a conductive condition.

In this method, at first the electric charges are applied to the sample in advance, so that a voltage difference is generated between the voltage in the portion essentially insulated electrically and the voltage in another portion which is designed to be electrically insulated but is in a conductive condition due to the existence of any defects, then the beam of the present invention is applied thereto to obtain data about the voltage difference, which is then analyzed to detect the conductive condition.

Beam Calibration Mechanism

Figure 30:
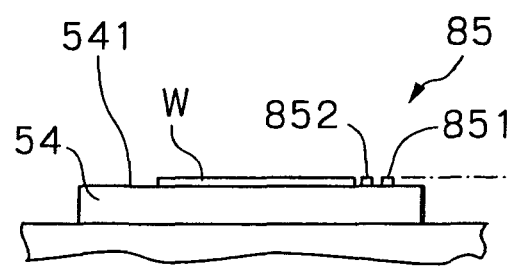
Figure 30:
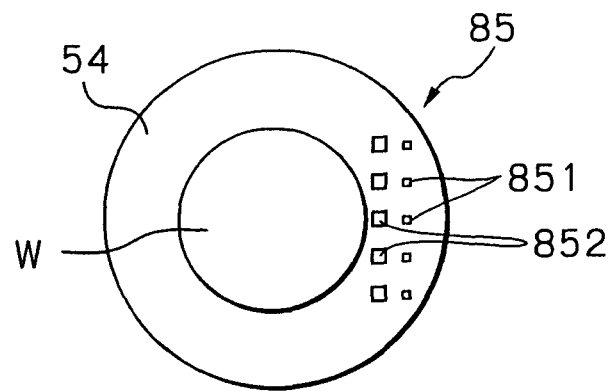

Referring next to FIG. 30, the electron beam calibration mechanism 85 comprises a plurality of Faraday cups 851, 852 for measuring a beam current, disposed at a plurality of positions in a lateral region of the wafer carrying surface 541 on the turntable 54. The Faraday cups 851 are provided for a narrow beam (approximately .phi.2 .mu.m), while the Faraday cuts 852 for a wide beam (approximately .phi.3 .mu..mu.m). The Faraday cups 851 are provided for a narrow beam measure a beam profile by driving the turntable 54 step by step, while the Faraday cups 852 for a wide beam measure a total amount of current. The Faraday cups 851, 852 are mounted on the wafer carrying surface 541 such that their top surfaces are coplanar with the upper surface of the wafer W carried on the carrying surface 541. In this way, the primary electron beam emitted from the electron gun 721 is monitored at all times. This is because the electron gun 721 cannot emit a constant electron beam at all times but varies in its emission intensity as it is used over a period of time.

Alignment Controller

The alignment controller 87 aligns the wafer W with the electron-optical device 70 using the stage device 50, and it performs the control for rough alignment through wide view field observation using the optical microscope 871 (a measurement with a lower magnification than the measurement made by the electron-optical system); high magnification alignment using the electron-optical system of the electron-optical system 70; focus adjustment; inspecting region setting; pattern alignment; and so on. The reason why the wafer is inspected at a low magnification using the optical microscope in this way is that an alignment mark must be readily detected by an electron beam when the wafer is aligned by observing patterns on the wafer in a small field using the electron beam for automatically inspecting patterns on the wafer.

Figure 31:
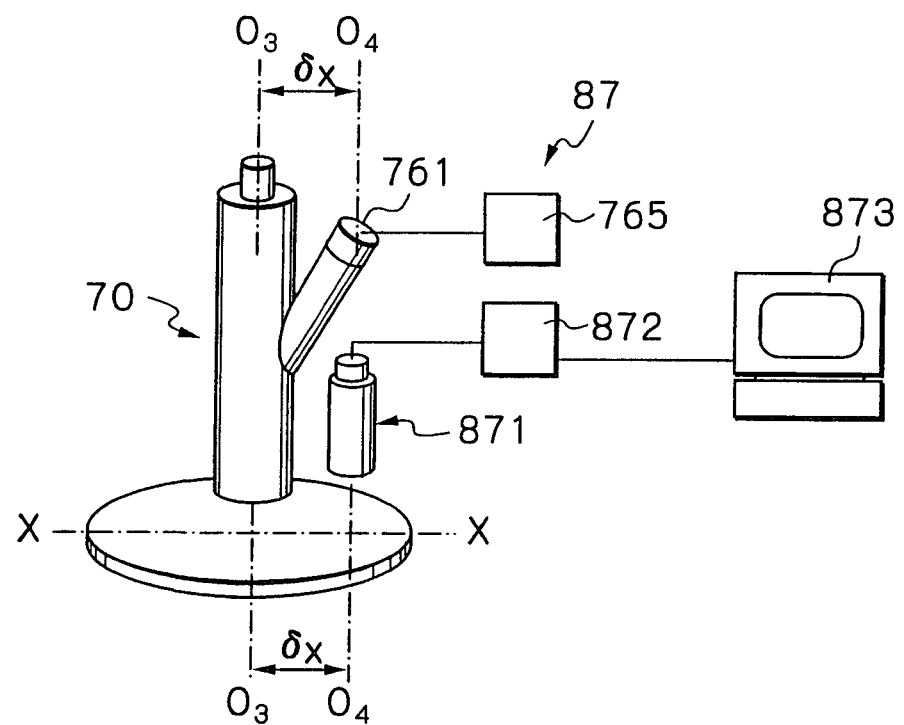
FIG. 31 is an explanatory diagram generally illustrating a wafer alignment controller.

The optical microscope 871 is disposed on the housing 30 (alternatively, it may be movably disposed within the housing 30), with a light source, not shown, being additionally disposed within the housing 30 for operating the optical microscope. The electron-optical system for observing the wafer at a high magnification shares the electron-optical systems (primary optical system 72 and secondary optical system 74) of the electron-optical device 70. The configuration may be generally illustrated in FIG. 31. For observing a point of interest on a wafer at a low magnification, the X-stage 53 of the stage device 50 is moved in the X-direction to move the point of interest on the wafer into a field of the optical microscope 871. The wafer is viewed in a wide field by the optical microscope 871, and the point of interest on the wafer to be observed is displayed on a monitor 873 through a CCD 872 to roughly determine a position to be observed. In this occurrence, the magnification of the optical microscope may be changed from a low to a high magnification.

Next, the stage system 50 is moved by a distance corresponding to a spacing .delta.x between the optical axis O3-O3 of the electron-optical system 70 and the optical axis O4-O4 of the optical microscope 871 to move the point on the wafer under observation, previously determined by the optical microscope 871, to a point in the field of the electron-optical system 70. In this occurrence, since the distance .delta.x between the axis $O_3$-$O_3$ of the electron-optical system and the axis $O_4$-$O_4$ of the optical microscope 871 is previously known (while it is assumed that the electron-optical system 70 is deviated from the optical microscope 871 in the direction along the X-axis in this embodiment, it may be deviated in the Y-axis direction as well as in the X-axis direction), the point under observation can be moved to the viewing position by moving the stage system 50 by the distance .delta.x. After the point under observation has been moved to the viewing position of the electron-optical system 70, the point under observation is imaged by the electron-optical system at a high magnification for storing a resulting image or displaying the image on the monitor 765 through the CCD 761.

After the point under observation on the wafer imaged by the electron-optical system at a high magnification is displayed on the monitor 765, misalignment of the wafer in its rotating direction with respect to the center of rotation of the turntable 54 of the stage system 50, and misalignment .delta..theta. of wafer in its rotating direction with respect to the optical axis $O_3$-$O_3$ of the electron-optical system are detected by a known method; misalignment of a predetermined pattern with respect to the electron-optical system in the X-axis and Y-axis is also detected. Then, the operation of the stage system 50 is controlled to align the wafer based on the detected values and data on an inspection mark attached on the wafer or data on the shape of the patterns on the wafer which have been obtained in separation.

Vacuum Exhausting System

A vacuum exhausting system is comprised of a vacuum pump, a vacuum valve, a vacuum gauge, a vacuum pipe and the like, and exhausts to vacuum an electron-optical system, a detector section, a sample chamber, a load-lock chamber and the like according to a predetermined sequence. In each of those sections, the vacuum valve is controlled so as to accomplish a required vacuum level. The vacuum level is regularly monitored, and in the case of irregularity, an interlock mechanism executes an emergency control of an isolation valve or the like to secure the vacuum level. As for the vacuum pump, a turbo molecular pump may be used for the main exhaust, and a dry pump of Roots type may be used as a roughing vacuum pump. A pressure at an inspection spot (an electron beam irradiating section) is practically in a range of $10^{-3}$ to $10^{-5}$ Pa, but more preferably, in a range of $10^{-4}$ to $10^{-6}$ Pa.

Control System

A control system is mainly comprised of a main controller, a controlling controller, and a stage controller.

The main controller is equipped with a man-machine interface, through which an operator manipulates the controller (a variety of instructions/commands, an entry of recipe, an instruction to start an inspection, a switching between an automatic inspection mode and a manual inspection mode, an input of all of the commands required in the manual inspection mode and so forth). In addition, the main controller may further execute communication with a host computer of a factory, a control of a vacuum exhausting system, a control of a carrying and a positioning operations of a sample such as a wafer, an operation for sending commands and receiving information to/from the other controllers and/or stage controller and so forth. Further, the main controller has the following functions: to obtain an image signal from an optical microscope; a stage vibration compensating function for compensating a deterioration in the image by feeding back a fluctuation signal of the stage to an electronic-optical system; and an automatic focal point compensating function for detecting a displacement of the sample observation point in the Z direction (in the axial direction of the secondary optical system) and feeding back the detected displacement to the electron-optical system so as to automatically compensate the focal point. Sending and receiving operations of the feedback signal to and from the electron-optical system and sending and receiving operations of the signal to and from the stage are performed via the controlling controller and the stage controller respectively.

The controlling controller is mainly responsible for the control of the electron-optical system (an electron gun, a lens, an aligner, a control of a high-precision power supply for a Wien filter or the like). Specifically, the controlling controller performs a control operation, for example, an automatic voltage setting for each of the lens systems and the aligners in response to each operation mode (gang control), so that a constant electron current may be regularly irradiated against the irradiation region even if the magnification is changed, and a voltage to be applied to each of the lens systems and the aligners may be automatically set in response to each magnification.

The stage controller is mainly responsible for a control regarding to the movement of the stage so that a precise movement in the X and the Y directions may be performed in the order of .mu.m (with tolerance of about .+-.0.5 .mu.m). Further, in the present stage, a control in the rotational direction (.theta. control) is also performed with a tolerance equal to or less than about .+-.0.3 seconds.

Cleaning of Electrode

In an electron beam apparatus according to the present invention being operated, a target substance floats due to a proximity interaction (charging of particles in the proximity of a surface) and is attracted to a high-voltage region; therefore, an organic substance will be deposited on a variety of electrodes used for forming or deflecting an electron beam. Since the insulating material gradually being deposited on the surface of the electrodes by the electric charge adversely affects the forming or deflecting mechanism for the electron beam, accordingly, this deposited insulating material must be periodically removed. To remove the insulating material periodically, an electrode adjacent to the region where the insulating material has been deposited is used to produce plasma of hydrogen, oxygen, fluorine, composition including these elements, HF, O.sub.2, H.sub.2O, C.sub.MF.sub.N or the like, to maintain the plasma potential in the space to the degree (several kV, e.g. 20-5 kV) so that sputtering is caused on the electrode surface, thereby allowing only the organic substance to be removed by oxidization, hydrogenation or fluorination.

Modified Embodiment of the Stage Device

Figure 32A:
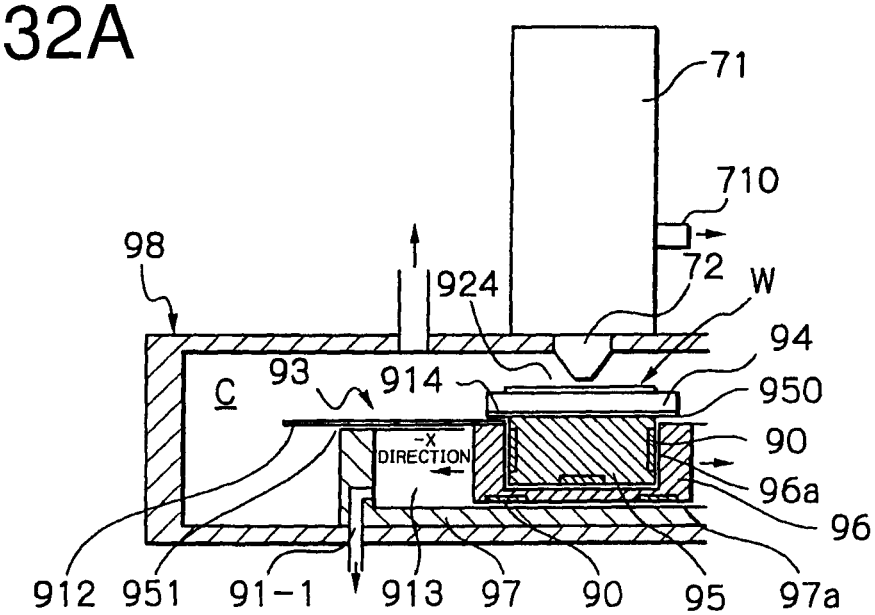
Figure 32B:
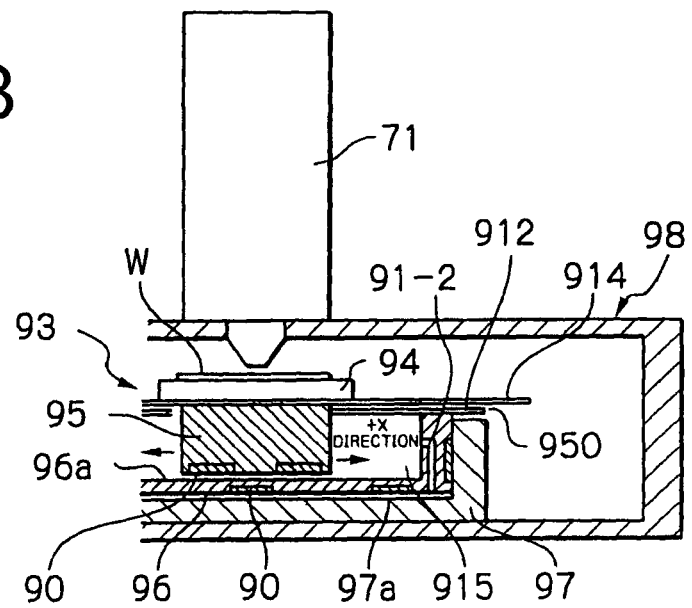

FIGS. 32A-32B show a modified embodiment of a vacuum chamber and XY stage adopted in the inspection apparatus according to the present invention.

A division plate 94 is attached onto an upper face of a Y directionally movable unit 95 of a stage 93, wherein said division plate 914 overhangs to a considerable degree, approximately horizontally in the +Y direction and the -Y direction (the lateral direction in FIG. 32B), so that between an upper face of an X directionally movable unit 96 and said division plate 914 there is always provided a narrow gap 950 with small conductance therebetween. Also, a similar division plate 912 is attached onto the upper face of the X directionally movable unit 96 so as to overhang in the .+-.X direction (the lateral direction in FIG. 32A), so that a narrow gap 951 may be constantly formed between an upper face of a stage table 97 and said division plate 912. The stage table 97 is fixedly secured onto a bottom wall within a housing 98 using a known method.

In this way, since the narrow gaps 950 and 951 are constantly formed wherever the sample table 94 may move, and the gaps 950 and 951 can prevent the movement of a desorbed gas even if a gas is desorbed or leaked along the guiding plane 96a or 97a upon movement of the movable unit 95 or 96, any increase in pressure can be considerably reduced in a space 924 adjacent to the sample against which the charged particles beam is irradiated.

Figure 56:
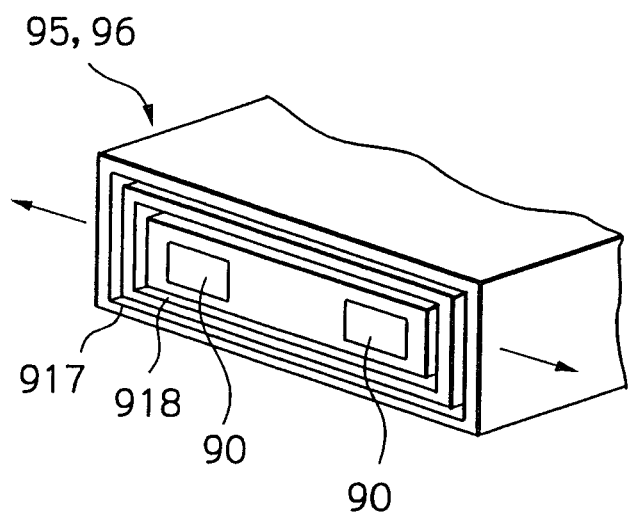
FIG. 56 is a diagram illustrating the relationship between hydrostatic bearings and a differential exhausting mechanism used for the XY stage of FIG. 55.

In a side-face and an under face of the movable unit 95 and also in an under face of the movable unit 96 of the stage 93, there are provided grooves, for differential exhausting formed surrounding hydrostatic bearings 90, as shown in FIG. 56, and which work for vacuum-exhausting; therefore, in a case where narrow gaps 950 and 951 have been formed, the desorbed gas from the guiding planes is mainly evacuated by these differential exhausting sections. Because of this, the pressures in spaces 913 and 915 within the stage are kept at higher levels than the pressure within chamber C. Accordingly, if there are more portions provided for vacuum-exhausting the spaces 913 and 915, in addition to the differential exhausting grooves 917 and 918, the pressure within the spaces 913 and 915 can be decreased, and the pressure rise of the space 924 in the vicinity of the sample can be controlled so as to be kept lower. For this purpose, vacuum exhausting channels 91-1 and 91-2 are provided. The vacuum exhausting channel 91-1 extends through the stage table 97 and the housing 98 to communicate with an outside of the housing 98. On the other hand, the exhausting channel 91-2 is formed in the X directionally movable unit 96 and opens in an under face thereof.

It is to be noted that though arranging the division plates 912 and 914 might cause a problem requiring the chamber C to be extended so that it does not interfere with the division plates, this can be improved by employing division plates of stretchable material or structure. One embodiment in this regard may be suggested, which employs the division plates made of rubber or in a form of bellows, the ends portions of which are fixedly secured respectively in the direction of movement so that each end of the division plate 914 is secured to the X directionally movable unit 96 and that of the division plate 912 to the inner wall of the housing 8.

Figure 33:
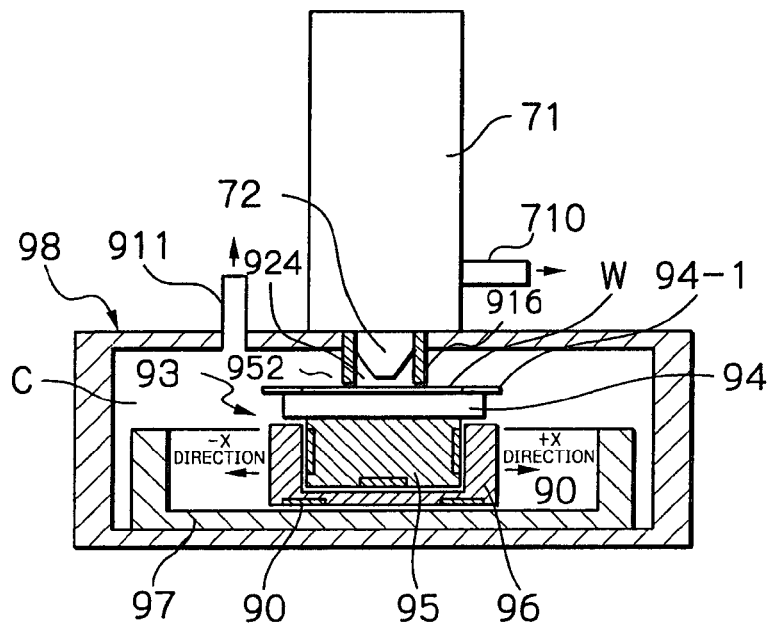
FIG. 33 is a sectional view of a vacuum chamber and an XY stage of a charged particles beam apparatus of another embodiment according to the present invention.

FIG. 33 shows a second modified embodiment of a vacuum chamber and XY stage according to the present invention.

In this embodiment, a cylindrical divider 916 is disposed surrounding the tip portion of the lens column or the charged particles beam irradiating section 72 so that a narrow gap may be produced between an upper face of a sample W and the tip portion of the lens column. In such configuration, even if the gas is desorbed from the XY stage, and increases the pressure within the chamber C, since a space 924 within the divider has been isolated by the divider 916 and exhausted with a vacuum pipe 710, there could be generated a pressure difference between the pressure in the chamber C and that in the space 924 within the divider, thus control the pressure rise in the space 924 within the divider 916 so that it is kept low. Preferably, the gap between the divider 916 and the sample surface should be approximately some ten .mu.m to some mm, depending on the pressure level to be maintained within the chamber C and in the surrounding of the irradiating section 72. It is to be understood that the interior of the divider 916 is made to communicate with the vacuum pipe by the known method.

On the other hand, the charged particles beam irradiation apparatus may sometimes apply a high voltage of kV to the sample W, and so it is feared that any conductive materials adjacent to the sample could cause an electric discharge. In this case, the divider 916 made of insulating material such as ceramic may be used in order to prevent any discharge between the sample W and the divider 916.

It is to be noted that a ring member 94-1 arranged so as to surround the sample W (a wafer) is a plate-like adjusting part fixedly mounted on the sample table 94 and set to have the same height as the wafer so that a micro gap 952 may be formed throughout a full circle of the tip portion of the divider 916 even when the charged particles beam is being irradiated against an edge portion of the sample such as the wafer. Thereby, whichever location on the sample W may be irradiated by the charged particles beam, the constant micro gap 952 can always be formed at the tip portion of the divider 916 so as to maintain a stable pressure in the space 924 surrounding the lens body tip portion.

Figure 34:
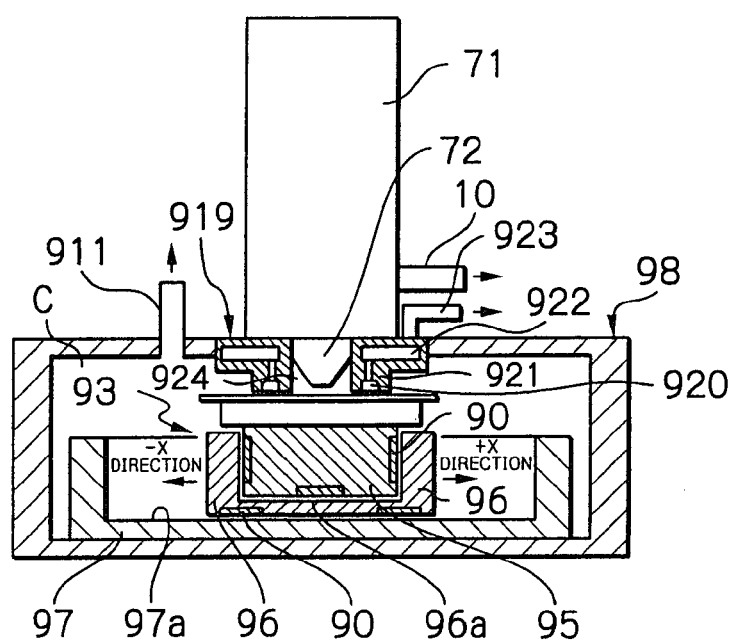
FIG. 34 is a sectional view of a vacuum chamber and an XY stage of a charged particles beam apparatus of an alternative embodiment according to the present invention.

FIG. 34 shows a further modified embodiment of a vacuum chamber and an XY stage according to the present invention.

A divider 919 having a differential exhausting structure integrated therein is arranged so as to surround the charged particles beam irradiating section 72 of a lens body 71. The divider 919 is cylindrical in shape and has a circular channel 920 formed inside thereof and an exhausting path 921 extending upwardly from said circular channel 920. Said exhausting path 921 is connected to a vacuum pipe 923 via an inner space 922. A micro space as narrow as some ten .mu.m to some mm is formed between the lower end of the divider 919 and the upper face of the sample W.

With such configuration, even if the gas is discharged from the stage in association with the movement of the stage resulting in an increase of the pressure within the chamber C, and eventually flows into the space of tip portion or the charged particles beam irradiating section 72, any flow of gas is blocked by the divider 919, which has reduced the gap between the sample W and itself so as to make the conductance very low, thus reducing the flow rate. Further, since any gas that has entered can be exhausted through the circular channel 920 to the vacuum pipe 923, there will be almost no gas remained to flow into the space 924 surrounding the charged particles beam irradiating section 72; accordingly, the pressure of the space surrounding the charged particles beam irradiating section 72 can be maintained at the desired high vacuum level.

Figure 35:
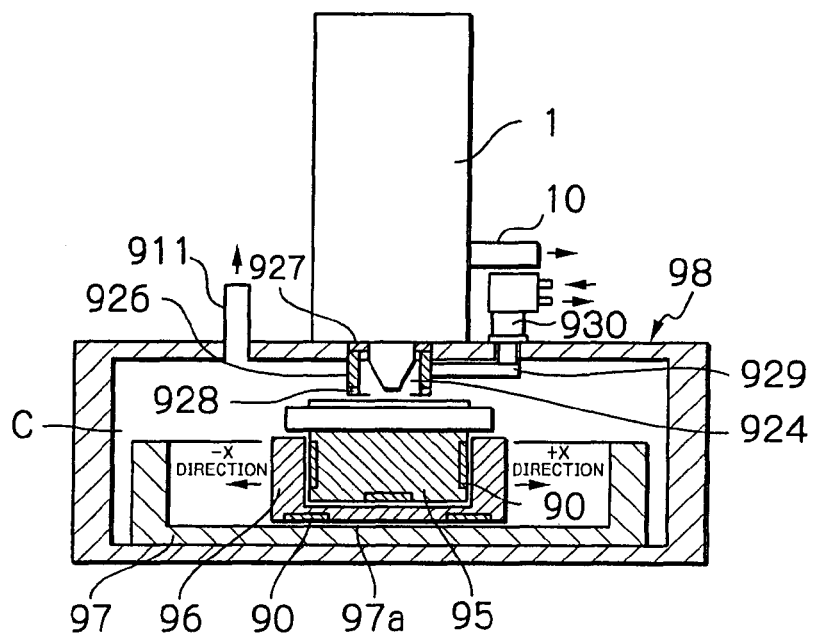
FIG. 35 is a sectional view of a vacuum chamber and an XY stage of a charged particles beam apparatus of further alternative embodiment according to the present invention.

FIG. 35 shows a still further modified embodiment of a vacuum chamber and an XY stage according to the present invention.

A divider 926 is arranged so as to surround the charged particles beam irradiating section 72 in the chamber C, thus isolating the charged particles beam irradiating section 72 from the chamber C. This divider 926 is coupled to a refrigerating machine 930 via a support member 929 made of material of high thermal conductivity such as copper or aluminum, and is kept as cool as −100.degree. C. to −200.degree. C. A member 927 is provided for blocking a thermal conduction between the cooled divider 926 and the lens barrel and is made of material of low thermal conductivity such as ceramic, resin or the like. Further, a member 928 is made of insulating material such as ceramic or the like and is attached to the lower end of the divider 926 so as to prevent any electric discharge between the sample W and the divider 926.

With such configuration, any gas molecules attempting to flow into the space surrounding the charged particles beam irradiating section from the chamber C are blocked by the divider 926, and even if some molecules manage to flow into the section, they are frozen to be captured on the surface of the divider 926, thus allowing the pressure in the space 924 surrounding the charged particles beam irradiating section to be kept low.

It is to be noted that various types of refrigerating machines may be used for the refrigerating machine in this embodiment, for example, a cooling machine using liquid nitrogen, a He refrigerating machine, a pulse-tube type refrigerating machine or the like.

Figure 36:
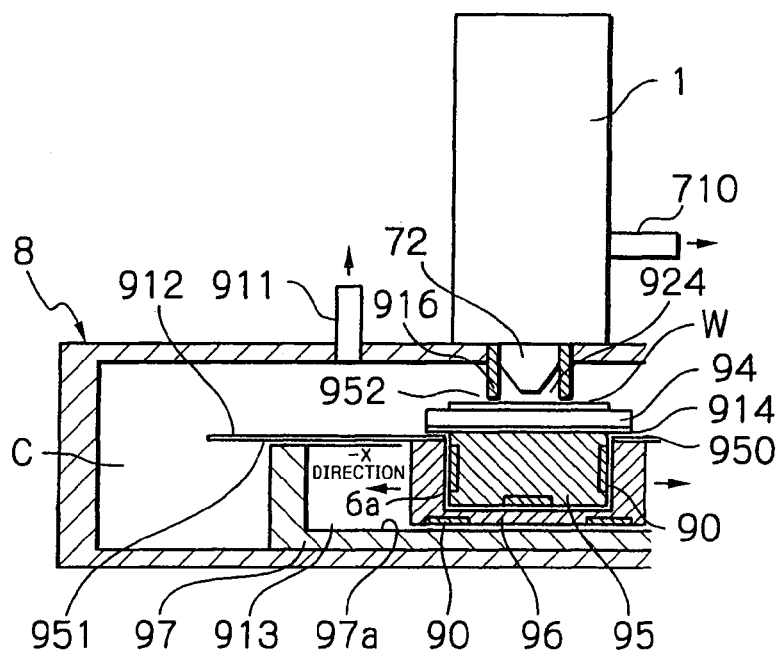
FIG. 36 is a sectional view of a vacuum chamber and an XY stage of a charged particles beam apparatus of a still further alternative embodiment according to the present invention.

FIG. 36 shows a further embodiment of a vacuum chamber and an XY stage according to the present invention.

The division plates 912 and 914 are arranged on both movable units of the stage 93 similarly to those illustrated in FIGS. 32A and 32B, and thereby, if the sample table 94 is moved to any location, the space 913 within the stage is separated from the inner space of the chamber C by those division plates through the narrow gaps 950 and 951. Further, another divider 916 similar to that as illustrated in FIG. 33 is formed surrounding the charged particles beam irradiating section 72 so as to separate a space 924 accommodating the charged particles beam irradiating section 72 therein from the interior of the chamber C with a narrow gap 952 disposed therebetween. Owing to this, upon movement of the stage, even if the gas adsorbed on the stage is desorbed into the space 913 to increase the pressure in this space, the pressure increase in the chamber C is controlled so that it is kept low, and the pressure increase in the space 924 is also kept even lower. This allows the pressure in the space 924 for irradiating the charged particles beam to be maintained at a low level. Alternatively, employing the divider 919 having the differential exhausting mechanism integrated therein as explained with reference to FIG. 34, or the divider 926 cooled with the refrigerating machine as shown in FIG. 34 allows the space 924 to be maintained stably with further lowered pressure.

According to the subject embodiment, the following effects may be expected to obtain.

(a) The stage device can enhance accurate positioning within a vacuum atmosphere and the pressure in the space surrounding the charged particles beam irradiating location is hardly increased. That is, it allows the charged particles beam processing to be applied to the sample with high accuracy.

(b) It is almost impossible for the gas desorbed or leaked from the hydrostatic bearing to go though the divider and reach the space for the charged particles beam irradiating system. Thereby, the vacuum level in the space surrounding the charged particles beam irradiating location can be further stabilized.

(c) It is harder for the desorbed gas to go through to the space for the charged particles beam irradiating system, and it is easier to maintain the stability of the vacuum level in the space surrounding the charged particles beam irradiating location.

(d) The interior of the vacuum chamber is partitioned into three chambers, i.e., a charged particles beam irradiation chamber, a hydrostatic bearing chamber and an intermediate chamber; each can communicate with the other via a small conductance. Further, the vacuum exhausting system is constructed so that the pressures in the respective chambers are controlled sequentially, so that the pressure in the charged particles beam irradiation chamber is the lowest, that in the intermediate chamber is in the middle range, and that in the hydrostatic bearing chamber is the highest. The pressure fluctuation in the intermediate chamber can be reduced by the divider, and the pressure fluctuation in the charged particles beam irradiation chamber can be further reduced by another step of divider, so that the pressure fluctuation therein can be reduced substantially to a non-problematic level.

(e) The pressure increase upon movement of the stage can be controlled so that it is kept low.

(f) The pressure increase upon movement of the stage can be further controlled so that it is kept even lower (g) Since a defect inspection apparatus with highly accurate stage positioning performance and with a stable vacuum level in the charged particles beam irradiating region can be accomplished, an inspection apparatus with high inspection performance and without any fear of contamination of the sample can be provided.

(h) Since a defect inspection apparatus with highly accurate stage positioning performance and with a stable vacuum level in the charged particles beam irradiating region can be accomplished, an exposing apparatus with high exposing accuracy and without any fear of contamination of the sample can be provided.

(i) Manufacturing the semiconductor by using the apparatus with highly accurate stage positioning performance and with a stable vacuum level in the charged particles beam irradiating region allows a miniaturized micro semiconductor circuit to be formed.

Incidentally, it is apparent that the stage device shown in FIGS. 32A-36 can be applied to the stage device 50 shown in FIG. 1.

Figure 55A:
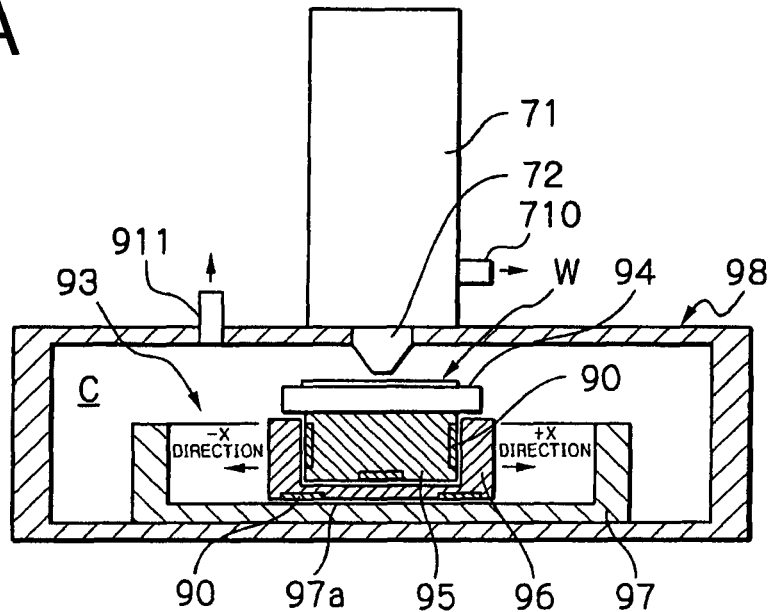
Figure 55B:
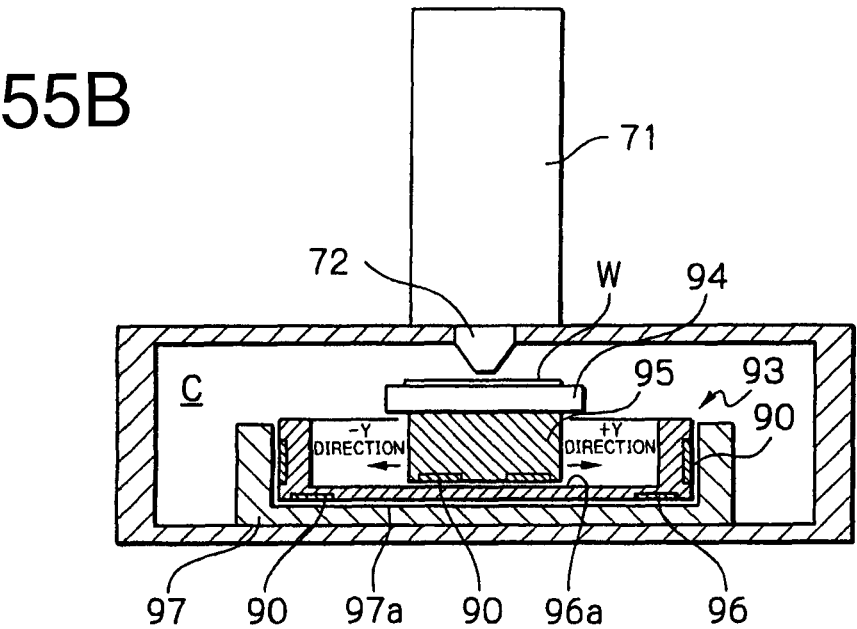

Further embodiments of the XY stage according to the present invention will now be described with reference to FIGS. 37 to 39. It is to be noted that the same reference numerals are used to designate the same components common to both the embodiment according to the prior art shown in FIGS. 55A-55B and the embodiments according to the present invention. It is also to be appreciated that a term "vacuum" used in this specification means a vacuum as referred to in the field pertaining to this art and does not necessarily refer to an absolute vacuum.

Figure 37:
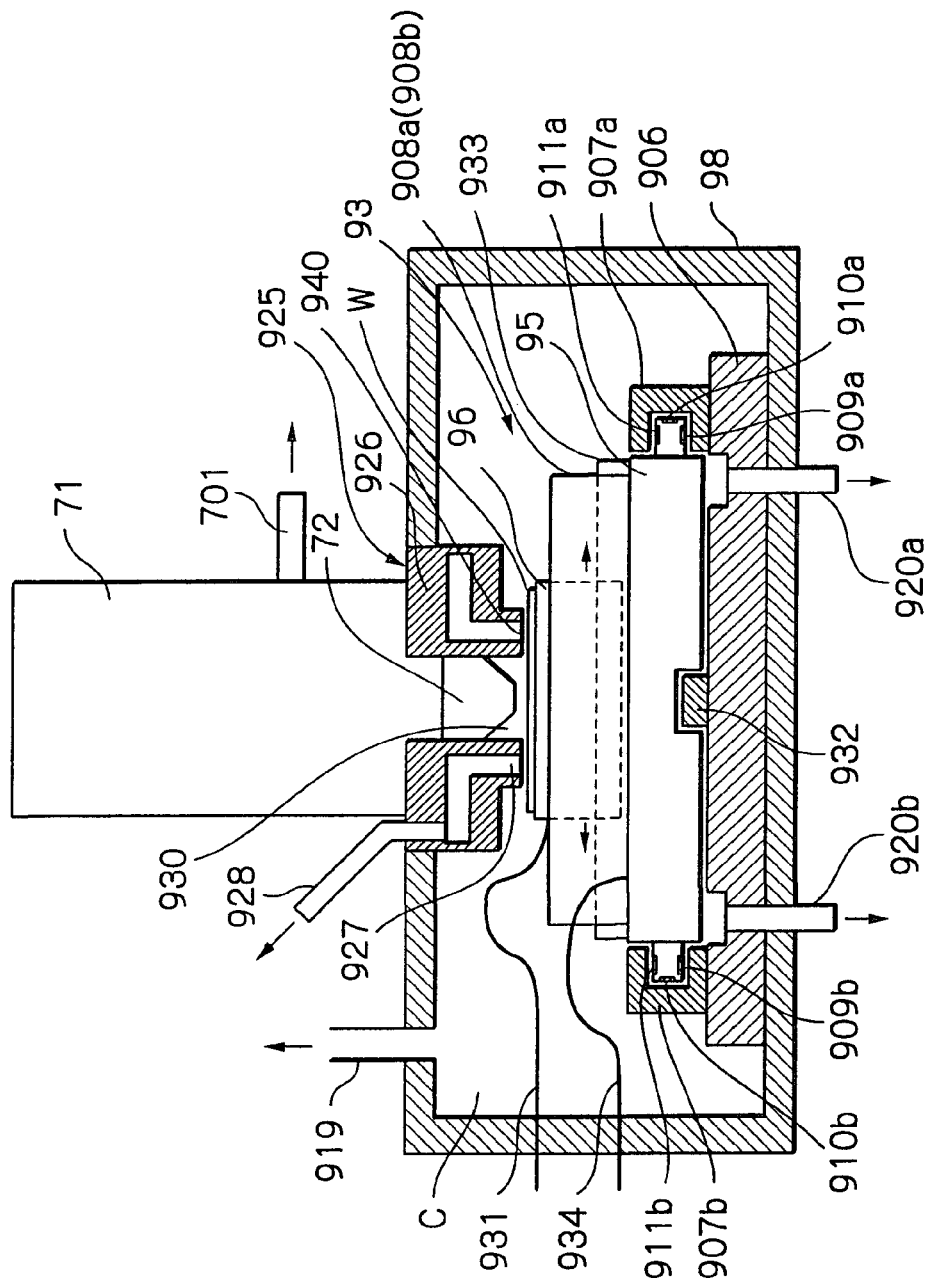
FIG. 37 is a schematic cross sectional view illustrating a vacuum chamber and an XY stage of a charged particles beam apparatus according to an embodiment of the present invention.

FIG. 37 shows another embodiment of the XY stage.

A tip portion of a lens body 71 or a charged particles beam irradiating section 72, which functions to irradiate a charged particles beam against a sample, is mounted on a housing 98 defining a vacuum chamber C. The sample "W" loaded on a table of an XY stage 93 movable in the X direction (the lateral direction in FIG. 3) is adapted to be positioned immediately under the lens body 71. The XY stage 93 of high precision allows the charged particles beam to be irradiated onto this sample W accurately in any arbitrary location of the sample surface.

A pedestal 906 of the XY stage 93 is fixedly mounted on a bottom wall of the housing 98, and a Y table 95 movable in the Y direction (the vertical direction on paper in FIG. 37) is loaded on the pedestal 906. Convex portions are formed on both opposite sidewall faces (the left and the right side faces in FIG. 37) of the Y table 95 respectively, each of which projects into a concave groove formed on a side surface facing the Y table in either of a pair of Y-directional guides 907a and 907b mounted on the pedestal 906. The concave groove extends along approximately the full length of the Y directional guide in the Y direction. A top, a bottom and a side face of respective convex portions protruding into the grooves are provided with known hydrostatic bearings 911a, 909a, 911b and 909b respectively, through which a high-pressure gas is expelled and thereby the Y table 95 is supported to the Y directional guides 907a and 907b in non-contact manner so as to be movable smoothly reciprocating in the Y direction. Further, a linear motor 932 of known structure is arranged between the pedestal 906 and the Y table 95 for driving the Y table 95 in the Y direction. The Y table 95 is supplied with the high-pressure gas through a flexible pipe 934 for supplying a high-pressure gas, and the high-pressure gas is further supplied to the above-described hydrostatic bearings 909a to 911a and 909b to 911b though a gas passage (not shown) formed within the Y table. The high-pressure gas supplied to the hydrostatic bearings is expelled into a gap of from several microns to some ten microns in thickness formed respectively between the bearings and the opposing guide planes of the Y directional guide so as to position the Y table accurately with respect to the guide planes in the X and Z directions (up and down directions in FIG. 37).

The X table 96 is loaded on the Y table so as to be movable in the X direction (the lateral direction in FIG. 37). A pair of X directional guides 908a and 908b (only 908a is illustrated) with the same configuration as of the Y directional guides 907a and 907b is arranged on the Y table 95 with the X table 96 sandwiched therebetween. Concave grooves are also formed in the X directional guides on the sides facing the X table and convex portions are formed on the side portions of the X table (side portions facing the X directional guides). The concave groove extends approximately along the full length of the X directional guide. A top, a bottom and a side face of respective convex portions of the X table protruding into the concave grooves are provided with hydrostatic bearings (not shown) similar to those hydrostatic bearings 911a, 909a, 910a, 911b, 909b and 910b in the similar arrangements. A linear motor 933 of known configuration is disposed between the Y table 95 and the X table 96 so as to drive the X table in the X direction. Further, the X table 96 is supplied with a high-pressure gas through a flexible pipe 931, and thus the high-pressure gas is supplied to the hydrostatic bearings. The X table 96 is supported highly precisely with respect to the Y directional guide in a non-contact manner by way of said high-pressure gas blowing out from the hydrostatic bearings to the guide planes of the X-directional guides. The vacuum chamber C is exhausted through vacuum pipes 919, 920a and 920b coupled to a vacuum pump of a known structure. Those pipes 920a and 920b penetrate the pedestal 906 at the top surface thereof to open their inlet sides (inner side of the vacuum chamber) in the proximity of the locations to which the high-pressure gas is ejected from the XY stage 93, so that the pressure in the vacuum chamber may be prevented to the utmost from rising up by the gas expelled from the hydrostatic bearings.

A differential exhausting mechanism 925 is arranged so as to surround the tip portion of the lens body 71 or the charged particles beam irradiating section 72, so that the pressure in a charged particles beam irradiation space 930 can be controlled so that it is sufficiently low even if there exists high pressure in the vacuum chamber C. That is to say, an annular member 926 of the differential exhausting mechanism 925, mounted so as to surround the charged particles beam irradiating section 72, is positioned with respect to the housing 98 so that a micro gap (of a thickness ranging from several microns to several hundred microns) 940 can be formed between the lower face thereof (the surface facing to the sample) and the sample, and an annular groove 927 is formed in the lower face thereof. That annular groove 927 is coupled to a vacuum pump or the like (not shown), through an exhausting pipe 928. Accordingly, the micro gap 940 can be exhausted through the annular groove 927 and the exhausting pipe 928, and if any gaseous molecules from the chamber C attempt to enter the space 930 circumscribed by the annular member 926, they can be exhausted. Thereby, the pressure within the charged particles beam irradiation space 930 can be kept low and thus the charged particles beam can be irradiated without any problems.

The size of said annular groove may be doubled or tripled, depending on the pressure in the chamber C and the pressure within the charged particles beam irradiation space 930.

Typically, dry nitrogen is used as the high-pressure gas to be supplied to the hydrostatic bearings. If available, however, a much higher-purity inert gas should preferably be used instead. This is because any impurities such as water, oil or fat included in the gas could stick on the inner surface of the housing defining the vacuum chamber or on the surfaces of the stage components leading to the deterioration in vacuum level, or could stick on the sample surface leading to the deterioration in vacuum level in the charged particles beam irradiation space.

It should be appreciated that although typically the sample W is not placed directly on the X table but may be placed on a sample table having a function to detachably carry the sample and/or a function to make a fine tuning of the position of the sample relative to the XY stage 93, an explanation therefor is omitted in the above description for simplicity due to the reason that the presence and structure of the sample table has no concern with the principal concept of the present embodiment.

Since a stage mechanism of a hydrostatic bearing used in the atmospheric pressure can be used in the above-described charged particles beam apparatus mostly as it is, a stage having an equivalent level of precision with equivalent cost and size to those of the stage of high-precision fitted for a use in the atmospheric pressure, which is typically used in an exposing apparatus or the likes, may be accomplished for an XY stage to be used in a charged particles beam apparatus.

It should be also appreciated that the configuration and arrangement of the hydrostatic guide and the actuator (the linear motor) have been only illustratively explained in the above description, and any hydrostatic guides and actuators usable in the atmospheric pressure may be applicable.

Figure 38:
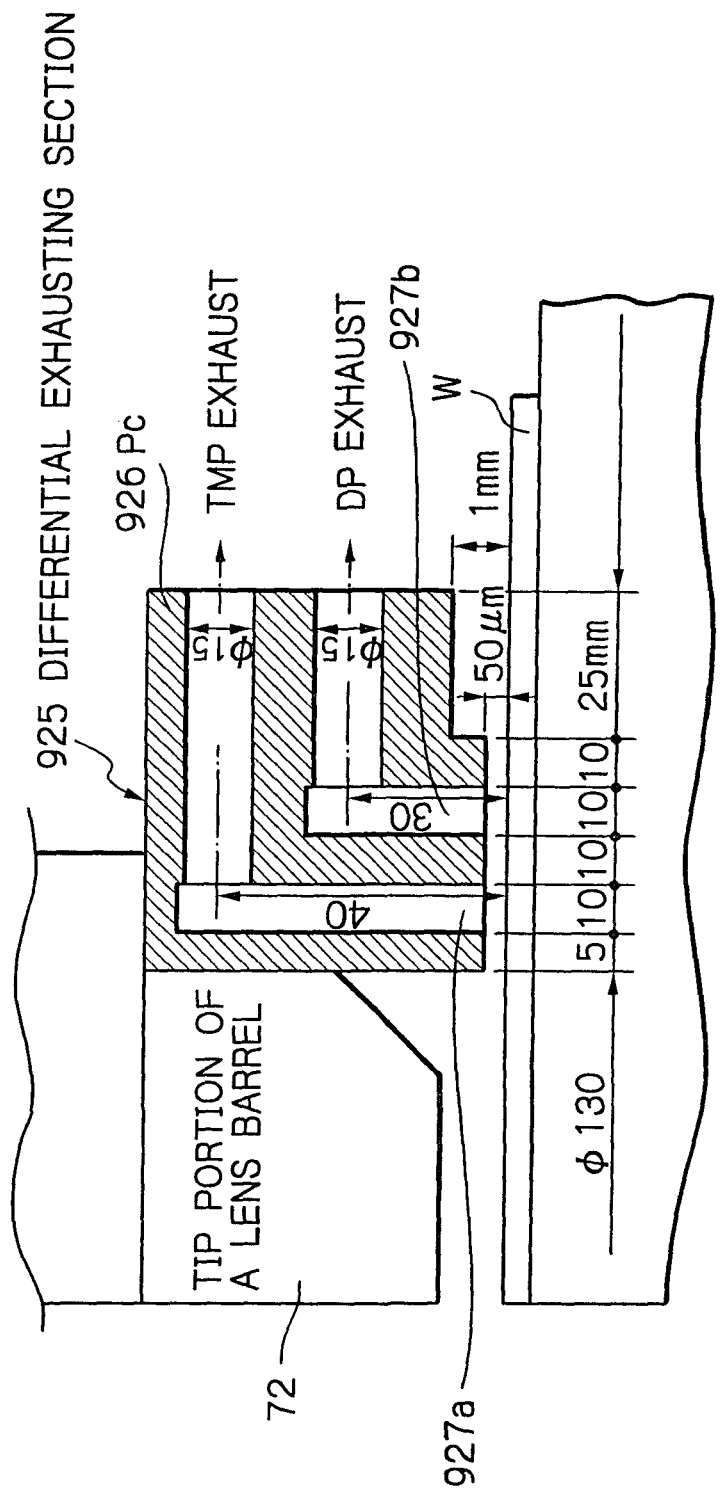
FIG. 38 is a schematic diagram illustrating an example of a differential exhausting mechanism provided in the apparatus shown in FIG. 37.

FIG. 38 shows an example of numerical values representative of the sizes of the annular member 926 and the annular groove formed in the annular member 926 of the differential exhausting mechanism. It is to be noted that in this example, the size of the annular groove is twice that of the structure of 927a and 927b, which are separated from each other in the radial direction.

The flow rate of the high-pressure gas supplied to the hydrostatic bearing is in the order of about 20 L/min (in the conversion into the atmospheric pressure). Assuming that the vacuum chamber C is exhausted by a dry pump having an exhaust velocity of 20000 L/min via a vacuum pipe having an inner diameter of 50 mm and a length of 2 m, the pressure in the vacuum chamber C will be about 160 Pa (about 1.2 Torr). At that time, with the applied size of the annular member 926, the annular groove and others of the differential exhausting mechanism as described in FIG. 38, the pressure within the charged particles beam irradiation space 930 can be controlled to $10^{-4}$ Pa ($10^{-6}$ Torr).

Figure 39:
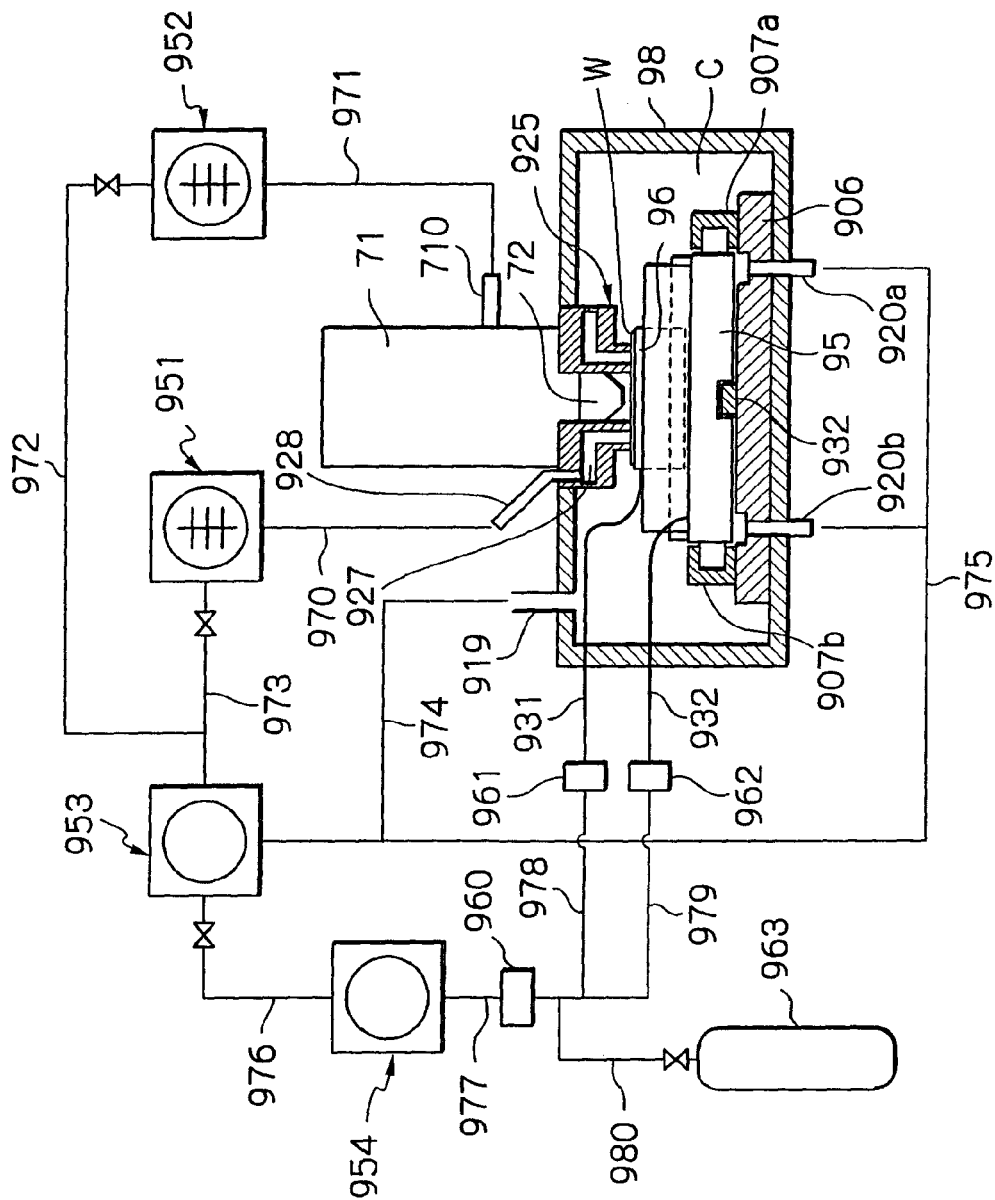
FIG. 39 is a schematic diagram illustrating a circulating pipe line of a gas in the apparatus shown in FIG. 37.

FIG. 39 shows a further embodiment of the XY stage. A vacuum chamber C defined by a housing 98 is connected with a dry vacuum pump 953 via vacuum pipes 974 and 976. An annular groove 927 of a differential exhausting mechanism 925 is connected with an ultra-high vacuum pump or a turbo molecular pump 951 via a vacuum pipe 970 connected to an exhaust port 928. Further, the interior of a lens body 71 is connected with a turbo molecular pump 952 via a vacuum pipe 971 connected to an exhaust port 710. Those turbo molecular pumps 951 and 952 are connected to the dry vacuum pump 953 through vacuum pipes 972 and 973. (In FIG. 39, the single dry vacuum pump is used to serve both as a roughing vacuum pump of the turbo molecular pump and as a pump for vacuum exhausting of the chamber, but multiple dry vacuum pumps of separate systems may be employed for exhausting, depending on the flow rate of the high-pressure gas supplied to the hydrostatic bearings of the XY stage, the volume and inner surface area of the vacuum chamber and the inner diameter and length of the vacuum pipes.)

A high-purity inert gas ($N_2$ gas, Ar gas or the like) is supplied to a hydrostatic bearing of an XY stage 93 through flexible pipes 931 and 932. The gaseous molecules expelled from the hydrostatic bearing are diffused into the vacuum chamber and exhausted by the dry vacuum pump 953 through exhaust ports 919, 920a and 920b. Further, the gaseous molecules that have entered the differential exhausting mechanism and/or the charged particles beam irradiation space are sucked from the annular groove 927 or the tip portion of the lens body 72 through the exhausting ports 928 and 710 to be exhausted by the turbo molecular pumps 951 and 952; then, after having been exhausted by the turbo molecular pumps, the gaseous molecules are further exhausted by the dry vacuum pump 953.

In this way, the high-purity inert gas supplied to the hydrostatic bearing is collected in the dry vacuum pump and then exhausted.

On the other hand, the exhaust port of the dry vacuum pump 953 is connected to a compressor 954 via a pipe 976, and the exhaust port of the compressor 954 is connected to flexible pipes 931 and 932 via pipes 977, 978 and 979 and regulators 961 and 962. As a result of this configuration, the high-purity inert gas exhausted from the dry vacuum pump 953 is compressed again by the compressor 954 and then the gas, after being regulated to an appropriate pressure by the regulators 961 and 962, is supplied again to the hydrostatic bearings of the XY stage.

In this regard, since the gas to be supplied to the hydrostatic bearings is required to be as highly purified as possible in order not to have any water contents or oil and fat contents included therein, as described above, the turbo molecular pump, the dry pump and the compressor must have structures that prevent any water contents or oil and fat contents from entering the gas flow path. It is also considered effective for a cold trap, filter or the like (960) to be provided along the outlet side piping 977 of the compressor so as to trap any impurities such as water, oil or fat contents included in the circulating gas and prevent them from being supplied to the hydrostatic bearings.

This may allow the high purity inert gas to be circulated and reused, and thus allows the high-purity inert gas to be saved, while the inert gas would not remain desorbed into a room where the present apparatus is installed, thereby eliminating a fear that any accidents such as suffocation or the like would be caused by the inert gas.

It is to be noted that a circulation piping system is connected with the high-purity inert gas supply system 963, said system 963 serving not only to fill up, with the high-purity inert gas, all of the circulation systems including the vacuum chamber C, the vacuum pipes 970 to 975, and the pipes in compression side 976 to 980, prior to the commencement of the gas circulation, but also to supply gas if the flow rate of the circulation gas decreases for some reason.

Further, a single dry vacuum pump 953, if provided with a function to compress to a level equal to or greater than the atmospheric pressure, may be used as both the dry vacuum pump 953 and the compressor 954.

Further, as to the ultra-high vacuum pump to be used for exhausting the lens body, other pumps including an ion pump and a getter pump may be used instead of the turbo molecular pump. It is to be noted that in the case where reservoir type pumps are used, it is prohibited to build circulation systems in those areas. It is also evident that instead of the dry vacuum pump, other type of dry pumps, for example, a dry pump of diaphragm type, may be used.

Figure 40:
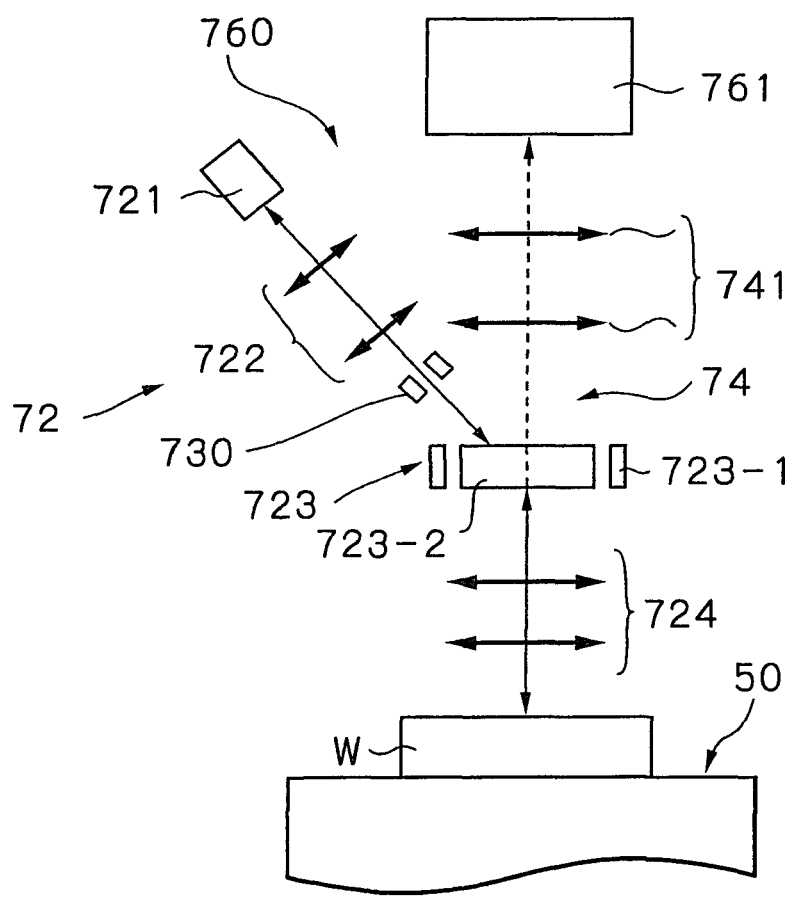
FIG. 40 is a schematic diagram illustrating an example of an optical system and a detecting system to be provided in an optical column.

FIG. 40 schematically shows a typical optical system and a detector of a charged particles beam apparatus of an embodiment according to the present invention. Though the optical system is provided in the lens body 71, these optical system and detector are illustrated only as an example, but the other optical systems and detectors may be employed if required. An optical system 760 of the charged particles beam apparatus comprises a primary optical system 72 for irradiating a charged particles beam against a sample W loaded on a stage 50 and a secondary optical system 74 into which secondary electrons emanated from the sample are to be introduced. The primary optical system 72 comprises an electron gun 721 for emitting the electron, a lens systems composed of two stages of electrostatic lenses 722 for converging the electron emitted from the electron gun 721, a deflector 730, a Wien filter or an E.times.B separator 723 for deflecting the charged particles beam so as for an optical axis thereof to be directed to perpendicular to a surface of an object, and a lens system composed of two stages of electrostatic lenses 724, wherein those components of the primary optical system 72 are arranged in the order with the electron gun 721 at the topmost location so that the optical axis of the charged particles beam is inclined to the line normal to a surface of the sample W (a sample surface) as shown in FIG. 40. The E.times.B deflecting system 723 comprises an electrode 723-1 and a magnet 723-2.

The secondary optical system 74 is an optical system to which the secondary electrons emanated from the sample W are introduced, which comprises a lens system composed of two stages of electrostatic lenses 741 disposed in an upper side of the E.times.B type deflecting system of the primary optical system. A detector 761 detects the secondary electrons sent through the secondary optical system 74. Since the structures and functions of respective components of said optical systems 760 and said detector 761 are similar to those in the prior art, a detailed description thereof should be omitted.

The charged particles beam emitted from the electron gun 721 is appropriately shaped in a square aperture below the electron gun, contracted by the lens system of two stages of lenses 722, and then, after the optical axis thereof is adjusted by the deflector 730, the charged particles beam is formed into an image of 1.25 mms square on a deflection principal plane of the E.times.B deflecting system 723. The E.times.B deflecting system 723 is designed such that an electric field and a magnetic field are crossed within a plane orthogonal to a normal line of the sample, wherein when the relationship among the electric field, the magnetic field and the energy of electrons satisfies a certain condition, the electrons are advanced straight ahead, and for any case other than the above, the electrons are deflected into a predetermined direction depending on said mutual relationship among the electric field, the magnetic field and the energy of electrons. In FIG. 40, the relationship is set so that the charged particles beam from the electron gun can enter the sample W at right angles and the secondary electrons emanated from the sample can be advanced directly toward the detector 761. The shaped beam, after being deflected in the E.times.B deflecting system, is contracted to ⅕ in size with the lens system composed of the lenses 724 to be projected onto the sample W. The secondary electrons emanated from the sample W, which have the information of a pattern image, are magnified by the lens systems composed of the lenses 724 and the lenses 741 so as to form the secondary electron image on the detector 761. These four stages of magnifying lenses, which are composed of the lens system of the lenses 724 forming a symmetrical tablet lens and the lens system of the lenses 741 also forming another symmetrical tablet lens, make up the lenses of no distortion.

According to the subject embodiment, the following effects may be expected to obtain.

(A) Processing by the charged particles beam can be stably applied to a sample on the stage by employing a stage having a structure similar to one of the hydrostatic bearing type which is typically used in the atmospheric pressure (a stage supported by the hydrostatic bearing having no differential exhausting mechanism).

(B) Affection on the vacuum level in the charged particles beam irradiation region can be minimized, whereby the processing by the charged particles beam to the sample can be stabilized.

(C) An inspection apparatus that accomplishes positioning performance of the stage at low cost, with high precision and which provides a stable vacuum level in the irradiation region of the charged particles beam can be provided.

(D) An exposing apparatus that accomplishes positioning performance of the stage at low cost, with high precision and which provides a stable vacuum level in the irradiation region of the charged particles beam can be provided.

(E) A micro semiconductor circuit can be formed by manufacturing the semiconductor using an apparatus which accomplishes positioning performance of the stage with high precision and provides a stable vacuum level in the irradiation region of the charged particles beam.

Modified Embodiment of the Inspection Apparatus

Figure 41:
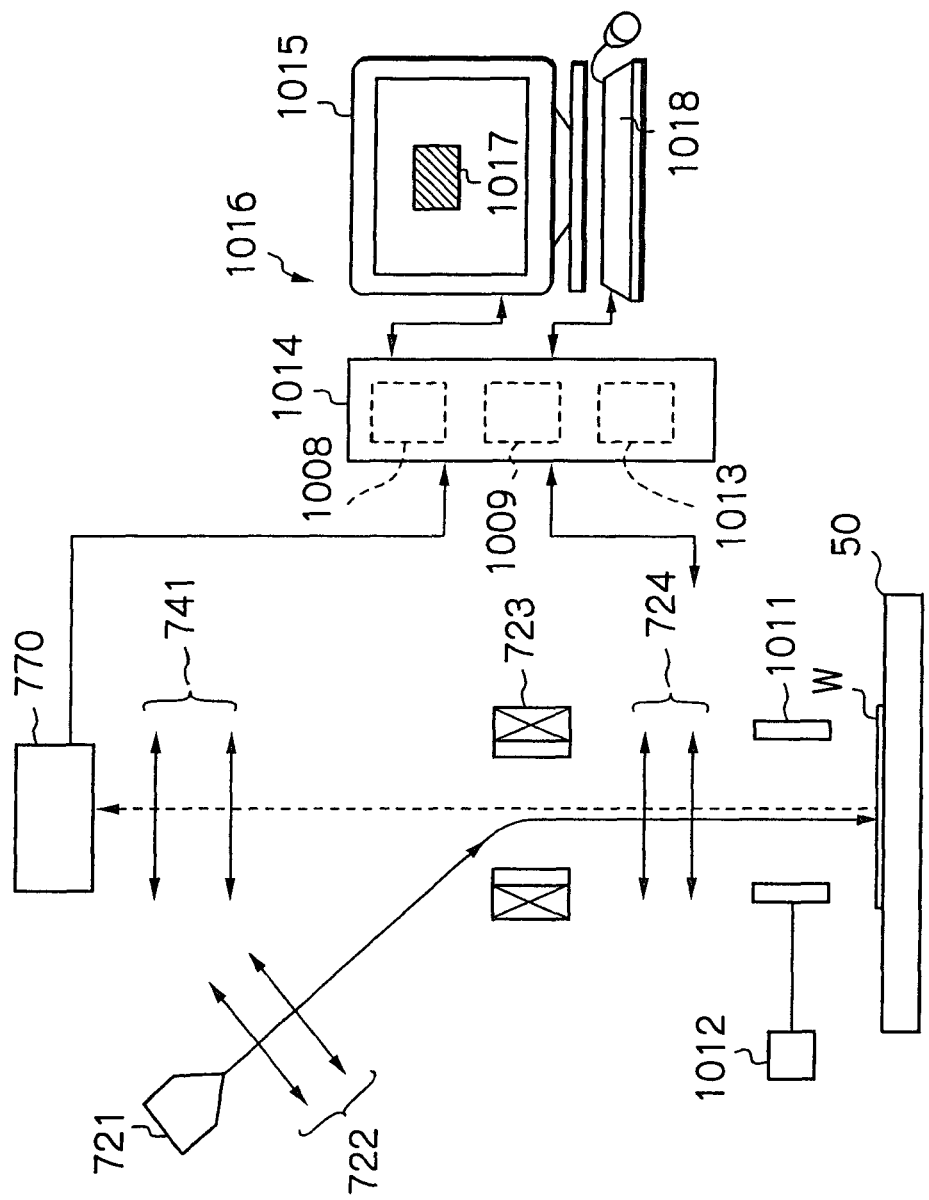
FIG. 41 is a schematic diagram illustrating an exemplary configuration of a defect inspection apparatus according to a modified embodiment of the present invention.

FIG. 41 shows a schematic configuration of a defect inspection apparatus according to the modified embodiment of the present invention. This defect inspection apparatus is explained above, i.e., a projective type inspection apparatus, which comprises: an electron gun 721 for emitting a primary electron beam; an electrostatic lens 722 for deflecting and forming the emitted primary electron beam; an E.times.B deflecting system 723 for deflecting the correspondingly formed primary electron beam at a field where an electric field "E" and a magnetic field "B" cross at right angles, so that the beam impinges against a semiconductor wafer W at an approximately right angle; an objective lens 724 for forming the deflected primary electron beam into an image on the wafer W; a stage 50 arranged in a sample chamber (not shown) allowed to be evacuated to vacuum and capable of moving within a horizontal plane with the wafer loaded thereon; an electrostatic lens 741 in a projection system for projecting at a predetermined magnification a secondary electron beam and/or a reflected electron beam emitted from the wafer W upon the irradiation of the primary electron beam to be formed into an image; a detector 770 for detecting the formed image as a secondary electron image of the wafer; and a control section 1016 for controlling the whole unit of the apparatus and for performing the process for detecting a defect in the wafer W based on the secondary electron image detected by the detector 770, as well. It is to be noted that the present specification has designated said image as the secondary electron image, although said secondary electron image is actually affected by not only the secondary electrons but also the back scattered and reflected electrons.

Further, between the objective lens 724 and the wafer W, there is arranged a deflecting electrode 1011 for deflecting an incident angle of the primary electron beam onto the wafer W by the electric field or the like. This deflecting electrode 1011 is connected to a deflection controller 1012 for controlling the electric field of said deflecting electrode. This deflection controller 1012 is connected to the control section 1016 to control the deflecting electrode 1011 so that the electric field may be generated by said deflecting electrode 1011 in response to a command from the control section 1016. It is to be noted that the deflection controller 1012 may be a voltage controller for controlling a voltage applied to the deflecting electrode 1011.

The detector 770 may have any arbitrary configuration so long as it can convert the secondary electron image formed by the electrostatic lens 741 into a signal capable of being processed later. For example, as shown in detail in FIG. 46, the detector 770 may comprise a multi-channel plate 751, a fluorescent screen 772, a relay optical system 773, and an image sensor 774 composed of a plurality of CCD elements. The multi-channel plate 751 comprises a plurality of channels within the plate so as to generate more electrons during the secondary electrons formed into the image by the electrostatic lens 741 passing through those channels. That is, the multi-channel plate 751 amplifies the secondary electrons. The fluorescent screen 772 radiate fluorescence by the amplified secondary electrons to convert the secondary electrons into light (fluorescence). The relay lens 773 guides said fluorescence to the CCD image sensor 774, and then said CCD image sensor 774 converts the intensity distribution of the secondary electrons on the surface of the wafer W to an electric signal, i.e., a digital image data for each element, which in turn is output to the control section 1016.

The control section 1016, as shown in FIG. 41, may be composed of a general-purpose computer or the like. This computer may comprise a control section main unit 1014 for executing various controls and operations according to a predetermined program, a CRT 1015 for displaying processed results from the main unit 1014, and an input section 18 such as a mouse and a keyboard used by an operator for inputting a command; of course, said control section 1016 may be composed of a piece of hardware working exclusively as a defect inspection apparatus, namely a work station, or the like.

The control section main unit 1014 may comprise various control substrates such as a CPU, RAM, ROM, a hard disk, and a video substrate, which are not illustrated. A secondary electron image storage region 1008 is allocated memory such as RAM or that on a hard disk, for storing the electric signal received from the detector 770, i.e., the digital image data for the secondary electron image of the wafer W. Further, on the hard disk, there is a reference image storage section 1013 for storing beforehand reference image data for wafers having no defects. Still further, on the hard disk, in addition to the control program for controlling the whole unit defect inspection apparatus, a defect detection program 1009 is stored for reading the secondary electron image data from the storage region 1008 and automatically detecting a defect in the wafer W based on said image data according to the predetermined algorithm. This defect detection program 1009, as will be described in more detail later, has a function that enables it to perform a matching of the reference image read out from the reference image storage section 1013 with an actually detected secondary electron image in order to automatically detect any defective parts, so that it may indicate a warning to the operator when it determines there is a defect. In this regard, the CRT 1015 may be designed to also display the secondary electron image 1017 on the display section thereof.

Figure 43:
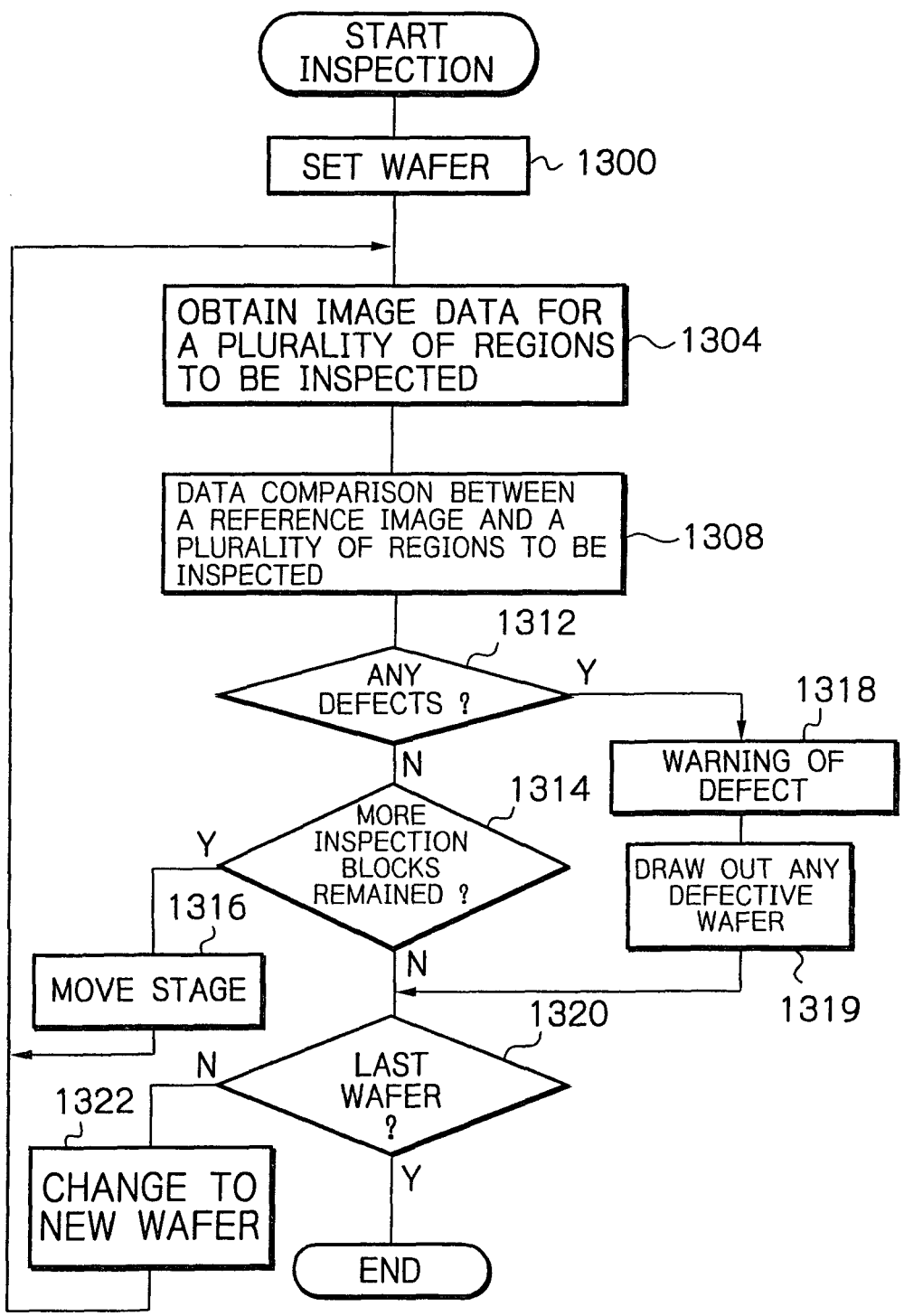
FIG. 43 is a flow chart illustrating the flow of the main routine for wafer inspection in the defect inspection apparatus of FIG. 41.
Figure 44:
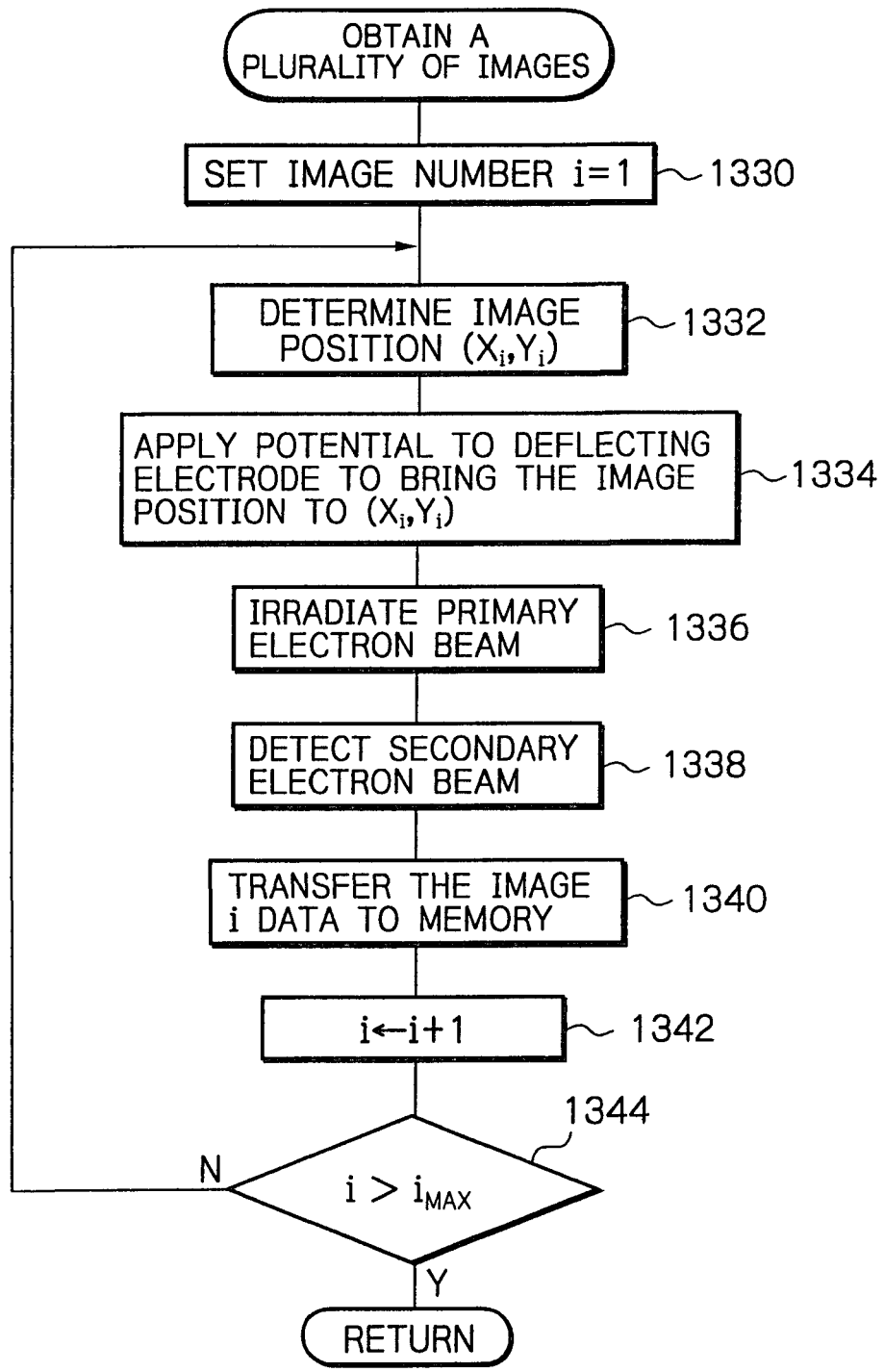
FIG. 44 is a flow chart illustrating the detailed flow of a sub-routine in the process for obtaining image data for a plurality of regions to be inspected (step 1304) of FIG. 43.
Figure 45:
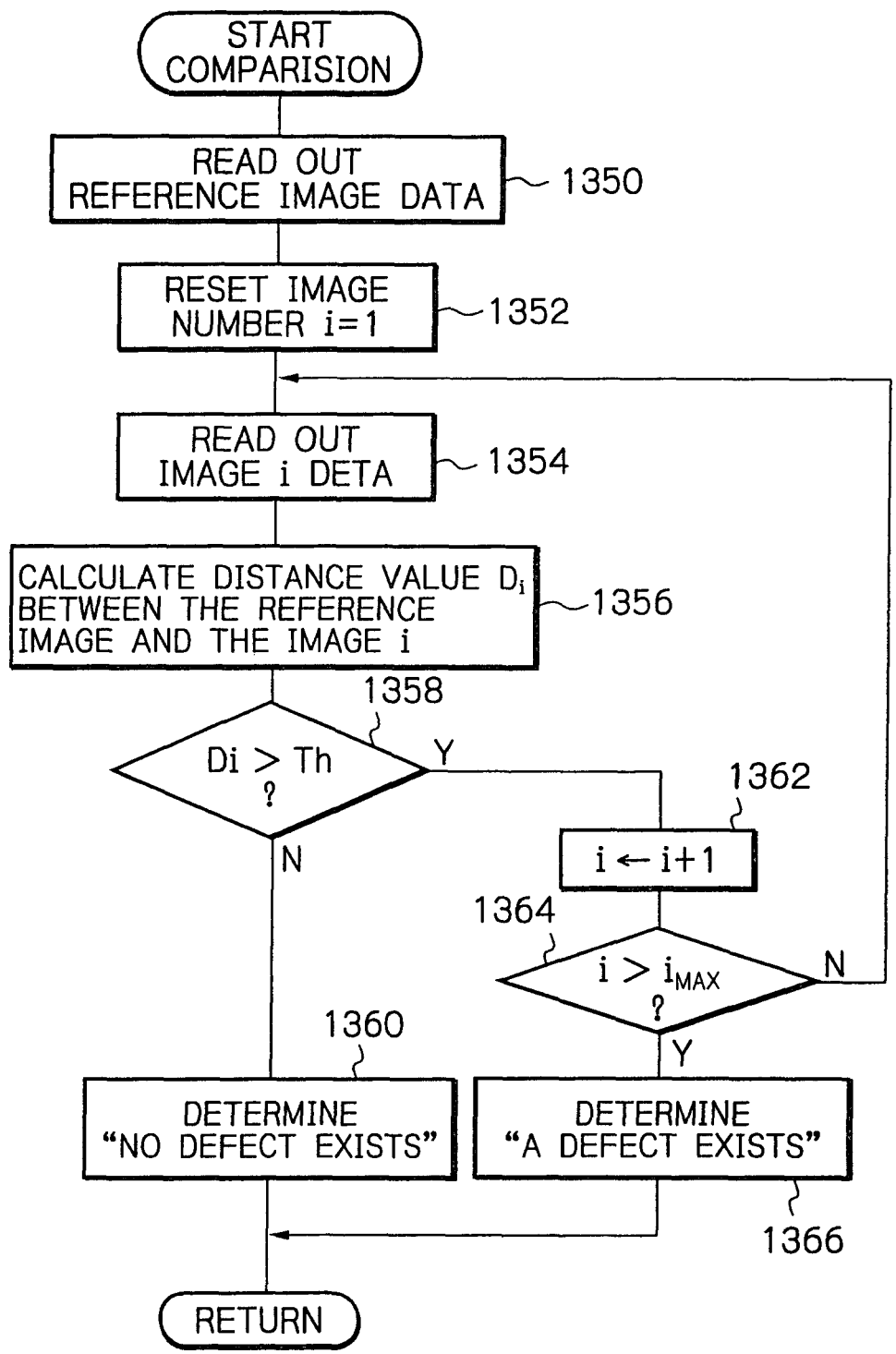
FIG. 45 is a flow chart illustrating the detailed flow of a sub-routine in the comparing process (step 1308) of FIG. 43.

Then, the operation of the defect inspection apparatus according to the modified embodiment will be exemplarily described referring to the flow charts of FIGS. 43 to 45.

First of all, as shown in the flow of the main routine of FIG. 43, the wafer W to be inspected is placed on the stage 50 (step 1300). In this regard, the way of setting the wafer W may be such that each of a plurality of wafers W contained in a loader is set on the stage 50 automatically one by one as explained above.

Figure 47:
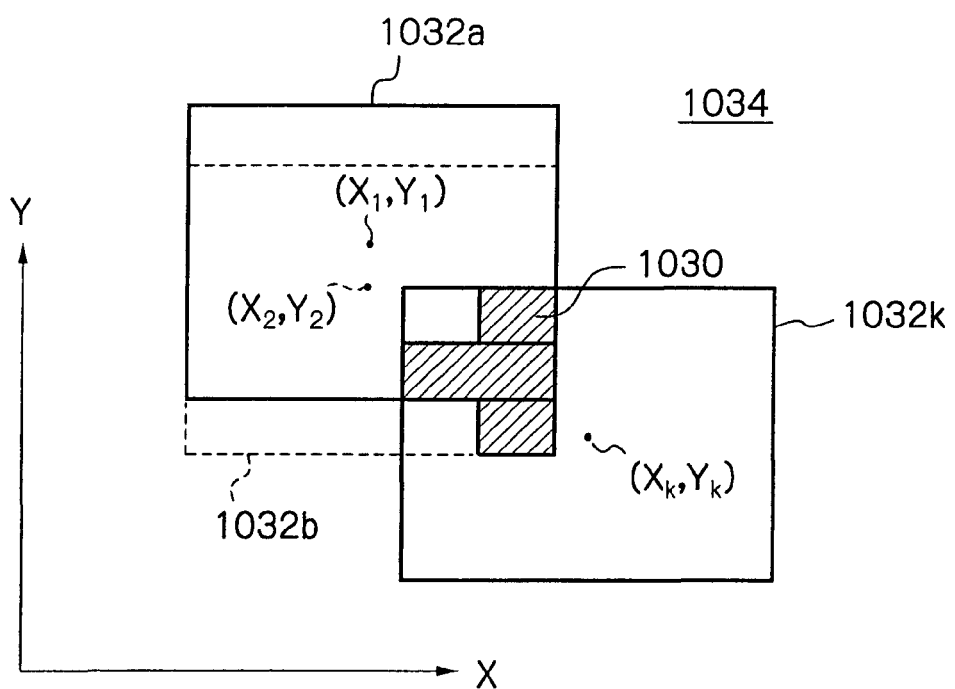
FIG. 47 is a schematic diagram illustrating a plurality of regions to be inspected which are displaced one from another while being partially superimposed one on another on the semiconductor wafer surface.

Then, images for a plurality of regions to be inspected are respectively obtained, which are displaced one from another while being superimposed partially one on another on the XY plane of the surface of the wafer W (Step 1304). Each of said plurality of regions to be inspected, from which the image is to be obtained, is a rectangular region as designated by reference numerals 1032a, 1032b, ... 1032k, ..., each of which is observed to be displaced relative to another while being partially superimposed on each another around the inspection pattern 1030 of the wafer as shown in FIG. 47. For example, 16 pieces of images 1032 for the regions to be inspected (the images to be inspected) may be obtained as shown in FIG. 42. Herein, for the image as shown in FIG. 42, each square contained in the rectangular region corresponds to one pixel (or a block, whose unit is greater than the unit of pixel), and among those squares, shaded ones correspond to the imaged area of the pattern on the wafer W. This step 1304 will be described in more detail later with reference to the flow chart of FIG. 44.

Then the process compares the image data for the plurality of regions to be inspected, which have been obtained at Step 1304, respectively with the reference image stored in the storage section 1013 to look for any matches (Step 1308 in FIG. 43), and determines whether or not there is a defect existing in the wafer inspection plane encompassed by said plurality of regions to be inspected. This process performs what is called the matching operation between images, which will be explained later in detail with reference to the flow chart shown in FIG. 45.

If the result from the comparing process at Step 1308 indicates that there is a defect in the wafer inspection plane encompassed by said plurality of regions to be inspected (Step 1312, affirmative determination), the process gives a warning to the operator indicating the existence of the defect (Step 1318). As for the way of warning, the display section of the CRT 1015 may, for example, display a message notifying the operator that there is a defect, or at the same time may additionally display a magnified image 1017 of the pattern determined to have the defect. Such defective wafers may be immediately taken out of a sample chamber 31 and stored in another storage area separately from those wafers having no defects (Step 1319).

If the result from the comparing process at Step 1308 indicates that there is no defect in the wafer W (Step 1312, negative determination), the process determines whether or not there remain more regions to be inspected for the current wafer W currently treated as the inspection object (Step 1314). If there are more regions remaining for inspection (Step 1314, affirmative determination), the stage 50 is driven to move the wafer W so that other regions to be further inspected are positioned within the irradiative region of the primary electron beam (Step 1316). Subsequently, the process goes back to Step 1302 to repeat similar operations for said other regions to be inspected.

If no more regions remain to be inspected (Step 1314, negative determination), or after a drawing out processing of the defective wafer (Step 1319), the process determines whether or not the current wafer treated as the inspection object is the last wafer to be inspected, that is, whether or not there are any wafers remaining for the inspection in the loader, (though not shown) (Step 1320). If the current wafer is not the last one (Step 1320, negative determination), the wafers inspected already are stored in a predetermined storage location, and a new wafer which has not been inspected yet is set instead on the stage 50 (Step 1322). Then, the process goes back to Step 302 to repeat similar operations for said wafer. In contrast, if the current wafer is the last one (Step 320, affirmative determination), the wafer just inspected is stored in the predetermined storage location to end the whole process.

Then, the process flow of step 1304 will now be described with reference to the flow chart of FIG. 44.

In FIG. 44, first of all, an image number "i" is set to the initial value "1" (Step 1330). This image number is an identification number assigned serially to each of the plurality of images for the regions to be inspected. Secondary, the process determines an image position ($X_i, Y_i$) for the region to be inspected as designated by the set image number i (Step 1332). This image position is defined as a specific location within the region to be inspected for bounding said region, for example, a central location within said region. Currently, i=1 defines the image position as (X.sub.1, Y.sub.1), which corresponds, for example, to a central location of the region to be inspected 1032a as shown in FIG. 47. The image position has been determined previously for every image region to be inspected, and stored, for example, in the hard disk of the control section 1016 to be read out at Step 1332.

Then, the deflection controller 1012 applies a potential to the deflecting electrode 1011 (Step 1334 in FIG. 44) so that the primary electron beam passing through the deflecting electrode 1011 of FIG. 41 may be irradiated against the image region to be inspected in the image position (X.sub.i, Y.sub.i) determined at Step 1332.

Then, the electron gun 721 emits the primary electron beam, which goes through the electrostatic lens 722, the E.times.B deflecting system 723, the objective lens 724 and the deflecting electrode 1011, and eventually impinges upon a surface of the set wafer W (Step 1336). At that time, the primary electron beam is deflected by an electric field generated by the deflecting electrode 1011 so as to be irradiated onto the wafer inspection surface 1034 covering the whole image region to be inspected at the image position (X.sub.i, Y.sub.i). When i=1, the region to be inspected is 1032a.

The secondary electrons and/or the reflected electrons (hereafter referred exclusively to as "secondary electrons" for simplicity) are emitted from the region to be inspected, to which the primary electron beam has been irradiated. Then, the generated secondary electron beam is formed into an image on the detector 770 at a predetermined magnification by the electrostatic lens 741 of a magnifying projection system. The detector 770 detects the imaged secondary electron beam, and converts it into an electric signal for each detecting element, i.e., digital image data (Step 1338). Then, the detected digital image data for the image number i is sent to the secondary electron image storage region 1008 (Step 1340).

Subsequently, the image number i is incremented by 1 (Step 1342), and the process determines whether or not the incremented image number (i+1) is greater than a constant value "i.sub.MAX" (Step 1344). This i.sub.MAX is the number of images to be inspected that must be obtained, which is "16" for the above example of FIG. 42.

If the image number i is not greater than the constant value i.sub.MAX (Step 1344, negative determination), the process goes back to Step 332 again, and determines again the image position (X.sub.i+1, Y.sub.i+1) for the incremented image number (i+1). This image position is a position moved from the image position (X.sub.i, Y.sub.i) determined by the previous routine by a specified distance (.DELTA.X.sub.i, .DELTA.Y.sub.i) in the X direction and/or Y direction. The region to be inspected in the example of FIG. 41 is at the location (X.sub.2, Y.sub.2), i.e., the rectangular region 1032b indicated with the dotted line, which has been moved from the position (X.sub.1, Y.sub.1) only in the Y direction. It is to be noted that the value for (.DELTA.X.sub.i, .DELTA.Y.sub.i) (i=1, 2, . . . i.sub.MAX) may have been appropriately determined from the data indicating practically and experimentally the displacement of the pattern 1030 on the wafer inspection surface 1034 from the field of view of the detector 770 and the number and the area of the regions to be inspected.

Then, the operations for Step 1332 to Step 1342 are repeated in order for i.sub.MAX regions to be inspected. These regions to be inspected are continuously displaced while being partially superimposed one on another on the wafer inspection surface 1034 so that the image position after k times of movements (X.sub.k, Y.sub.k) corresponds to the inspection image region 1032k, as shown in FIG. 47. In this way, the 16 pieces of inspection image data illustrated in FIG. 42 are captured in the image storage region 1008. It is observed that a plurality of images 1032 obtained for the regions to be inspected (i.e., inspection image) contains partially or fully the image 1030a of the pattern 1030 on the wafer inspection surface 1034, as illustrated in FIG. 42.

If the incremented image number i has become greater than i.sub.MAX (Step 1344, affirmative determination), the process returns from this subroutine and goes to the comparing process in the main routine of FIG. 37 (Step 1308).

It is to be noted that the image data that has been transferred to the memory at Step 1340 is composed of intensity values of the secondary electrons for each pixel (so-called, raw data), and this data may be stored in the storage region 1008 after having been processed through various operations in order for use in performing the matching operation relative to the reference image in the subsequent comparing process (Step 1308 of FIG. 43). Such operations include, for example, a normalizing process for setting the size and/or density of the image data to be matched with the size and/or the density of the reference image data, or a process for eliminating as noise an isolated group of elements having a number of pixels not greater than the specified number. Further, the image data may be converted by means of data compression into a feature matrix that contains extracted features of the detected pattern rather than the simple raw data, as long as it does not negatively affect the accuracy in detection of the highly precise pattern. Such a feature matrix includes, for example, an m.times.n feature matrix, in which a two-dimensional inspection region composed of M.times.N pixels is divided into m.times.n (m<M, n<N) blocks, and respective sums of intensity values of the secondary electrons of the pixels contained in each block (or the normalized value defined by dividing said respective sums by the total number of pixels covering all of the regions to be inspected) should be employed as respective components of the matrix. In this case, the reference image data also should have been stored in the same representation. The image data in the context used in the embodiment of the present invention includes, of course, simple raw data but also includes any image data having features extracted by any arbitrary algorithms as described above.

The process flow for Step 1308 will now be described with reference to the flow chart of FIG. 45.

First of all, the CPU in the control section 1016 reads the reference image data out of the reference image storage section 1013 (FIG. 41) into a working memory such as RAM or the like (Step 1350). This reference image is identified by reference numeral 1036 in FIG. 42. Then, the image number "i" is reset to 1 (Step 1352), and the process reads out from the storage region 1008 the inspection image data having the image number i into the working memory (Step 1354).

Then, the read-out reference image data is compared with the data of the image i for matching to calculate a distance value "D.sub.i" between the reference and image i (Step 356). This distance value D.sub.i indicates a similarity level between the reference image and the image to be inspected "i", wherein a greater distance value indicates a greater difference between the reference image and the inspection image. Any unit of measurement representative of the similarity level may be used for said distance value D.sub.1. For example, if the image data is composed of M.times.N pixels, the process may consider that the secondary electron intensity (or the measurement representative of the feature) for each pixel is a position vector component of M.times.N dimensional space, and then calculate a Euclidean distance or a correlation coefficient between the reference image vector and the image i vector in the M.times.N dimensional space. It will be easily appreciated that any distance other than Euclidean distance, for example, the urban area distance may be calculated. Further, if the number of pixels is huge, which increases the amount of calculation significantly, then the process may calculate the distance value between both image data represented by the m.times.n feature vector as described above.

Subsequently, it is determined whether the calculated distance value $D_i$ is smaller than a predetermined threshold Th (Step 1358). This threshold Th is determined experimentally as a criterion for judging sufficient matching between the reference image and the inspection image.

If the distance value $D_i$ is smaller than the predetermined threshold Th (Step 1358, affirmative determination), the process determines that the inspection plane 1034 of said wafer W has "no defect" (Step 1360) and returns from this subroutine. That is, if there is found at least one image among those inspection images matching to the reference image, the process determines there is "no defect". Accordingly, since the matching operation is not necessarily be applied to every inspection image, high-speed judgment becomes possible. As for the example of FIG. 42, it is observed that the image to be inspected at column 3 of the row 3 approximately matches the reference image without any offset thereto.

When the distance value $D_i$ is not smaller than the threshold Th (Step 1358, negative determination), the image number i is incremented by 1 (Step 1362), and then it is determined whether or not the incremented image number (i+1) is greater than the predetermined value $i_{MAX}$ (Step 1364).

If the image number i is not greater than the predetermined value $i_{MAX}$ (Step 1364 negative determination), the process goes back to Step 1354 again, reads out the image data for the incremented image number (i+1), and repeats similar operations.

If the image number i is greater than the predetermined value $i_{MAX}$ (Step 1364, affirmative determination), then the process determines that said inspection plane 1034 of said wafer W has "a defect existing" (Step 1366), and returns from the subroutine. That is, if any one of the images to be inspected does not approximately match the reference image, the process determines that there is "a defect existing".

Although the defect inspection apparatus has been described with specific embodiments, it is to be apprehended that the present invention is not limited only to the above embodiments but also may be modified arbitrarily and preferably without departing from the scope and spirit of the present invention.

For example, although the description has illustratively employed a semiconductor wafer W as a sample to be inspected, the sample to be inspected in the present invention is not limited to this. Anything may be selected as the sample as long as it can be inspected for defects by using the electron beam. For example, the object to be inspected may be a mask with an exposure pattern formed thereon.

Further, the present invention may be applied not only to an apparatus which detects any defects with charged particle beams other than electrons but also to any apparatus which allows images to be obtained for inspecting the sample for defects.

Still further, the deflecting electrode 1011 may be disposed not only between the objective lens 724 and the wafer W but also at any arbitrary location as long as the irradiation region of the primary electron beam can be controlled. For example, the deflecting electrode 1011 may be disposed between the E.times.B deflecting system 723 and the objective lens 724, or between the electron gun 721 and the E.times.B deflecting system 723. Further, the E.times.B deflecting system 723 may control the deflecting direction by controlling the field generated thereby. That is, the E.times.B deflecting system 723 may function also as the deflecting electrode 1011.

Further, although in the above embodiment, either one of matching between the pixels and matching between the feature vectors can be employed for the matching operation between image data, they may also be combined. For example, a much faster and more precise matching process can be constructed by two-step matching, in which firstly a high-speed matching is performed with the feature vectors, which requires fewer operations, and subsequently a more precise matching is performed with more detailed pixel data for the images to be inspected that have been found to be quite similar.

Still further, although in the embodiments of the present invention, the position mismatch for the image to be inspected has been resolved only by displacing the irradiating region of the primary electron beam, the present invention may be combined with a process for retrieving an optimal matching region on the image data before or during the matching processes (e.g., first detecting the regions having higher correlation coefficients and then performing the matching). This can improve the accuracy of defect detection, because the major position mismatch for the image to be inspected is rectified by displacing the irradiating region of the primary electron beam, while the relatively minor position mismatch can be absorbed subsequently with the digital image processing.

Yet further, although the configurations for an electron beam apparatus for defect detection have been illustratively shown in FIG. 41, the electron optical systems or the like may be preferably and arbitrarily modified as long as they function well. For example, although the electron beam irradiation means (721, 722, 723) shown in FIG. 41 has been designed so as to irradiate the primary electron beam onto the surface of the wafer W at a right angle from above, the E.times.B deflecting system 723 may be omitted so that the primary electron beam may diagonally impinge upon the wafer W.

Still further, the flow in the flow chart of FIG. 43 is also not limited to the illustrated one. For example, although in the embodiment the process does not further perform defect detection in any other regions of the sample that have been determined to have a defect at Step 1312, the flow may be modified so that the overall area can be inspected for any defects to be detected. Yet further, if the irradiating area of the primary electron beam can be expanded so as to cover almost the entire area of the sample with one shot of irradiation, Steps 1314 and 1316 can be omitted.

As described above in detail, according to the defect inspection apparatus of the modified embodiment, since a defect in the sample can be detected by first obtaining respective images of a plurality of regions to be inspected, which are displaced from one another while being partially superimposed one on another on the sample, and comparing those images of the regions to be inspected with the reference image, therefore an advantageous effect can be provided in that the accuracy of defect detection can be maintained.

Further, according to the device manufacturing method of the modified embodiment, since defect detection is performed by using a defect inspection apparatus as described above, another advantageous effect can be provided in that the yield of the products can be improved and faulty products need not be delivered.

Other Embodiments of an Electron Beam Apparatus

Further, there is another method attempting to solve the problem associated with this projecting method, in which a plurality of electron beams is used to scan a sample surface in an observation region while performing a scanning operation in two dimensions (X-Y directions, that is, raster scanning), and a projecting type of secondary electron-optical system has been employed therefor. That method preserves the benefits of the above-described projecting method, while still solving the problems associated with the projecting method by using a plurality of electron beams for scanning, said problem including the facts: (1) charging may easily occur on a sample surface because of irradiation of electron beam being made at once; and (2) the inspection speed is hard to improve since an electron beam current obtained by this method is limited (to around 1.6 .mu.A). That is, since the electron beam irradiating point is moved, electric charge is more likely to escape and thereby the charging is decreased. Further, increasing the number of the plurality of electron beams makes it easier to increase the current value. It has been observed in the embodiment which uses four electron beams, that the current for one electron beam is 500 nA (with a beam diameter of 10 .mu.m) and a total of 2 .mu.A can be obtained. The number of beams of electrons can be easily increased to about 16, and in that case, it is possible in principle to obtain a total of 8 .mu.A. As for scanning by a plurality of electron beams, it is only required that the irradiation amount using the plurality of electron beams is kept uniform over the irradiation region, so that scanning is not limited to the above-mentioned raster scanning but can use other scanning patterns such as Lissajous' figures. Accordingly, the direction in which the stage moves is not required to be normal to the scanning direction of the plurality of electron beams.

Electron Gun (Electron Beam Source)

A thermal electron beam source has been employed as an electron beam source to be used in this embodiment. The electron emitting (emitter) material is L.sub.aB.sub.6. Other materials may be used as long as they have a high melting point (lower vapor pressure at higher temperature) and a low work function. Two methods are used in order to obtain a plurality of electron beams. In one method, a single electron beam is derived from a single emitter (with one projection) and then is passed through a thin plate having a plurality of apertures formed therein (an aperture plate) to obtain a plurality of electron beams, while in the other method, a single emitter is provided with a plurality of projections formed therein, from which a plurality of electrons is directly derived. Either case takes advantage of the property that an electron beam tends to be emitted from the tip portion of a projection. Electron beam sources of other methods, for example, an electron beam of thermal field emission type, may also be usable.

It is to be appreciated that the thermal electron beam source is one in which the electron emitting member is heated to emit an electron, while the thermal field emission electron beam source is one in which a high electric field is applied to the electron emitting member to emit electrons and further the electron emitting section is heated so as to stabilize emission of electrons.

Figure 48:
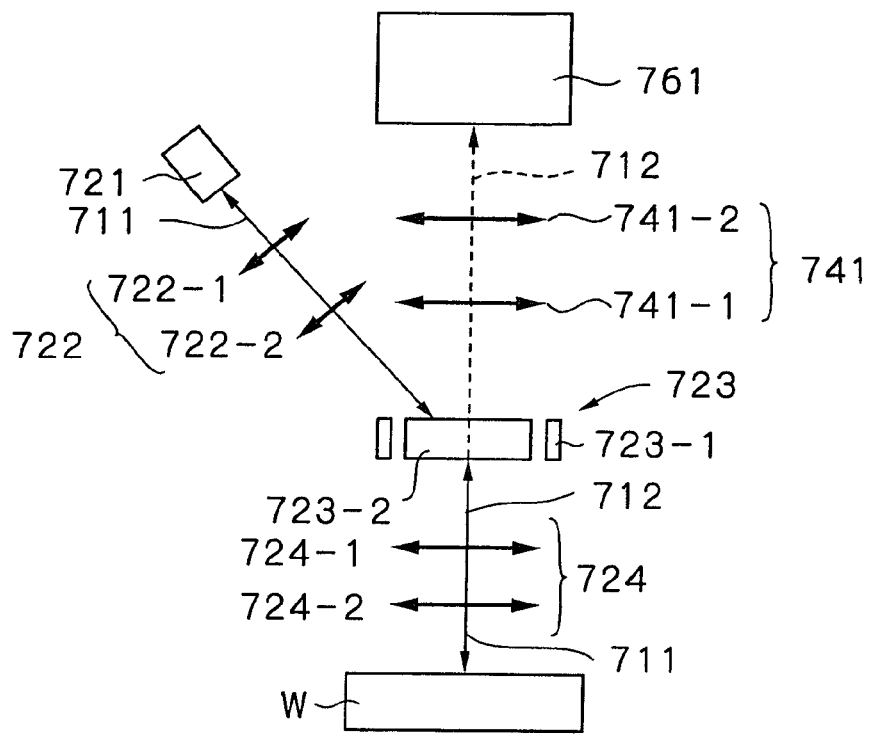
FIG. 48A is a schematic diagram of an electron beam apparatus according to another embodiment of the present invention.
FIG. 48B is a schematic plan view illustrating an aspect where a plurality of primary electron beams is scanning a sample in the apparatus of the embodiment shown in FIG. 48A.
Figure 48:
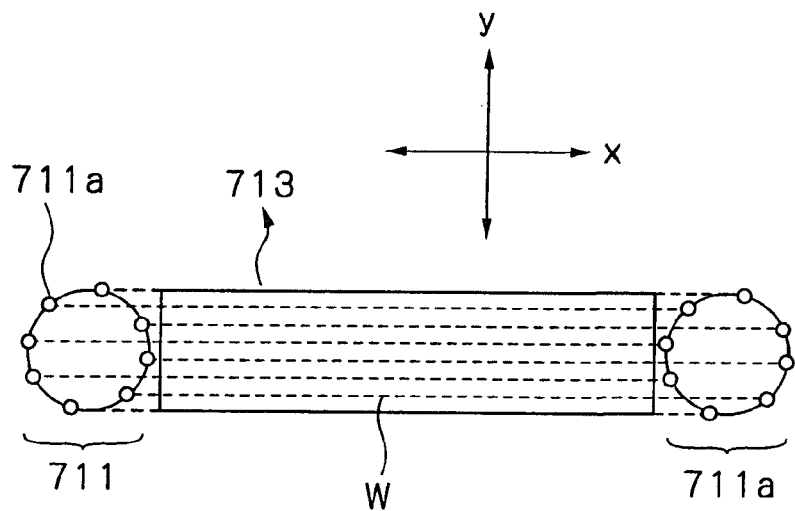

FIG. 48A is a schematic view of an electron beam apparatus according to the embodiment of the present invention. On the other hand, FIG. 48B is a schematic plan view illustrating an aspect of a plurality of primary electron beams scanning a sample. An electron gun 721 adapted to be operative with a space-charge limitation forms a multi-beam designated by reference numeral 711. The multi-beam 711 comprises primary electron beams 711*a* composed of 8 circular beams arranged on a circle.

A plurality of primary electron beams 711*a* generated in the electron gun 721 is focused by using lenses 722-1 and 722-2, and after being directed by an E.times.B deflecting system 723 consisting of an electrode 723-1 and a magnet 723-2, is made enter onto a sample W at a right angle. The multi-beam 711, which is composed of the plurality of primary electron beams 711*a* focused on the sample W by a primary optical system comprising those elements 711, 722-1, 722-2 and 723 and lenses 724-1 and 724-2, is used to scan the sample W by a two-step deflecting system disposed downstream to the lens 722-2 (not shown but included in the primary optical system).

The scanning of the sample W is performed in the x-axis direction with the principal surface of the objective lens 724-2 as the deflection center. As shown in FIG. 48B, the primary electron beams 711*a* of the multi-beam 711 are spaced apart from one another on the circle and designed so that when they are projected on the y-axis orthogonal to the x-direction or the scanning direction, the distances between any two adjacent primary electron beams 711*a* are equal (measured from the center of each primary electron beam) on the y-axis. At that time, those adjacent two primary electron beams 711*a* may be separated from each other, in contact with each other, or partially overlapped.

As shown in FIG. 48B, since the primary electron beams 711*a* forming the multi-beam 711 are arranged to be separated from one another, the current density threshold value for each of the primary electron beams 711*a*, that is, the critical current density value which would not cause any charges on the sample W, may be maintained at level equivalent to that in the case of a single circular beam being used, thereby keeping the S/N ratio high. Further, owing to the primary electron beams 711*a* being kept apart in this manner, the space-charge effect should also be low.

On the other hand, the multi-beam 711 can scan the sample W over the entire surface of a field of view 713 at a uniform density in one-time scanning. This allows images to be formed with high throughput and thus reducing the inspection time. In FIG. 48B, the reference numeral 711 designates the multi-beam at the starting point of scanning, while the reference numeral 711*a* designates the multi-beam at the end point of scanning.

The sample W is loaded on a sample table (not shown). During a scanning operation in the x-direction (for example, scanning with the scanning width of 200 .mu.m), the sample table is driven to move continuously along the y-direction so as to cross with the scanning direction "x" at a right angle. This accomplishes raster scanning. A drive means (not shown) is provided for moving the table with the sample loaded thereon.

Those secondary electrons, which emanated from the sample W at the time of scanning and emitted in different directions, are accelerated by the objective lens 724-2 in the optical axial direction and resultantly the secondary electrons that have been emitted from the respective points in the different directions are respectively focused to be narrower, and the spacing between images is increased through the lenses 724-1, 741-1 and 741-2. A secondary electron beam 712 that has been formed after passing through the secondary optical system including those lenses 724-1, 724-2, 741-1 and 741-2 is projected on the acceptance plane of a detector 761 and focused into an enlarged image of the field of view.

The detector 761 included in a light optical system uses a MCP (Micro Channel Plate) to multiply the secondary electron beam, and the multiplied secondary electron beam is then converted into an optical signal by a scintillator, which is further converted into an electric signal in a CCD detector. According to the electric signal from the CCD, a two-dimensional image for the sample W can be formed. Each of the primary electron beams 711a is designed to have a size equal to or greater than an area equivalent to two pixels in the CCD pixels.

Operating the electron gun 721 under the condition of the space-charge limitation allows the shot noise to be reduced by about one digit in comparison with the case of operation under the condition of the temperature limitation. Accordingly, the shot noise associated with the secondary electric signal can be also reduced by one digit, and thereby a signal with better S/N ratio may be obtained.

According to the electron beam apparatus of this embodiment, since the current density threshold value for primary electron beams that would not cause any charges on the sample may be maintained at an equivalent level to that in the case of a single circular beam being used, the inspection time may be shortened by forming images with higher throughput while preventing any deterioration in the S/N ratio.

Further, the device manufacturing method according to the present invention allows the yield thereof to be improved by evaluating the wafer at the ends of respective wafer processes using the electron beam apparatus described above.

Figure 49:
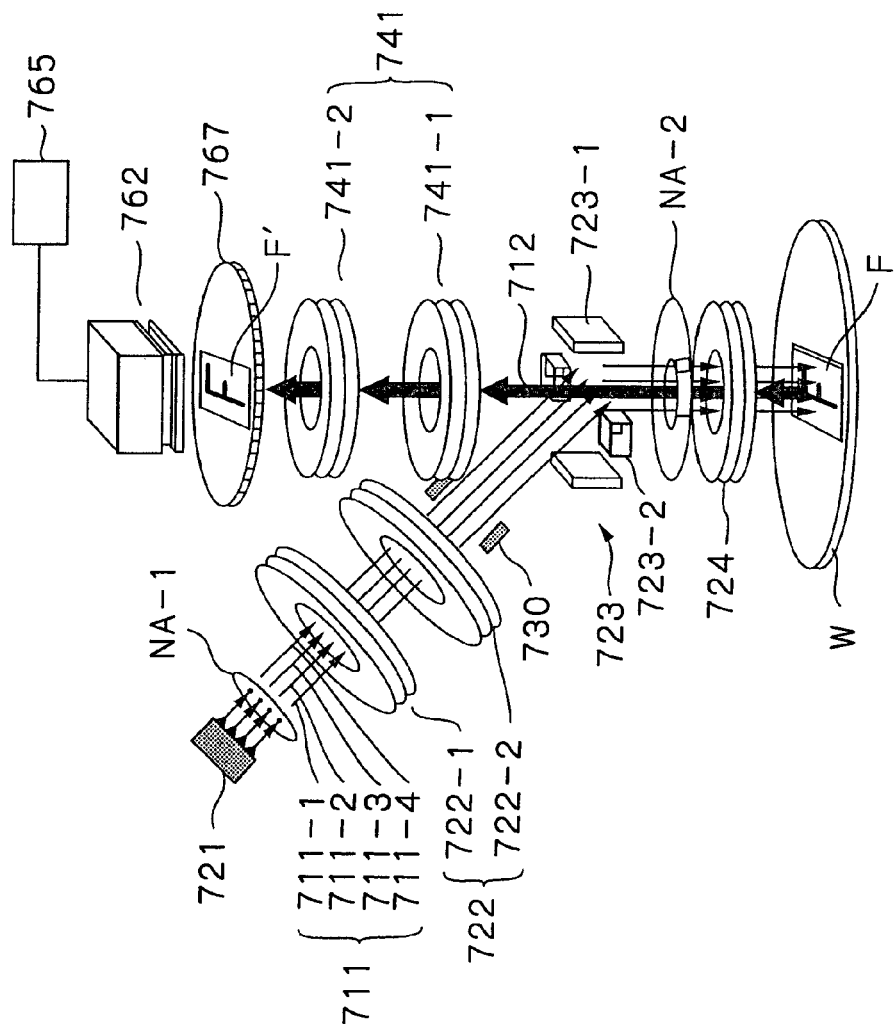
FIG. 49A is a view illustrating in more detail a configuration of the apparatus of the embodiment shown in FIG. 48A.
FIG. 49B is a view illustrating an irradiation method of the primary electron beam in the apparatus of the same embodiment.

FIG. 49A is a schematic diagram illustrating in detail the configuration of an electron beam apparatus of the embodiment shown in FIG. 48A. Four electron beams 711 (711-1, 711-2, 711-3 and 711-4) emitted from an electron gun 1 are shaped appropriately in an aperture diaphragm NA-1, formed into an image of elliptical shape of 10 .mu.m.times.12 .mu.m on a deflection principal plane of a Wien filter 723 by two stages of lenses 722-1 and 722-2, and used to make a raster-scanning operation in the vertical direction on paper of the drawing by the deflector 730 so as to be formed into an image for uniformly covering a rectangular region of 1 mm.times.0.25 mm with four electron beams as a whole. The plurality of electron beams that has been deflected by the E.times.B 723 are focused into a cross-over at the NA diaphragm, contracted into ⅕ in size with a lens 724, and then irradiated and projected so as to cover a sample W in an area of 200 .mu.m.times.50 .mu.m and so as to be normal to the sample surface (referred to as Koehler illumination). Four electron beams 712, each being emanat from the sample and having a data of pattern image (a sample image F), are magnified by the lenses 724, 741-1 and 741-2, and are altogether formed into a rectangular image (a magnified projection image F') synthesized by four electron beams 712 as a whole on a MCP 767. The magnified projection image F' synthesized from the secondary electron beams 712 is made to be sensitized up to 10,000 times in intensity by the MCP 767, converted into the light by a fluorescence section 767 and further converted by a TDI-CCD 762 into an electric signal synchronized with a speed of a serial movement of the sample, which signal is obtained by an image displaying section 765 as a series of images and is output to a CRT or the like.

An electron beam irradiating section is required to irradiate the sample surface more uniformly and further reduce unevenness during irradiation in a rectangular or elliptical shape with the electron beam, and is also required to irradiate the electron beam to the irradiation region with a higher current in order to increase throughput. An uniformity in irradiation associated with the prior art is about .+-.0.10%, where the uniformity in the image contrast is greater, while the electron beam irradiation current is as low as about 500 nA in the irradiation region, which has the problem in that a higher throughput is hard accomplish. Further, in comparison with a scanning electron microscope (SEM) method, the present method has been problematic in that a disorder in image formation due to a charging is more likely to occur because a larger image observation region is exposed at once to the electron beam irradiation.

Figure 49B:
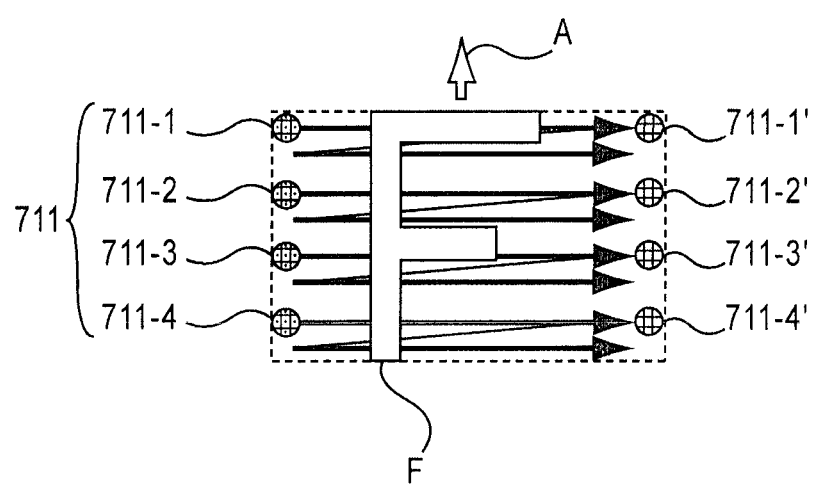

An irradiation method of the primary electron beam according to the present embodiment is shown in FIG. 49B. The primary electron beam 711 is composed of four electron beams 711-1, 711-2, 711-3 and 711-4, each of which is in the shape of an ellipse of 2 .mu.m.times.2.4 .mu.m and each one being capable of raster-scanning a rectangular region of 200 .mu.m.times.12.5 .mu.m, which are added together without overlapping one another, thus accomplishing the rectangular region of 200 .mu.m.times.50 .mu.m as a whole to be irradiated. The beam at the position 711-1 reaches the position 711-1' within a finite time and returns to the position immediate below the position 711-1 (in the direction 202) offset by a beam-spot diameter (10 .mu.m) with almost no time loss, and moves to the position immediately below the position 711-1' (in the direction 711-2') parallel to the line 711-1 to 711-1' again within a finite time as before, and after repeating the same movements to scan one quarter (200 .mu.m.times.12.5 .mu.m) of the rectangular irradiation region indicated by the dotted line, the beam returns back to the original position 711-1 and repeats the same movement at high speed. Other electron beams 711-2 to 711-4 repeat the scanning similarly to and at the same speed as the electron beam 711-1 and thus those beams altogether irradiate the rectangular region (200 .mu.m.times.50 .mu.m) in the drawing uniformly at high speed. As long as the uniform irradiation is achieved, a method other than said raster scanning might be used. For example, the scanning may be performed so as to draw a Lissajous figure. Accordingly, the direction of the stage movement is not limited to the direction A as indicated in the drawing. That is, the direction of the stage movement is not required to be normal to the scanning direction (fast scanning in the lateral direction in the drawing). The embodiment has accomplished the irradiation with electron beam irradiation uniformity of about .+-.0.3%. With the irradiation current of 250 nA per electron beam, four electron beams were used and the total current of 1.0 .mu.A was obtained on the sample surface (two times as high as that by the prior art). Increasing the number of electron beams allows the current to be increased and a higher throughput to be obtained. Further, since the irradiation point is smaller than that in the prior art (about {fraction (1/80)} in area) and also moving, the charging is successfully controlled so that it is no greater than {fraction (1/20)} of that in the prior art.

Although not illustrated in the drawing, the present apparatus comprises, in addition to the lenses, a limit field stop, a deflector (an aligner) having four or more poles for adjusting the axis of the electron beam, an astigmatism corrector (stigmator), and further units, such as a plurality of quadrupole lenses (four-pole lenses) for shaping the beam form and the like, which are necessary for illuminating and focusing the electron beam.

Device Manufacturing Method

Next, an embodiment of a method of manufacturing a semiconductor device according to the present invention will be described with reference to FIGS. 50 and 51.

Figure 50:
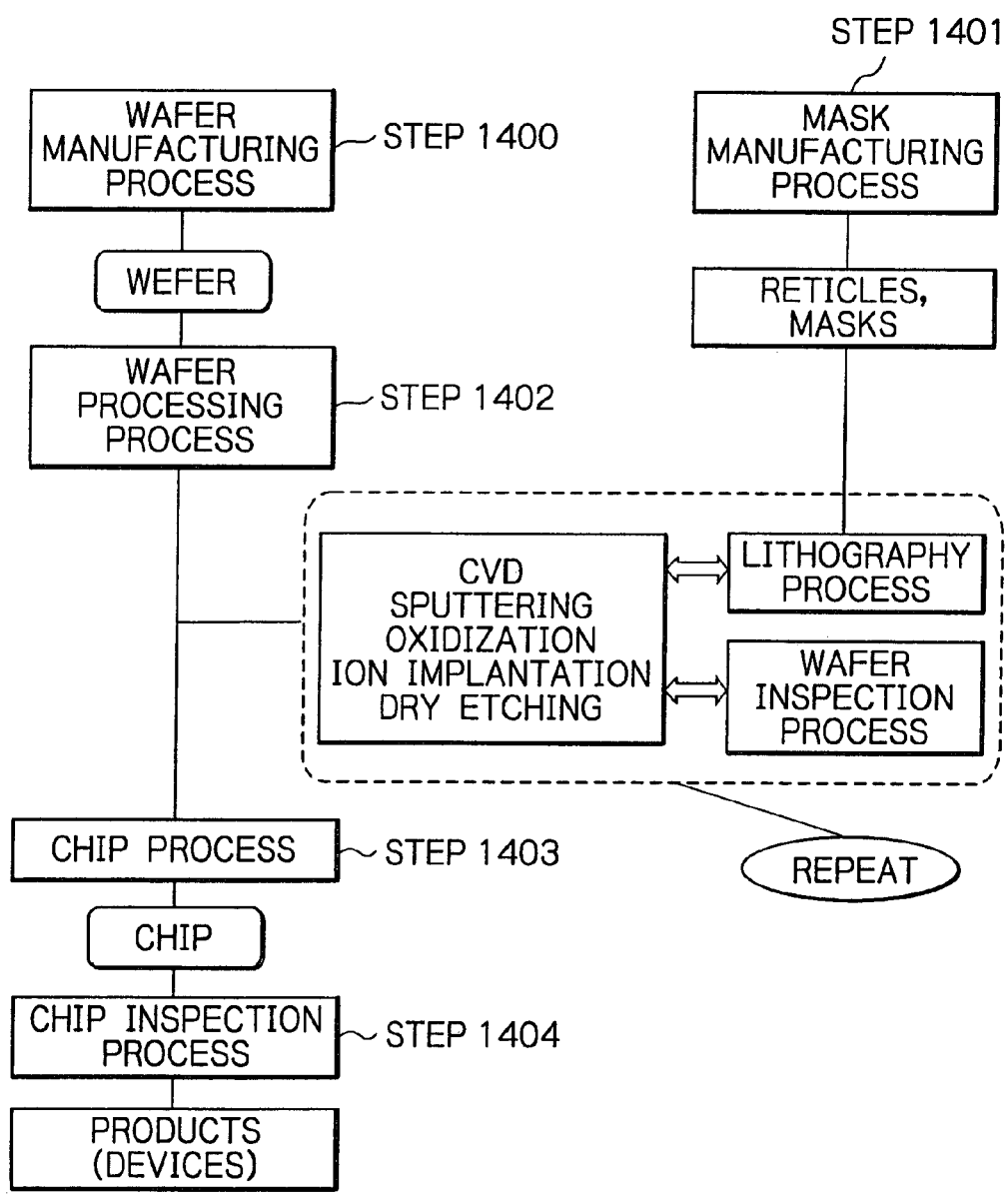
FIG. 50 is a flow chart illustrating an embodiment of a method of manufacturing a semiconductor device according to the present invention.

FIG. 50 is a flow chart illustrating an embodiment of a method of manufacturing a semiconductor device according to the present invention. Manufacturing processes of this embodiment include the following main processes:

(1) a wafer manufacturing process for manufacturing a wafer (or a wafer preparing process for preparing a wafer) (Step 1400);

(2) a mask manufacturing process for manufacturing masks to be used during the exposure (or mask preparing process for preparing masks) (Step 1401);

(3) a wafer processing process for performing any processing treatment necessary for the wafer (Step 1402);

(4) a chip assembling process for cutting out those chips formed on the wafer one by one to make them operable (Step 1403); and (5) a chip inspection process for inspecting finished chips (Step 1404).

The respective main processes are further comprised of several sub-processes.

Among these main processes, the wafer processing process set forth in (3) exerts a critical effect on the performance of resultant semiconductor devices. This process involves sequentially laminating designed circuit patterns on the wafer to form a large number of chips which operate as memories, MPUs and so on. The wafer processing process includes the following sub-processes:

(A) a thin film forming sub-process for forming dielectric thin films serving as insulating layers and/or metal thin films for forming wirings or electrodes, and the like (by using CVD, sputtering and so on);

(B) an oxidization sub-process for oxidizing the thin film layers and the wafer substrate;

(C) a lithography sub-process for forming a resist pattern by using masks (reticles) for selectively processing the thin film layers and/or the wafer substrate;

(D) an etching sub-process for processing the thin film layers and/or the wafer substrate in accordance with the resist pattern (by using, for example, dry etching techniques);

(E) an ion/impurity injection/diffusion sub-process;

(F) a resist striping sub-process; and (G) a sub-process for inspecting the processed wafer;

As can be appreciated, the wafer processing process is repeated a number of times depending on the number of required layers to manufacture semiconductor devices which operate as designed.

Figure 51A:
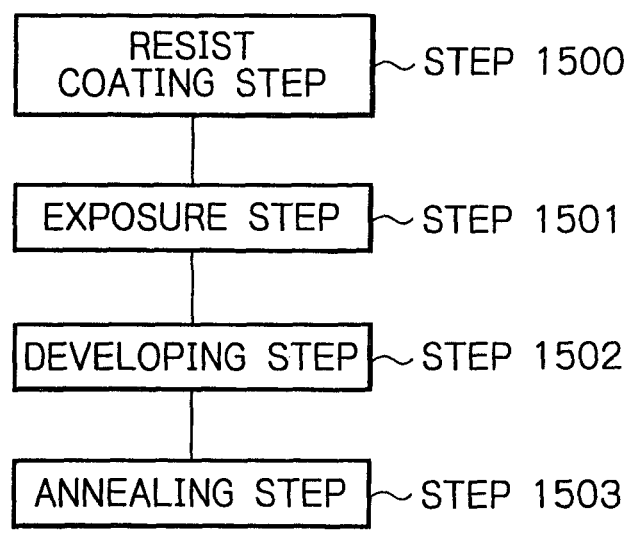
FIG. 51A is a flow chart illustrating a lithography subprocess which forms the core of a wafer processing process in FIG. 50.

FIG. 51A is a flow chart illustrating the lithography sub-process which forms the core of the wafer processing process in FIG. 50. The lithography sub-process includes the following steps:

(a) a resist coating step for coating a resist on the wafer on which circuit patterns have been formed in the previous process (Step 1500);

(b) an exposing step for exposing the resist (Step 1501);

(c) a developing step for developing the exposed resist to produce a resist pattern (Step 1502); and (d) an annealing step for stabilizing the developed resist pattern (Step 1503).

Since the aforementioned semiconductor device manufacturing process, wafer processing process and lithography process are well known, no further description is required.

When the defect inspection method and defect inspection apparatus according to the present invention are used in the inspection sub-process set forth in (G), any semiconductor devices, even those having miniature patterns, can be inspected at a high throughput, so that a total inspection can also be conducted, thereby making it possible to improve the yield rate of products and prevent defective products from being shipped.

Inspection Procedure

An inspection procedure in the inspection process (G) stated above is explained as follows.

Generally, since an inspection apparatus using an electron beam is expensive and the throughput thereof is rather lower than that provided by other processing apparatuses, this type of inspection apparatus is currently applied to a wafer after an important process (for example, etching, film deposition, or CMP (chemical and mechanical polishing) flattening process) to which it is considered that the inspection is required most.

Figure 51B:
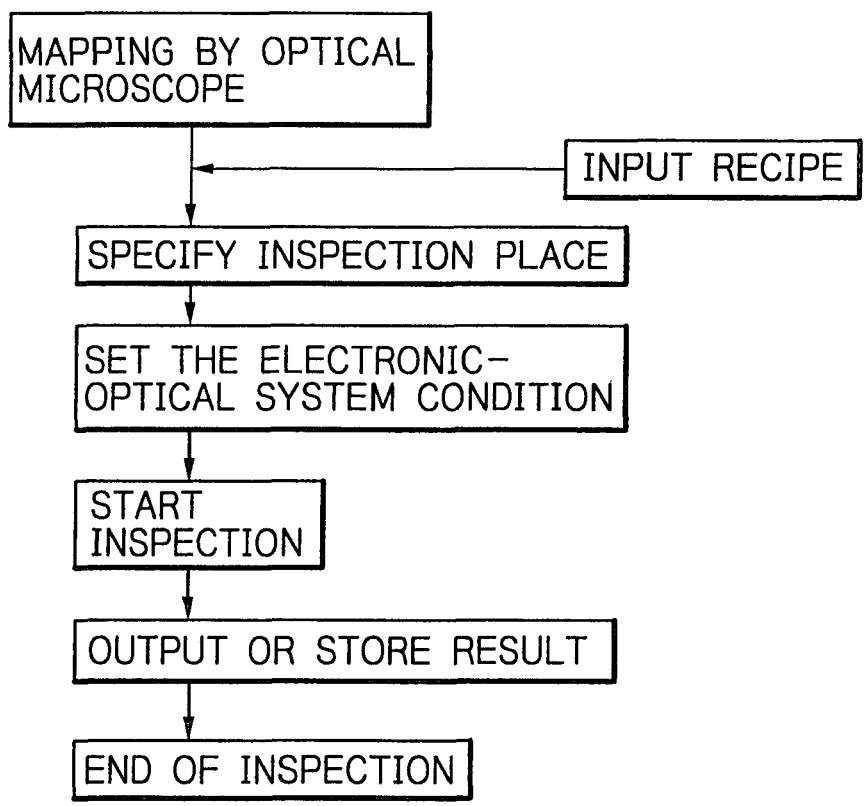
FIG. 51B is a procedure for defect inspection.
Figure 52:
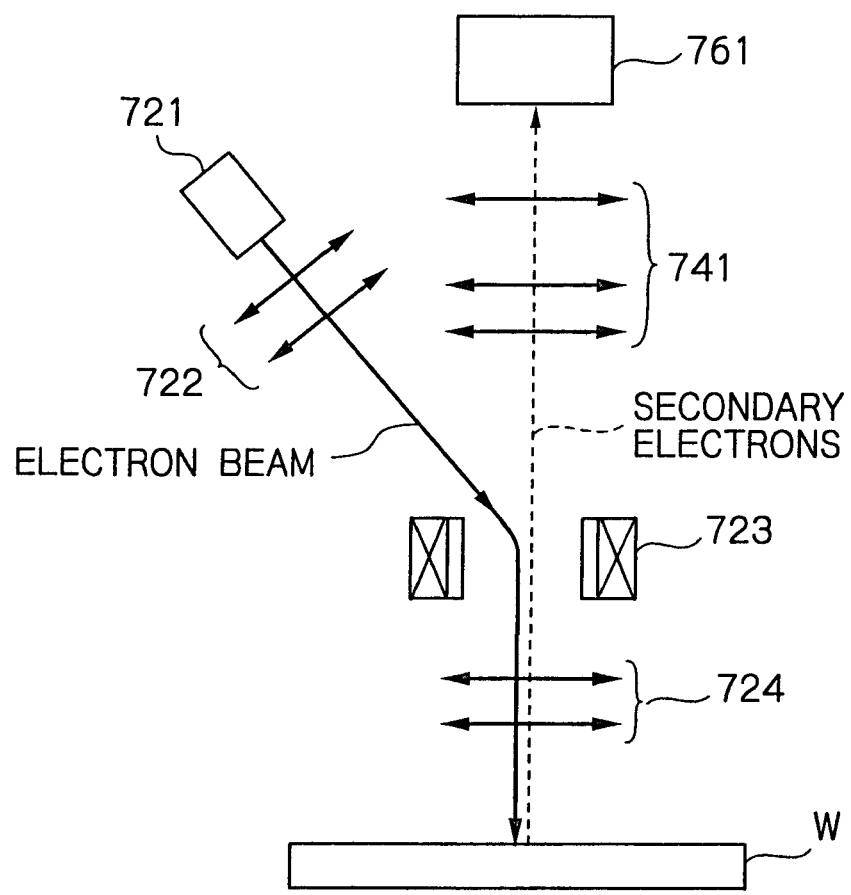
FIG. 52 is a schematic diagram exemplarily illustrating a projective electron beam inspection apparatus.
Figure 53:
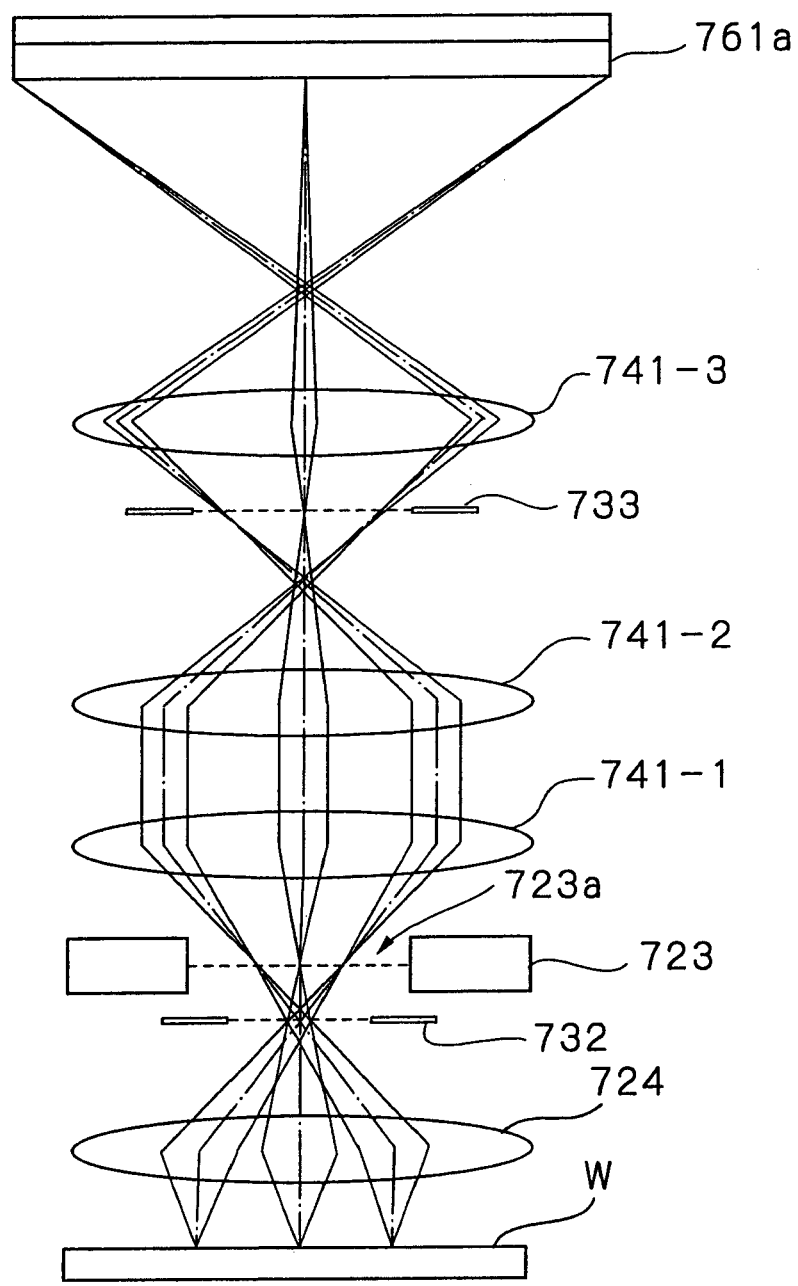
FIG. 53 is a diagram illustrating the movements of secondary electrons emitted from a rectangular area.
Figure 54:
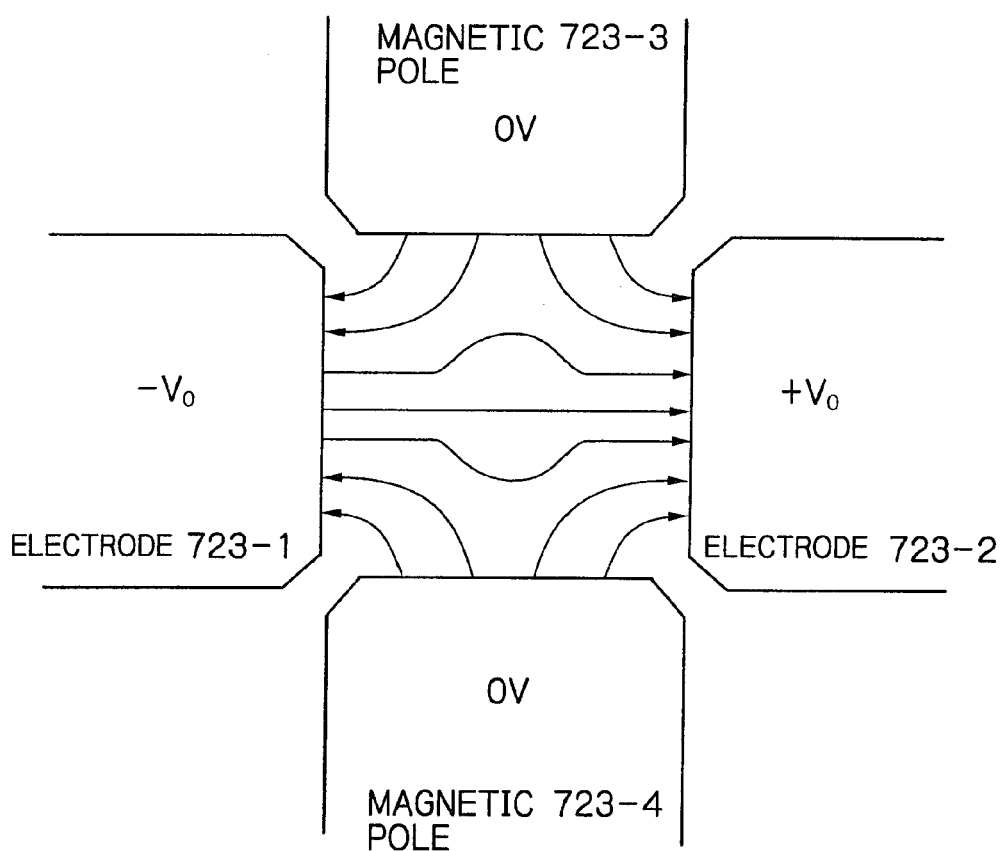
FIG. 54 is a diagram illustrating an electric field distribution of an E.times.B separator of the prior art.

A wafer to be inspected is, after having been positioned on an ultra-precise X-Y stage through an atmosphere transfer system and a vacuum transfer system, secured by an electrostatic chucking mechanism or the like, and then a detect inspection is conducted according to a procedure as shown in FIG. 51B. At first, if required, a position of each die is checked and/or a height of each location is sensed, and those values are stored./In addition, an optical microscope is used to obtain an optical microscope image in an area of interest possibly including defects or the like, which may also be used in, for example, the comparison with an electron beam image. Then, recipe information corresponding to the kind of wafer (for example, after which process the inspection should be applied; what is the wafer size, 20 cm or 30 cm, and so on) is entered into the apparatus, and subsequently, after a designation of an inspection place, a setting of an electronic-optical system and a setting of an inspection condition being established, a defect inspection is typically conducted in real time while simultaneously obtaining the image. A fast data processing system with an algorithm installed therein executes an inspection, such as the comparisons between cells, between dies or the like, and any results would be output to a CRT or the like and stored in a memory, if desired. Those defects include a particle defect, an irregular shape (a pattern defect) and an electric defect (a broken wire or via, a bad continuity or the like); and the fast data processing system also can automatically and in realtime distinguish and categorize the defects according to their size, or whether they are a killer defect (a critical defect or the like which disables a chip). The detection of the electric defect may be accomplished by detecting an irregular contrast. For example, since a location having a bad continuity would generally be positively charged by an electron beam irradiation (about 500 eV) and thereby its contrast would be decreased, the location of bad continuity can be distinguished from normal locations. The electron beam irradiation means in that case designates an electron beam source (means for generating thermal electron, UV/photoelectron) with lower potential (energy) arranged in order to emphasize the contrast by a potential difference, in addition to the electron beam irradiation means used for a regular inspection. Before the electron beam being irradiated against the objective region for inspection, the electron beam having that lower potential (energy) is generated and irradiated. In the case of a projecting method in which the object can be positively charged particles by the irradiation of the electron beam, the electron beam source with lower potential is not necessarily arranged separately, depending on the specification of the system for the method. Further, the defect may be inspected based on the difference in contrast (which is caused by the difference in flowability of elements depending on the forward or backward direction) created by, for example, applying a positive or negative potential relative to a reference potential to a wafer or the like. This electron beam generation means may be applicable to a line-width measuring apparatus and also to an aligning accuracy measurement.

The invention claimed is:

1. An inspection apparatus for inspecting a sample by irradiating either of charged particles or electromagnetic waves onto the sample, the apparatus comprising:

a beam generator for generating either of the charged particles or the electromagnetic waves as a beam;

a stage device for mounting the sample thereon;

an electron-optical system for guiding and irradiating the beam as a primary beam onto the sample mounted on the stage device, and guiding a secondary charged particles emitted from a surface of the sample when irradiating the primary beam onto the sample;

a first detector for detecting the secondary charged particles and providing an image processing system with an electric signal corresponding to an intensity of the secondary charged particles; and a mechanism for controlling an electric charge of the sample comprising:
  an electrode located in the proximity of the sample when it has been mounted on the stage device;
  a second detector for detecting an amount of electric charge of the electrode; and
  a power source for supplying a voltage to the electrode in response to the detected amount of the electric charge, to offset the electric charge of the electrode.

2. The inspection apparatus according to claim 1, wherein the electric charge control mechanism further comprises a switch having three terminals, one of which is connected to the electrode, and the remaining two of which are connected to the second detector and the power source, respectively, and the switch is connected between the electrode and the second detector during the detection of a level of the electric charge of the electrode, and it is connected between the electrode and the power source during the offset of the electric charge of the electrode.

3. The inspection apparatus according to claim 1, wherein the inspection apparatus is a projection type, and the electrode is located between an objective lens of the electron-optical system and the stage.

4. The inspection apparatus according to claim 1, wherein the electro-optical system comprises an E×B separator for separating the primary and secondary beams entering into the E×B separator, to thereby advance the primary beam toward the sample surface and the secondary beam toward the first detector.

5. The inspection apparatus according to claim 4, wherein the E×B separator comprises: three or more pairs of non-magnetic conductive electrodes for generating an electric field and arranged to form a substantial cylinder; and a pair of parallel plate magnetic poles arranged outside of the cylinder composed of the three or more pairs of non-magnetic conductive electrodes, and the pair of parallel plate magnetic poles have projections formed in peripheral portions of surfaces thereof facing each other, to thereby compensate the outwardly convex distortion of magnetic force lines generated by the parallel plate magnetic poles.

6. The inspection apparatus according to claim 5, wherein the E×B separator has a passage made of ferromagnetic material and arranged outside of the pair of the parallel plate magnetic poles, for passing the magnetic force lines generated by the pair of the parallel plate magnetic poles, and the passage is formed in a cylindrical shape and coaxial with the cylinder composed of the three or more pairs of the non-magnetic conductive electrodes.

7. The inspection apparatus according to claim 5, wherein the parallel plate magnetic poles are made of permanent magnets.

* * * * *